(12) United States Patent
Kozlowski et al.

(10) Patent No.: US 7,067,539 B2
(45) Date of Patent: Jun. 27, 2006

(54) CANNABINOID RECEPTOR LIGANDS

(75) Inventors: Joseph A. Kozlowski, Princeton, NJ (US); Neng-Yang Shih, North Caldwell, NJ (US); Brian J. Lavey, Chatham, NJ (US); Razia K. Rizvi, Bloomfield, NJ (US); Bandarpalle B. Shankar, Branchburg, NJ (US); James M. Spitler, Westfield, NJ (US); Ling Tong, Warren, NJ (US); Ronald L. Wolin, San Diego, CA (US); Michael K. Wong, North Brunswick, NJ (US)

(73) Assignee: Schering Corporation, Kenilworth, NJ (US)

( * ) Notice: Subject to any disclaimer, the term of this patent is extended or adjusted under 35 U.S.C. 154(b) by 296 days.

(21) Appl. No.: 10/214,897

(22) Filed: Aug. 7, 2002

(65) Prior Publication Data
US 2003/0232859 A1 Dec. 18, 2003

Related U.S. Application Data

(63) Continuation-in-part of application No. 10/072,354, filed on Feb. 6, 2002.

(60) Provisional application No. 60/292,600, filed on May 22, 2001, provisional application No. 60/267,375, filed on Feb. 8, 2001.

(51) Int. Cl.
A61K 31/444 (2006.01)
A61K 31/435 (2006.01)
C07D 213/70 (2006.01)
C07D 213/71 (2006.01)
C07D 213/89 (2006.01)

(52) U.S. Cl. .................. 514/347; 514/335; 514/345; 514/347; 546/255; 546/290; 546/294

(58) Field of Classification Search ............... 546/294, 546/290, 329, 255; 514/347, 345, 354, 335
See application file for complete search history.

(56) References Cited

U.S. PATENT DOCUMENTS

| 3,715,375 | A | * | 2/1973 | Shen et al. ............... 564/49 |
| 4,170,648 | A | | 10/1979 | Owen et al. ............. 424/200 |
| 4,466,965 | A | | 8/1984 | Stout et al. |
| 4,468,389 | A | | 8/1984 | Ollinger et al. ........... 424/215 |
| 4,567,184 | A | | 1/1986 | Musser et al. |
| 4,781,866 | A | | 11/1988 | Maryanoff et al. ........ 260/506 |
| 5,332,820 | A | | 7/1994 | Duncia et al. |
| 5,338,753 | A | | 8/1994 | Burstein et al. |
| 5,462,960 | A | | 10/1995 | Barth et al. |
| 5,486,525 | A | | 1/1996 | Summers, Jr. et al. |
| 5,532,237 | A | | 7/1996 | Gallant et al. |
| 5,747,524 | A | | 5/1998 | Cullinan et al. |
| 5,925,768 | A | | 7/1999 | Barth et al. |
| 5,948,777 | A | | 9/1999 | Bender et al. |
| 5,990,170 | A | | 11/1999 | Della Valle et al. |
| 6,013,648 | A | | 1/2000 | Rinaldi et al. |
| 6,017,919 | A | | 1/2000 | Inaba et al. |

FOREIGN PATENT DOCUMENTS

| DE | 28 38 988 A1 | 6/1978 |
| DE | 19533644 | 9/1995 |
| DE | 197 40 785 A1 | 9/1997 |
| EP | 00/50225 A1 | 9/1981 |
| EP | 00/65658 A2 | 4/1982 |
| EP | 00/85028 A2 | 1/1983 |
| EP | 0181568 | 5/1986 |
| EP | 02/19429 A1 | 10/1986 |
| EP | 02/64019 A2 | 9/1987 |
| EP | 02/64020 A2 | 9/1987 |
| EP | 02/74867 A2 | 12/1987 |
| EP | 05/60407 A1 | 12/1987 |
| EP | 05/87193 A1 | 2/1990 |
| EP | 0401030 | 12/1990 |
| EP | 0407217 | 1/1991 |
| EP | 04/54067 A1 | 4/1991 |
| EP | 04/78363 A2 | 9/1991 |
| EP | 1031571 | 8/2000 |
| EP | 1283039 | 2/2003 |
| JP | 06072979 | 3/1994 |
| WO | WO 87/05781 | 10/1987 |
| WO | WO 87/05898 | 10/1987 |

(Continued)

OTHER PUBLICATIONS

International Search Report for PCT/US 03/24398 dated Aug. 5, 2003 for AL01381K—6 Pages.

(Continued)

Primary Examiner—Kamal A. Saeed
Assistant Examiner—Janet L Coppins
(74) Attorney, Agent, or Firm—Thomas Blinka

(57) ABSTRACT

The invention relates to compounds of the formula

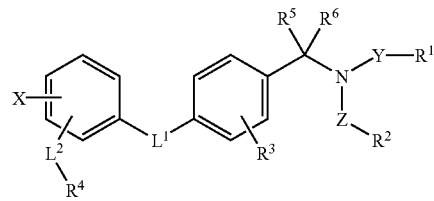

a prodrug thereof, or a pharmaceutically acceptable salt, solvate or stereoisomer of the compound or of said prodrug; which exhibit anti-inflammatory and immunodulatory activity. Also disclosed are pharmaceutical compositions containing said compounds and methods of using the compounds for the treatment of various diseases and conditions.

31 Claims, No Drawings

FOREIGN PATENT DOCUMENTS

| WO | WO 93/00313 | 1/1993 |
|---|---|---|
| WO | WO 93/21158 | 10/1993 |
| WO | WO 94/05330 | 3/1994 |
| WO | WO 95/00491 | 1/1995 |
| WO | WO 95/27693 | 10/1995 |
| WO | WO 96/23783 | 8/1996 |
| WO | WO 96/41625 | 12/1996 |
| WO | WO 97/03953 | 2/1997 |
| WO | WO 98/01422 | 1/1998 |
| WO | WO 98/10763 | 3/1998 |
| WO | WO 98/31227 | 7/1998 |
| WO | WO 98/33769 | 8/1998 |
| WO | WO 98/41519 | 9/1998 |
| WO | WO 99/26612 | 6/1999 |
| WO | WO 99/36393 | 7/1999 |
| WO | WO 99/50245 | 10/1999 |
| WO | WO 00/06146 | 2/2000 |
| WO | WO 00/56707 | 9/2000 |
| WO | WO 01/19807 A1 | 3/2001 |
| WO | WO 01/28557 A1 | 4/2001 |
| WO | WO 01/37826 | 5/2001 |
| WO | WO 01/44172 | 6/2001 |
| WO | WO 01/44239 | 6/2001 |
| WO | WO 01/64642 | 9/2001 |
| WO | WO 01/70753 | 9/2001 |
| WO | WO 01/70753 A1 | 9/2001 |
| WO | WO 01/74762 | 10/2001 |
| WO | WO 01/83460 | 11/2001 |
| WO | WO 02/42248 | 5/2002 |
| WO | WO 02/062750 | 8/2002 |
| WO | WO 03/042174 | 5/2003 |

OTHER PUBLICATIONS

M. Curtin et al., "Discovery and Evaluation of a Series of 3-Acylindole Imidazopyridine Platelet-Activating Factor Antagonists", 41(I) *J. Med. Chem.* 74-95 (1998).

G. Hartman et al., "4-Substituted Thiophene—and Furan—2-sulfonamides as topical carbonic anhydrase inhibitors" 35(21) *J. Med. Chem.* 3822-31 (1992).

G. Hartman et al., "Synthesis and derivatization of 4-(arylsulfonyl) thiophene -and—furan—2 sulfonamides", 27(2) *J. Heterocycl. Chem.* 127-34 (1990).

P. Cozzi et al., New N-(2-ethoxyethyl)-N-(4-phenoxybenzyl) dichloroacetamides as potent antiamebic agents 18(3) *Eur. J. Med. Chem.* 203-208 (1983).

U.S. Appl. No. 03/024,398 (AL01381K1) for "Cannabinoid Receptor Ligands", filed Aug. 5, 2003.

U.S. Appl. No. 10/464,174 (AL01561K) for "Cannabinoid Receptor Agonists", filed Jun. 17, 2003.

R.G. Pertwee, "Pharmacology of Cannabinoid Receptor Ligands", Curr. Med. Chem 6(8), (1999), 635-664.

T.W. Greene et al. Protective Groups in Organic Synthesis (1981), Wiley, New York.

T. Higuchi and V. Stella, Pro-drugs as Novel Drug Delivery Systems (1975) 14 of the A.C.S. Symposium Series.

Bio reversible Carriers in Drug Design, (1987) Edward B. Roche, ed., American Pharmaceutical Association and Pergamon Press.

S. Berge et al., "Pharmaceutical Salts", Journal of Pharmaceutical Sciences (1977) 66(1) 1-19.

P. Gould, "Salt Selection for Basic Drugs", International J. of Pharmaceutics (1986) 33 201-217.

Anderson et al, The Practice of Medicinal Chemistry (1996), Academic Press, New York.

Copy of International Search Report for PCT/US 03/19245 (AL01561K).

* cited by examiner

CANNABINOID RECEPTOR LIGANDS

CROSS REFERENCE TO RELATED APPLICATIONS

This application is a continuation-in-part of U.S. Ser. No. 10/072,354, filed Feb. 6, 2002, which claims the benefit of U.S. Provisional Application 60/292,600 filed May 22, 2001, and U.S. Provisional Application 60/267,375, filed Feb. 8, 2001.

BACKGROUND OF THE INVENTION

This invention relates to cannabinoid receptor ligands and, more particularly, to compounds that bind to cannabinoid ($CB_2$) receptors. Compounds according to the present invention generally exhibit anti-inflammatory and immunomodulatory activity and are useful in treating conditions characterized by inflammation and immunomodulatory irregularities. Examples of conditions which may be treated include, but are not limited to, rheumatoid arthritis, asthma, allergy, psoriasis, Crohn's disease, systemic lupus erythematosus, multiple sclerosis, diabetes, cancer, glaucoma, osteoporosis, renal ischemia, cerebral stroke, cerebral ischemia, and nephritis. The invention also relates to pharmaceutical compositions containing said compounds.

Cannabinoid receptors belong to the superfamily of G-protein coupled receptors. They are classified into the predominantly neuronal CB1 receptors and the predominantly peripheral CB2 receptors. While the effects of CB1 receptors are principally associated with the central nervous system, CB2 receptors are believed to have peripheral effects related to bronchial constriction, immunomodulation and inflammation. As such, a selective CB2 receptor binding agent is expected to have therapeutic utility in the control of diseases associated with inflammation, immunomodulation and bronchial constriction such as rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis (see, e.g., R. G. Pertwee, Curr. Med. Chem. 6(8), (1999), 635).

Various compounds have reportedly been developed which interact with $CB_2$ receptors and/or which have, inter alia, anti-inflammatory activity associated with cannabinoid receptors. See, e.g., U.S. Pat. Nos. 5,338,753, 5,462,960, 5,532,237, 5,925,768, 5,948,777, 5,990,170, 6,013,648 and 6,017,919.

SUMMARY OF THE INVENTION

This invention relates to compounds of formula I:

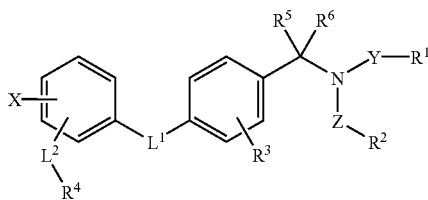

or a pharmaceutically acceptable salt or solvate thereof; wherein:

$R^1$ is selected from the group consisting of H, alkyl, halo$C_1$–$C_6$ alkyl, cycloalkyl, cycloalkylNH—, arylalkyl, heterocycloalkyl, heteroaryl, —N($R^2$)$_2$, —N($R^2$)aryl, unsubstituted aryl and aryl substituted with one to three X, wherein each $R^2$ can be the same or different and is independently selected when there are more than one $R^2$ present;

$R^2$ is selected from the group consisting of H and $C_1$–$C_6$ alkyl;

$R^3$ is 1–3 substituents selected from the group consisting of H, $C_1$–$C_6$ alkyl, Cl, F, $CF_3$, $OCF_2H$, $OCF_3$, OH and $C_1$–$C_6$ alkoxy, wherein $R^3$ can be the same or different and is independently selected when there are more than one $R^3$ present;

$R^4$ is selected from the group consisting of H, $C_1$–$C_6$ alkyl, $C_1$–$C_6$ alkoxy, cycloalkyl, alkenyl, aryl, benzyl, heteroaryl, heterocycloalkyl, arylNH—, heteroarylNH—, cycloalkylNH—, N($R^2$)$_2$, or N($R^2$)aryl, said alkyl, alkoxy, cycloalkyl, alkenyl, phenyl, pyridine-N-oxide and heteroaryl optionally substituted with one to three X, wherein X can be the same or different and is independently selected when there are more than one X present;

$R^5$ is H or $C_1$–$C_6$ alkyl;

$R^6$ is H or $C_1$–$C_6$ alkyl; or $R^5$ and $R^6$ taken together with the carbon atom to which they are attached form a carbonyl group;

$L^1$ is

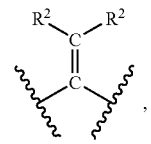

—C($R^2$)$_2$—, —C(O)—, —CHO$R^2$—, —C=NO$R^5$—, —$SO_2$—, —SO—, —S—, —O—, —N($R^2$)—, —C(O)N$R^2$—, —N($R^2$)C(O)—, —CHCF$_2$— or —CF$_2$—;

$L^2$ is a covalent bond, $C_1$–$C_6$ alkylene, —C($R^2$)$_2$—,

—CHO$R^2$—, —C($R^2$)OH, —C=NO$R^5$—, —$SO_2$—, —N($R^2$)$SO_2$—, —SO—, —S—, —O—, —$SO_2$N($R^2$)—, —N($R^2$)$_2$—, —C(O)N($R^2$)— or —N($R^2$)C(O)—;

X is selected from the group consisting of H, halogen, $CF_3$, CN, $OCF_2H$, $OCF_2CF_3$, $OCF_3$, O$R^2$, C$_1$–C6 alkyl, cycloalkyl, cycloalkoxy, $C_1$–$C_6$ alkoxy, alkoxy$C_1$–$C_6$ alkoxy, O-cycloalkyl, cycloalkylamino, cycloalkylalkoxy, heteroalkyl, —OSO$_2$$R^2$, —COO$R^2$, —CON($R^2$)$_2$, N($R^2$)$_2$, and N$R^2$aryl, wherein X can be the same or different, and is independently selected when there are more than one X present;

Y is a covalent bond, —CH$_2$—, —SO$_2$—, or —C(O)—;

Z is a covalent bond, —CH$_2$—, —SO$_2$— or —C(O)—; or

Y, $R^1$, Z and $R^2$ can be taken together with the nitrogen atom to which they are attached to form a heterocycloalkyl; with the following provisos:

$L^2$ and $R^4$, when taken together, cannot have two heteroatoms covalenty bonded together;

when $R^2$ is H, Z cannot be —S(O)—, —$SO_2$—, or —C(O)—; and when Y is a covalent bond, $R^1$ cannot form a N—N bond with the nitrogen atom.

Cannabinoid receptor ligands according to the present invention have anti-inflammatory activity and/or immunomodulatory activity and are useful in the treatment of various medical conditions including, e.g., cutaneous T cell lymphoma, rheumatoid arthritis, systemic lupus erythematosus, multiple sclerosis, glaucoma, diabetes, osteoporosis, renal ischemia, myocardial infarction, cerebral stroke, cerebral ischemia, nephritis, hepatitis, glomerulonephritis, cryptogenic fibrosing aveolitis, psoriasis, atopic dermatitis, vasculitis, allergy, seasonal allergic rhinitis, Crohn's disease, inflammatory bowel disease, reversible airway obstruction, adult respiratory distress syndrome, asthma, chronic obstructive pulmonary disease (COPD) or bronchitis. It is contemplated that one or more compounds of this invention can be useful in treating more than one of the diseases listed.

Additionally, one or more compounds of the present invention can be co-administered or used in combination with one or more disease-modifying antirheumatic drugs (DMARDS) such as methotrexate, azathioprine leflunomide, penicillamine, gold salts, mycophenolate mofetil, cyclophosphamide and other similar drugs. One or more compounds of the invention can also be co-administered with or used in combination with one or more NSAIDS such as piroxicam, naproxen, indomethacin, ibuprofen and the like; one or more COX-2 selective inhibitors such as VIOXX® (i.e., rofecoxib) and CELEBREX® (i.e., celecoxib); one or more COX-1 inhibitors such as FELDENE® (i.e., piroxicam); immunosuppressives such as steroids, cyclosporine, Tacrolimus, rapamycin, muromonab-CD3 (OKT3), Basiliximab and the like; biological response modifiers (BRMs) such as ENBREL® (i.e., etanercept), REMICADE® (i.e., infliximab), IL-1 antagonists, anti-CD40, anti-CD28, IL-10, anti-adhesion molecules and the like; and other anti-inflammatory agents such as p38 kinase inhibitors, PDE4 inhibitors, TACE inhibitors, chemokine receptor antagonists, Thalidomide and/or other small molecule inhibitors of pro-inflammatory cytokine production. One or more compounds of this invention can also be co-administered with or used in combination with one or more H1 antagonists such as CLARITIN® (i.e., loratadine), CLARINEX® (i.e., desloratadine), ZYRTEC® (i.e., cetirizine hydrochloride), ALLEGRA® (i.e., fexofenadine hydrochloride), BENADRYL® (i.e., diphenhydramine hydrochloride), and other H1 antagonists. Other drugs that the compounds of the invention can be co-administered or used in combination with include ANAPROX® (i.e., naproxen sodium), ARAVA® (i.e., leflunomide), ARTHROTEC® (i.e., a combination of diclofenac and misoprostol), AZULFIDINE® (i.e., sulfasalazine), Aspirin, CATAFLAM® (i.e., diclofenac potassium), CELESTONE® SOLUSPAN® (i.e., a combination of betamethasone sodium phosphate and betamethasone acetate), CLINORIL® (i.e., sulindac), CORTONE® Acetate (i.e., cortisone acetate), CUPRIMINE® (i.e., penicillamine), DAYPRO® (i.e., oxaprozin), DECADRON® (i.e., dexamethasone), DEPEN® (i.e., penicillamine), DEPO-MEDROL® (i.e., methylprednisolone acetate), DISALCID™ (i.e., salsalate), DOLOBID® (i.e., diflunisal), NAPROSYN® (i.e., naproxen), GENGRAF™ (i.e., cyclosporine), HYDROCORTONE® (i.e., hydrocortisone), IMURAN® (i.e., azathioprine), INDOCIN® (i.e., indomethacin), LODINE® (i.e., etodolac), MOTRIN® (i.e., ibuprofen), MYOCHRYSINE® (i.e., sodium aurothiomalate), NALFON® (i.e., calcium fenoprofen), NAPRELAN® (i.e., naproxen sodium), NEORAL® (i.e., cyclosporine), ORUDIS® (i.e., ketoprofen), ORUVAIL® (i.e., ketoprofen), PEDIAPRED® (i.e., prednisolone sodium phosphate), PLAQUENIL® (i.e., hydroxychloroquine sulfate), PRELONE® (i.e., prednisolone), RELAFEN® (i.e., nabumetone, SOLU-MEDROL® (i.e., methylprednisolone sodium succinate), TOLECTIN® (i.e., tolmetin sodium), TRILISATE® (i.e., choline magnesium trisalicylate) and/or VOLTAREN® (i.e., diclofenac sodium). These include any formulations of the above-named drugs.

For the treatment of multiple sclerosis, one or more compounds of the invention can be co-administered or used in combination with AVONEX® (i.e., Interferon beta-1a), BETASERON® (i.e., Interferon beta-1b), REBIF® (i.e., interferon beta-1a) and/or COPAXONE® (i.e., glatiramer acetate). These include any formulations of the above-named drugs.

For the treatment of psoriasis, one or more compounds of the invention can be co-administered or used in combination with steroids, methotrexate, cyclosporin, XANELIN® (i.e., efalizumab), AMEVIVE® (i.e., alefacept), Vitamin D analogs, topical retinoids, anti-TNF-α compounds and/or other drugs indicated for this condition. These include any formulations of the above-named drugs.

For the treatment of asthma, one or more compounds of the invention can be co-administered or used in combination with SINGULAIRE® (i.e., montelukast sodium), ACCOLATE® (i.e., zafirlukast), Albuterol, and/or other drugs indicated for this disease. These include any formulations of the above-named drugs.

For the treatment of inflammatory bowel disease or Crohn's disease, one or more compounds of the invention can be co-administered or used in combination with sulfasalazine, budesonide, mesalamine and/or other drugs indicated for these diseases. These include any formulations of the above-named drugs.

In another aspect, the invention relates to a pharmaceutical composition comprising a therapeutically effective amount of one or more compounds of formula I in one or more pharmaceutically acceptable carriers.

DETAILED DESCRIPTION

Unless otherwise defined, the following definitions shall apply throughout the specification and claims.

When any variable (e.g., $R^2$) occurs more than one time in any constituent, its definition in each occurrence is independent of its definition at every other occurrence. Also, combinations of substituents and/or variables are permissible only if such combinations result in stable compounds.

"Alkyl" means an aliphatic hydrocarbon group which may be straight or branched and comprising 1 to about 20 carbon atoms in the chain. Preferred alkyl groups contain 1 to about 12 carbon atoms in the chain. More preferred alkyl groups contain 1 to about 6 carbon atoms in the chain. Branched alkyl means that one or more lower alkyl groups such as methyl, ethyl or propyl, are attached to a linear alkyl chain. "Lower alkyl" means a group having about 1 to about 6 carbon atoms in the chain which may be straight or branched. Preferred alkyl groups in the present invention are lower alkyl groups. Non-limiting examples of suitable alkyl groups include methyl, ethyl, n-propyl, isopropyl, n-butyl, t-butyl, n-pentyl, heptyl, nonyl, decyl, trifluoromethyl and cyclopropylmethyl.

"Alkenyl" means an aliphatic hydrocarbon group containing at least one carbon-carbon double bond and which may be straight or branched and comprising 2 to 15 carbon atoms in the chain. Preferred alkenyl groups have 2 to 2 carbon atoms in the chain; and more preferably 2 to 6 carbon atoms in the chain. Branched means that one or more lower alkyl groups such as methyl, ethyl or propyl, are attached to a linear alkenyl chain. "Lower alkenyl" means 2 to 6 carbon atoms in the chain which may be straight or branched. Non-limiting examples of suitable alkenyl groups include ethenyl, propenyl, n-butenyl, 3-methylbut-2-enyl, and n-pentenyl.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Haloalkyl" or "halogenated alkyl" means alkyl having one or more halo atom substituents. Non-limiting examples include —$CH_2Cl$, —$CHCl_2$, —$CCl_3$, —$CH_2F$, —$CHF_2$, —$CF_3$, —$CH_2$—$CH_2Cl$, —$CH_2$—$CHCl_2$, and —CHCl—$CH_2Cl$.

"Heteroalkyl" means straight or branched alkyl chain as defined above comprising 1 or more heteroatoms, which can be the same or different, and are independently selected from the group consisting of N, O and S.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, phenylethyl and naphthalenylmethyl. The aralkyl is linked to an adjacent moiety through the alkyl.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylamino, arylamino, alkylaryl, heteroaralkyl, alkylheteroaryl, hydroxy, hydroxyalkyl, alkoxy, aryloxy, aralkoxy, aralkyloxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio and cycloalkyl.

"Cycloalkyl" means a non-aromatic mono- or multicyclic fused ring system comprising 3 to 10 ring carbon atoms, preferably 3 to 7 ring carbon atoms, more preferably 3 to 6 ring carbon atoms. The cycloalkyl can be optionally substituted with one or more "ring system substituents" which may be the same or different, and are as defined above. Non-limiting examples of suitable monocyclic cycloalkyls include cyclopropyl, cyclobutyl, cyclopentyl, cyclohexyl and the like. Non-limiting examples of suitable multicyclic cycloalkyls include 1-decalinyl, norbornenyl, adamantyl and the like.

"Cycloheteroalkyl" means a non-aromatic mono- or multicyclic fused ring system comprising 3 to 10 ring carbon atoms, preferably 3 to 7 ring carbon atoms, more preferably 3 to 6 ring carbon atoms, wherein the cycloheteroaryl has 1 or 2 heteroatoms independently selected from O, S or N, said heteroatom(s) interrupting a carbocyclic ring structure provided that the rings do not contain adjacent oxygen and/or sulfur atoms. The cycloheteroalkyl can be optionally substituted with one or more "ring system substituents" which may be the same or different, and are as defined above.

The term "optionally substituted" means optional substitution with the specified groups, radicals or moieties.

The term "solvate" as used herein means an aggregate that consists of a solute ion or molecule with one or more solvent molecules, for example, a hydrate containing such ions.

As used herein, the terms "composition" and "formulation" are intended to encompass a product comprising the specified ingredients, as well as any product which results, directly or indirectly, from combination of the specified ingredients. "Heterocycloalkyl" means cycloalkyl containing one or more heteroatoms.

"Aryl" means an aromatic monocyclic or multicyclic ring system comprising from 6 to 14 carbon atoms. Non-limiting examples include phenyl, naphthyl, indenyl, tetrahydronaphthyl and indanyl. The aryl can be optionally substituted with one or more "ring system substituents" which may be the same or different, and are as defined above.

"Heteroaryl" means a single ring or benzofused heteroaromatic group of 5 to 10 atoms comprised of 1 to 9 carbon atoms and 1 or more heteroatoms independently selected from the group consisting of N, O and S. N-oxides of the ring nitrogens are also included, as well as compounds wherein a ring nitrogen is substituted by a $C_1$–$C_6$ alkyl group to form a quaternary amine. Examples of single-ring heteroaryl groups are pyridyl, oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Examples of benzofused heteroaryl groups are indolyl, quinolyl, isoquinolyl, phthalazinyl, benzothienyl (i.e., thionaphthenyl), benzimidazolyl, benzofuranyl, benzoxazolyl and benzofurazanyl. All positional isomers are contemplated, e.g., 2-pyridyl, 3-pyridyl and 4-pyridyl.

"Alkoxy" means an alkyl radical attached by an oxygen, i.e., alkoxy groups having 1 to 9 carbon atoms.

"Oxime" means a CH(:NOH) radical containing moiety.

The term "prodrug," as used herein, represents compounds which are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

"Patient" includes both human and animals.

"Mammal" means humans and other mammalian animals.

Linker groups such as $L^1$, $L^2$, Y and Z are divalent.

In a preferred group of compounds of formula I $L^1$ is —$SO_2$—, —$CH_2$—, —$CHCH_3$—, —C(O)—, —C=$NOR^5$—, —$C(CH_3)_2$—, —CHOH—, —O—, —S— or —S(O)—;

$L^2$ is —$SO_2$—, —C(O)—, —$CH_2$—, —$CH(CH_3)$—, —$C(CH_3)_2$—,

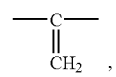

—NH—, —O—, —$NHSO_2$—, —NHC(O)—, or

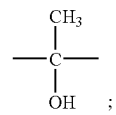

R$^1$ is H, —CH$_3$NH$_2$, —CH$_2$CF$_3$, —NHC$_3$H$_7$, —NHC$_2$H$_6$, —NHC$_4$H$_9$, C$_1$–C$_6$ alkyl, —CF$_3$, —CH(CH$_2$)$_2$, thiophenyl, morpholinyl, cyclopropyl, benzyl, naphthyl, —C(CH$_3$)$_3$, NHphenyl, 3,5-difluorophenyl, phenyl, N-cyclopentyl or N(CH$_3$)$_2$;

R$^2$ is H or CH$_3$;

R$^3$ is OH;

R$^4$ is furanyl, pyridyl, pyrimidyl, thiophenyl, quinolyl, t-butoxy, alkoxyl, cyclohexyl, phenyl, tolyl, C$_3$H$_7$, pyrimdyl, methoxyphenyl, morpholinylphenyl or CH$_3$; with the proviso that when R$^4$ is t-butoxy, L$^2$ must be —C(O)—, —CH$_2$—, —CHCH$_3$—, —C(CH$_3$)$_2$— or

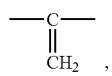

all of the above optionally substituted with one to three X, wherein X can be the same or different and are independently selected when the are more than one X present;

R$^5$ and R$^6$ are independently H or CH$_3$;

Y is a covalent bond, —SO$_2$— or —C(O)—;

Z is a covalent bond; or

R$^1$, Y, R$^2$ and Z taken together with the nitrogen atom form a morpholinyl group.

In a more preferred embodiment of the invention,

X is halogen, OH, or cyclopropyl;

R$^3$ is OH;

R$^5$ and R$^6$ are independently H or CH$_3$;

X is H, halogen, CF$_3$, OCH$_3$, OH, OCF$_3$, OCF$_2$H, CH$_3$ or C$_1$–C$_6$ cycloalkyl;

Y is a covalent bond;

Z is —SO$_2$— or —C(O)—;

L$^1$ is —SO$_2$— or —CH$_2$—;

L$^2$ is —SO$_2$—;

R$^1$ is CH$_3$ or CF$_3$; and

R$^4$ is phenyl, pyrimidyl or pyridyl, said phenyl, pyrimidyl or pyridyl groups optionally substituted with one to three substituents selected from the group consisting of C$_1$–C$_6$ alkyl, C$_1$–C$_6$ alkoxy, OH, CF$_3$ and halogen, wherein said substituents can be the same or different and are independently selected when there are more than one subsituent.

More preferably, the phenyl is substituted with OCH$_3$ or halogen selected from fluorine and chlorine.

Compounds of the invention may have at least one asymmetrical carbon atom and therefore all isomers, including diastereomers and rotational isomers are contemplated as being part of this invention. The invention includes (+)- and (−)-isomers in both pure form and in admixture, including racemic mixtures. Isomers can be prepared using conventional techniques, either by reacting optically pure or optically enriched starting materials or by separating isomers of a compound of formula I. Those skilled in the art will appreciate that for some compounds of formula I, one isomer may show greater pharmacological activity that other isomers.

Compounds of formula I can exist in unsolvated and solvated forms, including hydrated forms. In general, the solvated forms, with pharmaceutically acceptable solvents such as water, ethanol and the like, are equivalent to the unsolvated forms for purposes of this invention.

Compounds of the invention with a basic group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., compounds where R$^2$ is a hydrogen covalently bonded to N). Acidic compounds according to the present invention can form pharmaceutically acceptable salts with inorganic and organic bases. Examples of such salts are the sodium, potassium, calcium, aluminum, magnesium, zinc, lithium, gold and silver salts. Also included are salts formed with pharmaceutically acceptable amines such as ammonia, alkyl amines, hydroxyalkylamines, N-methylglucamine, piperazines and other amines.

Compounds of the present invention are generally prepared by processes known in the art, for example by the processes described below.

The following abbreviations are used in the procedures and schemes: aqueous (aq), anhydrous (anhyd), n-butyl-lithium (n-BuLi), dibromodimethylhydantoin (DBDMH), diisopropylethylamine (DIPEA), diethyl ether (Et$_2$O), dimethylacetamide (DMA), dimethyl sulfoxide (DMSO), 1-(3-dimethylaminopropyl)-3-ethylcarbodiimide hydrochloride (EDCl), ethanol (EtOH), ethyl acetate (EtOAc), 2-propanol (IPA), leaving group (LG), lithium hexamethyldisilazide (LHMDS), meta-chloroperoxybenzoic acid (MCPBA), methanesulfonic acid (MsOH), methanesulfonyl chloride (MsCl), N-iodosuccinamide (NIS), preparative thin layer chromatography on Merck-silica plates (PTLC), phenyl (Ph), pyridinium chlorochromate (PCC), pyridine (Py), trifluoroacetic anhydride (TFAA), triflic anhydride (Tf$_2$O), tetrahydrofuran (THF), silica gel chromatography (sgc), thin layer chromatography (TLC), room temperature (rt), hours (h), minutes (min), molar (M), pounds per square inch (psi), and saturated aqueous sodium chloride solution (brine).

General Scheme I
Preparation of Aryl-Bis-Sulfone Compounds
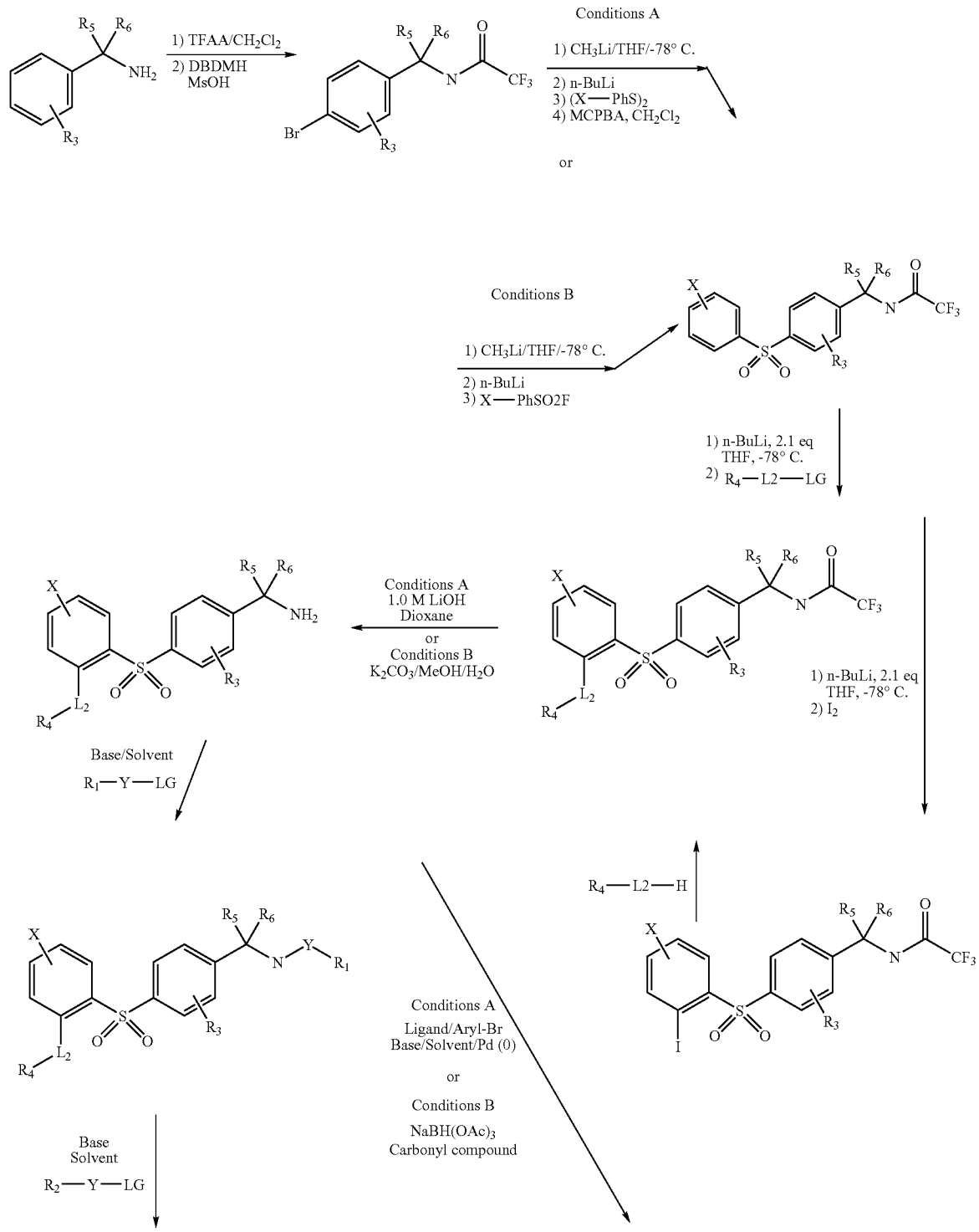

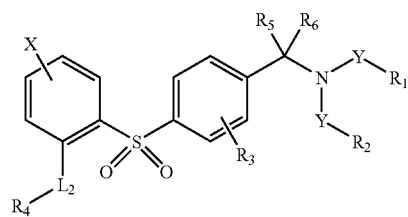
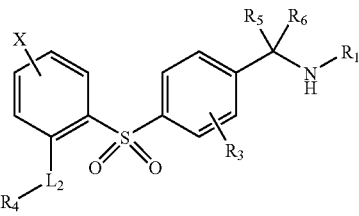
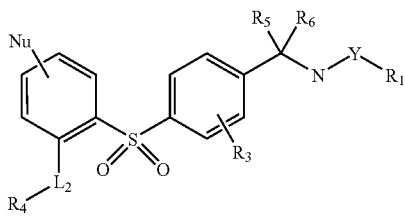

Description of Reactions—General Scheme I

In step 1, trifluoroacetic anhydride is dissolved in a suitable inert solvent such as methylene chloride and reacted with a benzyl amine at room temperature for 1–5 hr. MsOH (2 eq) is added followed by DBDMH and the reaction mixture is stirred overnight at room temperature and subjected to aqueous work up. The crude product is recrystallized from a mixture of $Et_2O$ and hexanes or purified via chromatography.

In step 2, the product of step 1 is dissolved in THF, cooled in a dry ice/IPA bath and treated with methyllithium then n-BuLi. The resulting dianion may be trapped with a sulfonyl fluoride or a disulfide. If a disulfide is the trapping agent, the resulting product is oxidized with MCPBA in $CH_2Cl_2$ at room temperature for 1–6 h. The product may be purified via chromatography or crystallization.

In step 3, the product of step 2 is dissolved in THF and treated with n-BuLi at −78° C. to form a dianion that is trapped with a suitable electrophile.

Alternatively, in step 3 the product of step 2 is dissolved in THF treated with n-BuLi at −78° C. to form a dianion which is trapped with iodine to provide the iodo substituted product. The product may be purified via sgc or crystallization. The iodo product can be converted to a similar product by nucleophilic aromatic substitution with a variety of nucleophiles, including amines, alcohols, and thiols.

In step 4, the product of step 3 is dissolved in a suitable solvent such as dioxane, ethanol, methanol or THF and an alkali metal hydroxide or carbonate such as lithium hydroxide or potassium carbonate is added either as an aqueous solution or as a solid. The reaction mixture is stirred at room temperature for 0.5–24 h. The product may be purified via sgc or crystallization.

In step 5, a combination of the product of step 4 and a tertiary amine base was dissolved in a suitable solvent such as $CH_2Cl_2$ or dioxane, at room temperature, cooled, and a suitable electrophile is added. The reaction mixture is stirred between −78° C. and 100° C. for 0.5 to 48 h. The product may be purified via sgc or crystallization.

In step 6, the product of step 5 is dissolved in a suitable inert solvent such as THF or $CH_2Cl_2$ and treated with a suitable base such as NaH or triethylamine. An electrophile is added and the reaction mixture is stirred between 0° C. and 100° C. for 0.5 to 48 h. The product may be purified via sgc or crystallization.

General Scheme II
Preparation of Methylene Linked Compounds

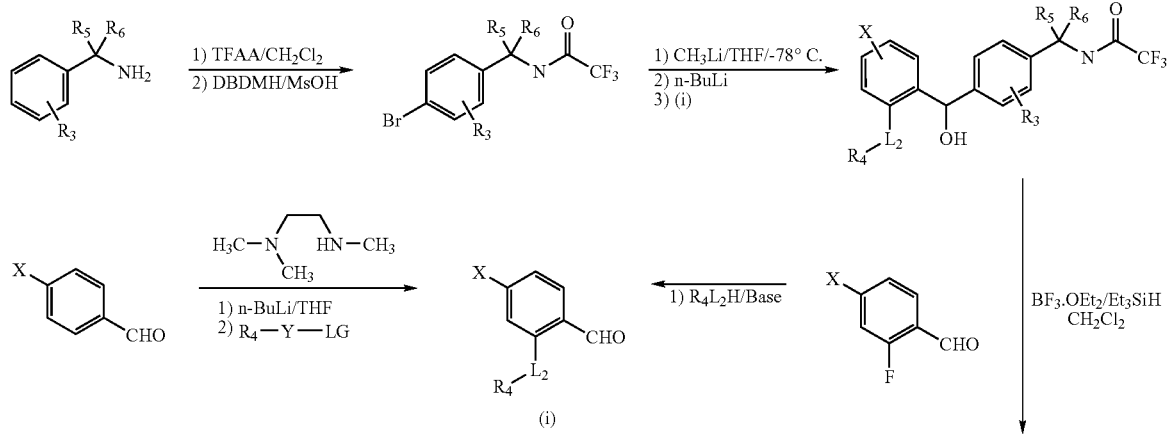

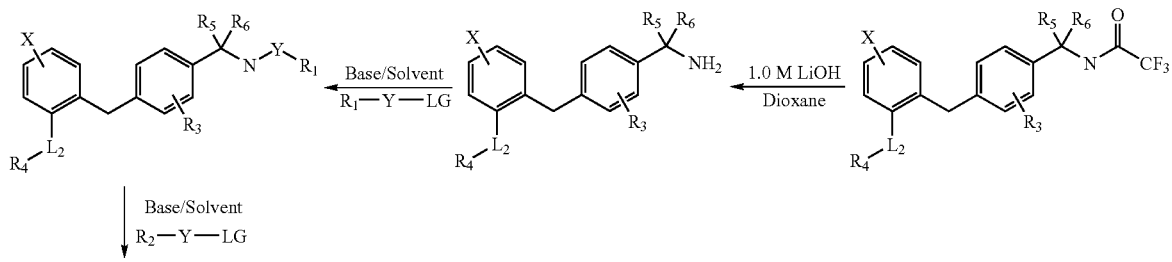

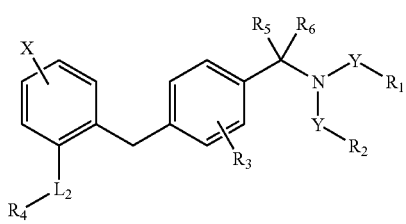

Description of Reactions—General Scheme II

In step 1, trifluoroacetic anhydride is dissolved in a suitable inert solvent such as methylene chloride and treated with a benzyl amine at ambient temperature, then stirred for 1–5 h. Methanesulfonic acid (2 eq) is added followed by dibromodimethylhydantoin and the reaction mixture is stirred overnight at rt and subjected to aqueous work up. The product may be purified by chromatography or crystallization.

In step 2, the product of step 1 is dissolved in THF, cooled in a dry ice/acetone bath (−78° C.) and treated with methyllithium, then n-BuLi. The dianion is then treated with a THF solution containing the aldehyde (i). The resulting mixture is warmed to rt and stirred for 10 h. The product is purified by chromatography.

In step 3, the alcohol product from step 2 is dissolved in methylene chloride and treated with ten fold excess of triethylsilane followed by a slight excess of boron trifluoride etherate. The resulting mixture is stirred at room temperature for 4 h, and purified by chromatography.

In step 4, the product of step 3 is dissolved in a suitable solvent such as dioxane, ethanol, or THF and an alkali metal hydroxide such as lithium hydroxide is added either as an aqueous solution or as a solid. The reaction mixture is stirred at rt for 0.5–24 h.

In step 5, the product of step 4 is dissolved in a mixture of a suitable inert solvent such as $CH_2Cl_2$ or dioxane and a tertiary amine base, and a suitable electrophile is added. The reaction mixture is stirred between −78° C. and 100° C. for 0.5 to 48 h.

In step 6, the product of step 5 is dissolved in a suitable inert solvent such as THF or $CH_2Cl_2$ and treated with a suitable base such as NaH or triethylamine. An electrophile is added and the reaction mixture is stirred between 0° C. and 100° C. for 0.5 to 48 h.

The aldehyde (i) used in step 2 was prepared by one of the following two procedures; 1) Regioselective ortho lithiation of a 4-substituted benzaldehyde, and quenching with a substituted phenyl disulfide followed by oxidation with metachloroperoxybenzoic acid to the sulfone. 2) Base promoted displacement of fluoride from an ortho-fluorobenzaldehyde by a thiophenol, phenol, or aniline.

General Scheme III
Preparation of Ketone and Olefin Linked Compounds

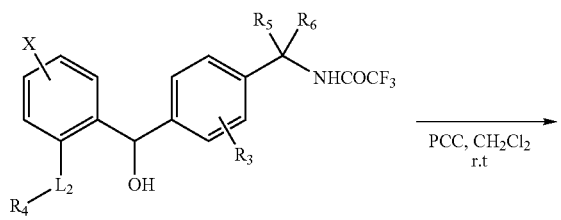

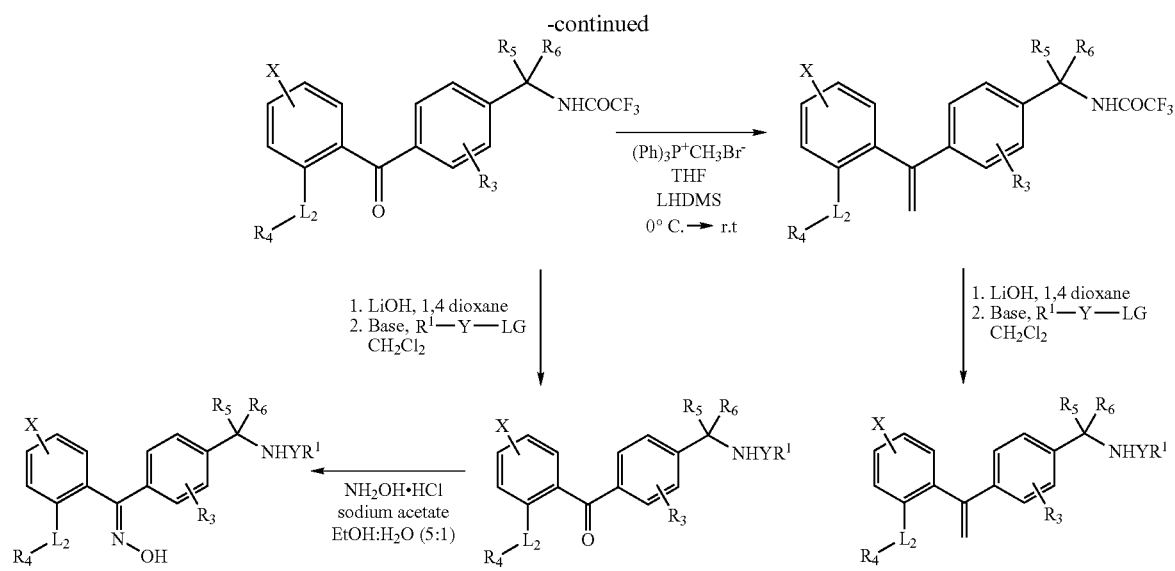

Description of Reactions—General Scheme III

In step 1 the secondary alcohol, the product of Step 2 in Scheme II is oxidized with PCC, in a suitable inert solvent such as $CH_2Cl_2$, to the carbonyl by stirring at rt for 18 h. In step 2, the ketone is treated with the ylide obtained by base treatment of dried methyltriphenylphosphonium bromide, providing the exo methylene product. In step 3 the trifluoroacetamide group can be hydrolyzed with base and reacted with a variety of acylating, sulfonylating, alkylating and other electrophilic reagents.

The ketone product can be treated with hydroxylamine hydrochloride in pyridine and heated at 80° C. for 24 h. The mixture was cooled to room temperature and the solvent removed under reduced pressure. Upon workup and purification, the oxime is obtained.

General Scheme IV
Preparation of Oxygen Linked Compounds

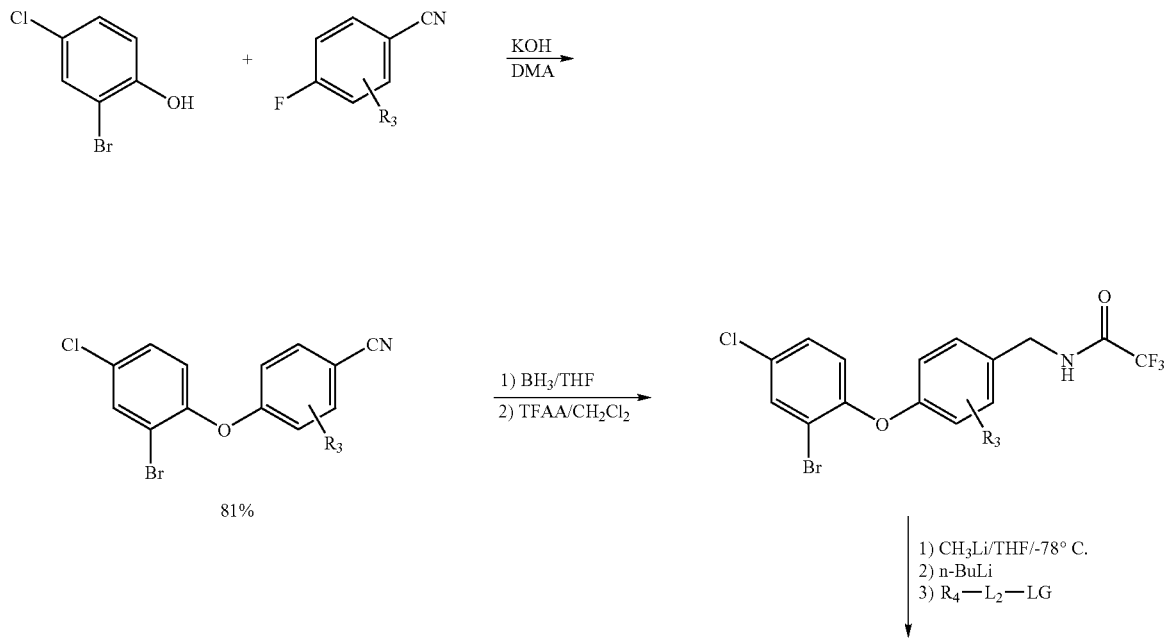

-continued

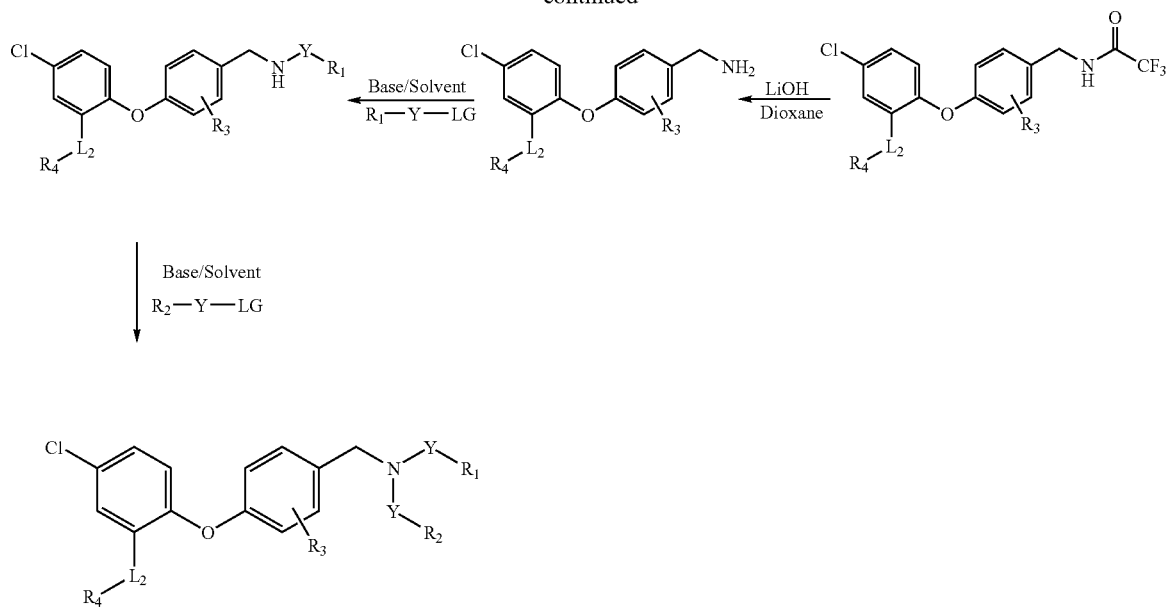

Description of Reactions—General Scheme IV

In step 1, 2-bromo-4-chlorophenol and a 4-fluorobenzonitrile are dissolved in a polar aprotic solvent such as DMA in the presence of a suitable base such as potassium hydroxide. The reaction mixture is heated for 0.5–7 days. Preferred temperatures are greater than 60° C. The reaction mixture is diluted with a suitable extraction solvent such as diethyl ether and washed with water. The solvents are removed and the product is purified via sgc.

In step 2, the product of step 1 is dissolved in a solution of diborane in THF. The reaction is stirred at reflux for 1–24 h then quenched with water and partitioned between EtOAc and aq NaOH. The solvents are evaporated and the product is purified by formation of the HCl salt in diethyl ether.

In step 3, the product of step 2 is suspended in $CH_2Cl_2$ and a suitable base such as triethylamine is added. The reaction mixture is cooled, and TFAA is added. The reaction mixture is stirred from 0.5 to 8 h, then subjected to aqueous workup. The crude product is purified by sgc.

In step 4, the product of step 3 is dissolved in THF and treated with methyl lithium, then n-BuLi at −78° C. to form a dianion that is trapped with a suitable electrophile. The reaction mixture is quenched with a suitable proton source such as aq $NH_4Cl$ or phosphate buffer then extracted with EtOAc. The product may be purified via sgc or crystallization.

In step 5, the product of step 4 is dissolved in a suitable solvent such as dioxane, ethanol, or THF and an alkali metal hydroxide such as lithium hydroxide is added either as an aqueous solution or as a solid. The reaction mixture is stirred at rt for 0.5–24 h.

In step 6, the product of step 5 is dissolved in a mixture of a suitable inert solvent such as $CH_2Cl_2$ or dioxane and a tertiary amine base, and a suitable electrophile is added. The reaction mixture is stirred between −78° C. and 100° C. for 0.5 to 48 h.

In step 7, the product of step 6 is dissolved in a suitable inert solvent such as THF or $CH_2Cl_2$ and treated with a suitable base such as NaH or triethylamine. An electrophile is added and the reaction mixture is stirred between 0° C. and 100° C. for 0.5 to 48 h.

General Scheme V
Preparation of Sulfer linked Compounds

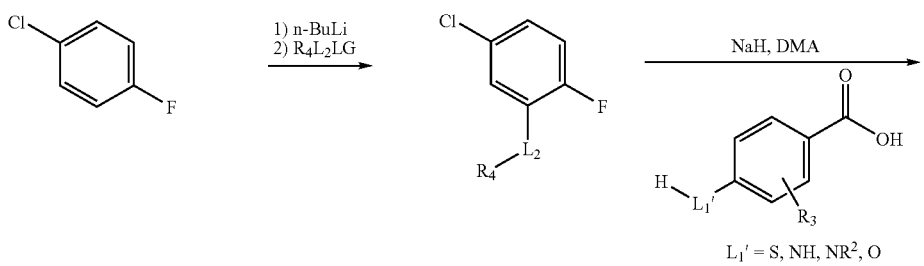

$L_1' = S, NH, NR^2, O$

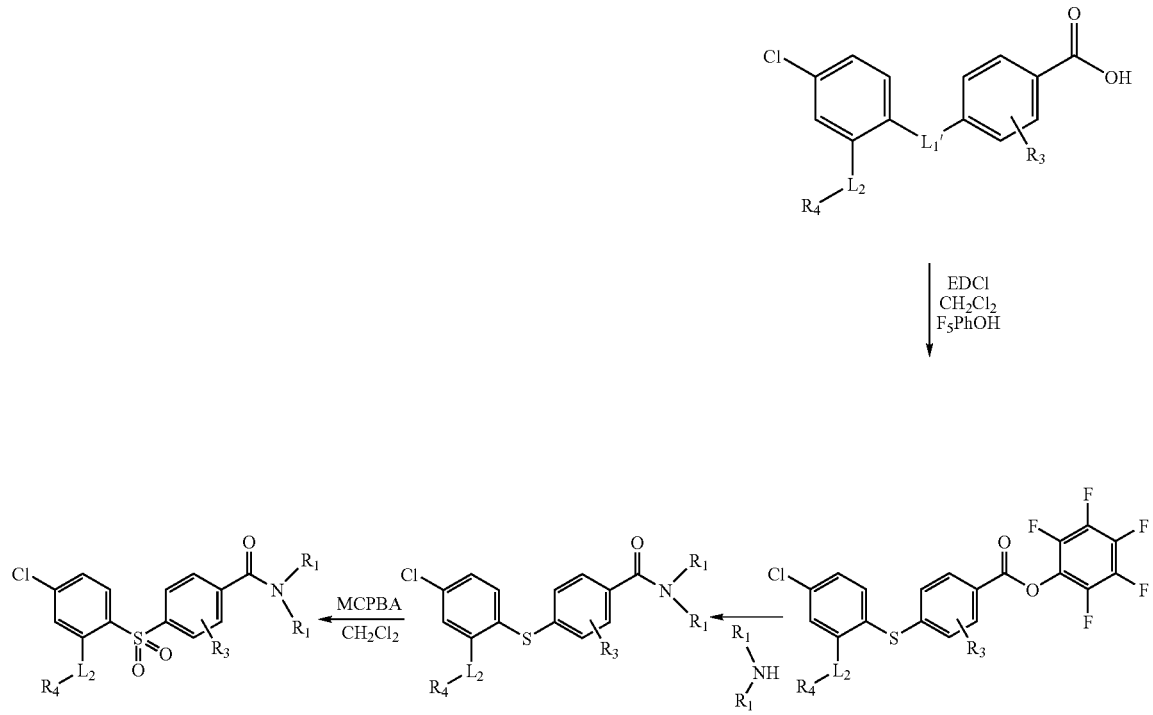

Description of Reactions—General Scheme V

In step 1, 1-chloro-4-fluorobenzene is dissolved in anhyd THF and treated with n-BuLi at −78° C. to form an anion that is trapped with a suitable electrophile. The product may be purified via sgc or crystallization.

In step 2, the product of step 1 is dissolved in a suitable polar solvent such as acetonitrile or DMA. A benzoic acid containing a nucleophilic moiety such as an OH, NHR, or SH is added, and two or more equivalents of a suitable base such as potassium hydroxide or sodium hydride is added. The reaction mixture may be stirred for 1–24 h at temperatures ranging between 0° C. and 150° C. The reaction mixture is partitioned between water and a suitable solvent such as EtOAc. The product may be purified via sgc or crystallization.

In step 3, the product of step 2 is dissolved in $CH_2Cl_2$. Pentafluorophenol and EDCl are added. The reaction mixture is stirred at rt for 0.5–24 h then partitioned between water and $CH_2Cl_2$. The solvents are evaporated. The product may be purified via sgc or crystallization.

In step 4, the product of step 3 is dissolved in a suitable solvent such as $CH_2Cl_2$. An amine base such as DIPEA or triethylamine is added, followed by a primary or secondary amine. The reaction mixture may be stirred for 1–24 h at rt. The reaction mixture is then subjected to aqueous workup and isolation and the product is purified via sgc.

In step 5, if the nucleophilic moiety in step 2 contains oxidizable functionality, the product of step 4 is dissolved in a suitable solvent such as $CH_2Cl_2$ and MCPBA is added. The reaction mixture may be stirred for 0.5–48 h then partitioned between a suitable solvent such as $CH_2Cl_2$ or EtOAc and an aqueous base such as $Na_2CO_3$. The solvent is evaporated and the product is purified via sgc.

General Scheme VI
Addition Elimination Chemistry

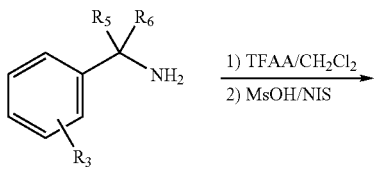

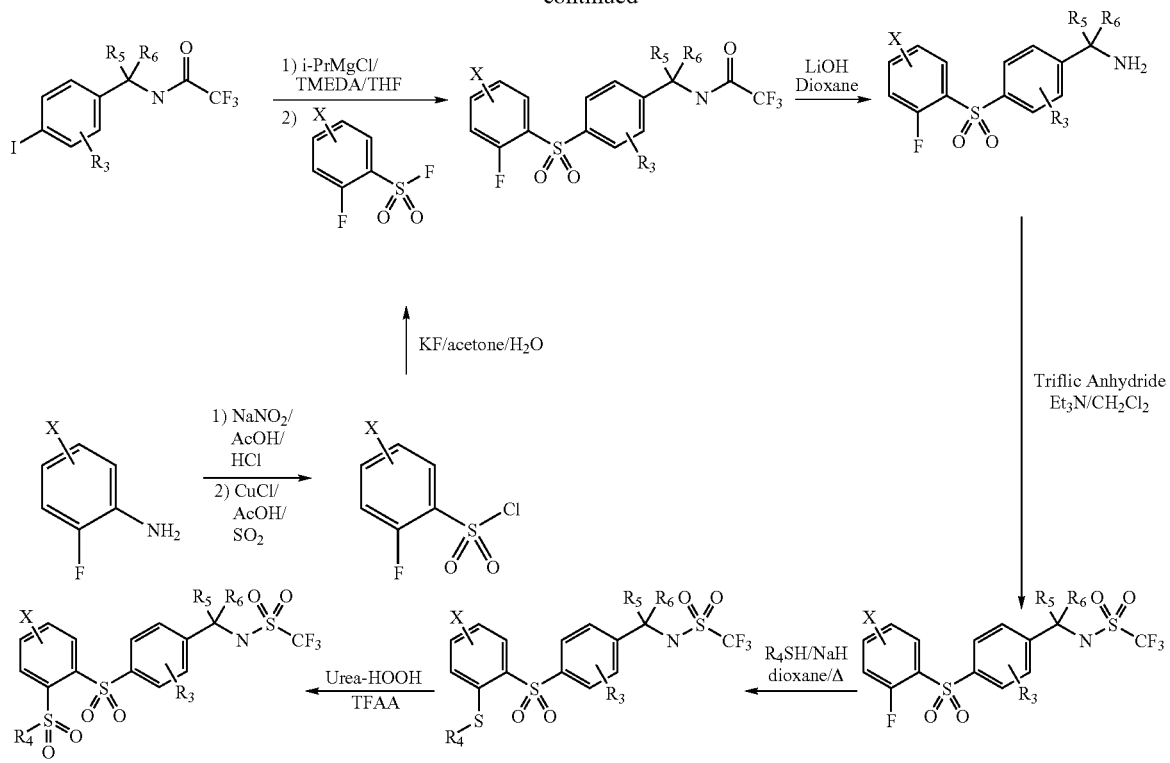

Description of Reactions—General Scheme VI

In step 1, trifluoroacetic anhydride is dissolved in a suitable inert solvent such as methylene chloride and reacted with a benzyl amine at rt for 1–5 h. Methanesulfonic acid (2 eq) is added followed by N-iodosuccinamide. The reaction mixture is stirred overnight at rt, then subjected to aqueous work up. The crude product is recrystallized from isopropanol and water.

In step 2, CuCl is dissolved in glacial acetic acid. The flask is cooled to 0° C. and $SO_2$ gas is bubbled in with stirring for 40 min. In a separate flask 2-fluoro-4-chloroaniline is dissolved in glacial acetic acid and concentrated HCl. The resulting solution is cooled to 0° C. and treated with an aqueous solution of $NaNO_2$. The reaction mixture is stirred for 30 min at 0° C. and the contents are added to the flask containing the $SO_2$ solution causing vigorous gas evolution. The reaction is then allowed to warm to rt. The product is isolated by pouring the reaction mixture onto chipped ice, then filtering the resulting solid.

In step 3, the product of step 2 is dissolved in acetone. An aqueous solution of KF (2 eq) is added and the reaction mixture is stirred for 12–24 h at rt. The reaction mixture is extracted with a suitable solvent such as $CH_2Cl_2$ or $Et_2O$ and the solvent is evaporated to afford the product.

In step 4, the product of step 1 is dissolved in THF and TMEDA is added. The flask is placed under $N_2$ blanket, and cooled to 0° C. A solution of isopropyl magnesium chloride in THF is added and the reaction mixture is stirred for 1–4 h. The resulting solution is added to a flask containing the product of step 3 that was cooled with an ice-water bath. The reaction mixture is stirred for 1–3 h. The reaction is quenched with aqueous $NH_4Cl$ and extracted with EtOAc. After evaporation of the solvent, the crude product is purified via sgc.

In step 5, the product of step 4 is dissolved in a suitable solvent such as dioxane, ethanol, or THF and an alkali metal hydroxide such as lithium hydroxide is added either as an aqueous solution or as a solid. The reaction mixture is stirred at rt for 0.5–24 h. The product may be purified via sgc or crystallization.

In step 6, the product of step 5 is dissolved in a suitable inert solvent such as $CH_2Cl_2$ or acetonitrile and a tertiary amine base, and a triflic anhydride is added. The reaction mixture is stirred between −78° C. and rt for 0.5 to 48 h. The product may be purified via sgc or crystallization.

In step 7, the product of step 6 is dissolved in a suitable inert solvent such as dioxane and a thiol is added. A base such as sodium hydride, sodium hydroxide, or NaHMDS is added and the reaction mixture is stirred at a suitable temperature between 50° C. and 100° C. for 4–24 h. The reaction mixture is quenched with water and extracted with a suitable solvent. The solvents are evaporated and the crude product is purified via sgc.

In step 8, the product of step 7 is dissolved in a suitable inert solvent such as $CH_2Cl_2$. $Na_2HPO_4$ and urea hydrogen peroxide complex is added, followed by TFAA. The reaction mixture is refluxed for 4–16 h, then partitioned between water and $CH_2Cl_2$. The solvents are evaporated and the crude product is purified via sgc.

Those skilled in the art will appreciate that similar reactions to those described in the above schemes may be carried out on other compounds of formula I as long as substituents present would not be susceptible to the reaction conditions described. Starting materials for the above processes are either commercially available, known in the art, or prepared by procedures well known in the art. Exemplary compounds of formula 1 are set forth below in Table I. CB means covalent bond.

TABLE I

| | R¹ | R² | R³ | R⁴ | R⁵ | R⁶ | L¹ | L² | X | Y | Z |
|---|---|---|---|---|---|---|---|---|---|---|---|
| A | CH₃ | H | H | 2-fluorophenyl | H | CH₃ | SO₂ | SO₂ | OCH₃ | SO₂ | CB |
| B | CH₃ | H | H | 4-methoxyphenyl | H | CH₃ | SO₂ | SO₂ | OCH₃ | SO₂ | CB |
| C | CH₃ | H | H | 2-fluorophenyl | H | CH₃ | SO₂ | SO₂ | OCF₂H | SO₂ | CB |
| D | CH₃ | H | H | t-butoxy | H | CH₃ | SO₂ | CO | OCH₃ | SO₂ | CB |
| E | CH₃ | H | H | 2-fluorophenyl | H | CH₃ | CH₂ | SO₂ | OCF₃ | SO₂ | CB |
| F | CH₃ | H | H | cyclohexyl | H | CH₃ | SO₂ | SO₂ | OCH₃ | SO₂ | CB |
| G | CH₃ | H | H | 2-fluorophenyl | H | CH₃ | SO₂ | SO₂ | CH₃ | SO₂ | CB |
| H | CF₃ | H | H | 2-fluorophenyl | H | CH₃ | CH₂ | SO₂ | CF₃ | SO₂ | CB |
| I | CH₃ | H | H | 2,4-dichlorophenyl | H | CH₃ | SO₂ | SO₂ | OCH₃ | SO₂ | CB |
| J | CH₃ | H | H | 4-chlorophenyl | H | CH₃ | SO₂ | SO₂ | OCF₃ | SO₂ | CB |
| K | CH₃ | H | H | t-butoxy | H | CH₃ | SO₂ | C=O | OCF₂H | SO₂ | CB |
| L | CH₃ | H | H | 2-fluorophenyl | H | CH₃ | SO₂ | SO₂ | Cl | SO₂ | CB |
| M | CH₃ | H | H | 4-methoxyphenyl | H | H | SO₂ | SO₂ | OCH₃ | SO₂ | CB |

TABLE I-continued

| | R¹ | R² | R³ | R⁴ | R⁵ | R⁶ | L¹ | L² | X | Y | Z |
|---|---|---|---|---|---|---|---|---|---|---|---|
| N | CH₃ | H | H | 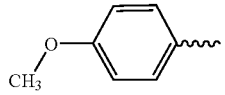 | H | H | CH₂ | SO₂ | OCH₃ | SO₂ | CB |
| O | CH₃ | H | H | 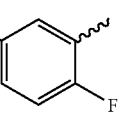 | H | CH₃ | SO₂ | SO₂ | Cl | SO₂ | CB |
| P | CH₃ | H | H | 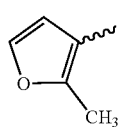 | H | CH₃ | SO₂ | SO₂ | OCH₃ | SO₂ | CB |
| Q | CH₃ | H | H | 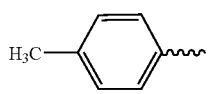 | H | CH₃ | SO₂ | SO₂ | CH₃ | SO₂ | CB |
| R | CF₃ | H | H | 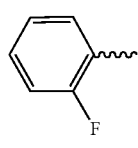 | H | CH₃ | SO₂ | SO₂ | CF₃ | SO₂ | CB |
| S | CF₃ | H | H | 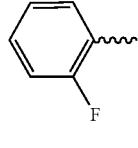 | H | CH₃ | SO₂ | SO₂ | Cl | SO₂ | CB |
| T | CH₃ | H | H | 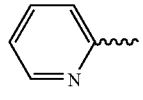 | H | CH₃ | SO₂ | SO₂ | Cl | SO₂ | CB |
| U | CH₃ | H | H | 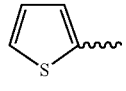 | H | CH₃ | SO₂ | SO₂ | OCH₃ | SO₂ | CB |
| V | CF₃ | H | H | 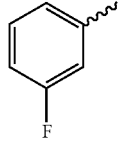 | H | CH₃ | CH₂ | SO₂ | CF₃ | SO₂ | CB |
| W | CF₃ | H | H | 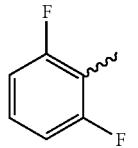 | H | CH₃ | SO₂ | SO₂ | Cl | SO₂ | CB |
| X | CF₃ | H | H | 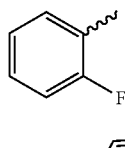 | CH₃ | CH₃ | CH₂ | SO₂ | OCF₃ | SO₂ | CB |
| Y | C₄H₉ | H | H | 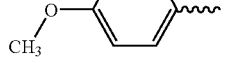 | H | CH₃ | SO₂ | SO₂ | OCH₃ | C=O | CB |

TABLE I-continued

| | R¹ | R² | R³ | R⁴ | R⁵ | R⁶ | L¹ | L² | X | Y | Z |
|---|---|---|---|---|---|---|---|---|---|---|---|
| Z | CH₃ | H | H | cyclohexyl | H | CH₃ | SO₂ | SO₂ | OCH₃ | SO₂ | CB |
| AA | CH₃ | H | H | C₃H₇ | H | CH₃ | SO₂ | SO₂ | OCH₃ | SO₂ | CB |
| AB | CH₃ | H | H | 2-F-phenyl | H | CH₃ | SO₂ | SO₂ | CF₃ | SO₂ | CB |
| AC | CH₃ | H | H | 2,6-diF-phenyl | H | CH₃ | SO₂ | SO₂ | CF₃ | SO₂ | CB |
| AE | CF₃ | H | H | 2,3-diF-phenyl | H | CH₃ | SO₂ | SO₂ | CF₃ | SO₂ | CB |
| AF | CH₃ | H | H | 4-Cl-phenyl | H | CH₃ | SO₂ | SO₂ | CF₃ | SO₂ | CB |
| AG | CF₃ | H | H | 2-Cl-phenyl | H | CH₃ | SO₂ | SO₂ | CF₃ | SO₂ | CB |
| AH | CF₃ | H | H | 2-CH₃-3-Cl-phenyl | H | CH₃ | SO₂ | SO₂ | CF₃ | SO₂ | CB |
| AI | CH₃ | H | H | 4-CF₃-phenyl | H | CH₃ | SO₂ | SO₂ | CF₃ | SO₂ | CB |
| AK | CH₃ | H | H | 4-OCH₃-3-F-phenyl | H | CH₃ | SO₂ | SO₂ | Cl | SO₂ | CB |
| AM | CH₃ | H | H | 2,5-diF-phenyl | H | CH₃ | SO₂ | SO₂ | Cl | SO₂ | CB |
| AO | CH₃ | H | H | 2-pyridyl | H | CH₃ | SO₂ | SO₂ | Cl | SO₂ | CB |
| AQ | CH₃ | H | H | cyclohexyl | H | CH₃ | SO₂ | SO₂ | Cl | SO₂ | CB |

TABLE I-continued

| | R¹ | R² | R³ | R⁴ | R⁵ | R⁶ | L¹ | L² | X | Y | Z |
|---|---|---|---|---|---|---|---|---|---|---|---|
| AR | CF₃ | H | H | 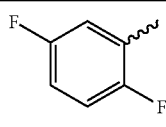 | H | CH₃ | SO₂ | SO₂ | Cl | SO₂ | CB |
| AS | CF₃ | H | H | 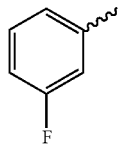 | H | CH₃ | SO₂ | SO₂ | Cl | SO₂ | CB |
| AT | N(CH₃)₂ | H | H | 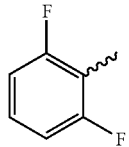 | H | CH₃ | SO₂ | SO₂ | Cl | SO₂ | CB |
| AU | CH₃ | H | H | 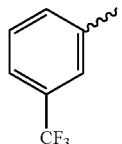 | H | CH₃ | SO₂ | SO₂ | Cl | SO₂ | CB |
| AV | CH₃ | H | H | 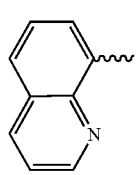 | H | CH₃ | SO₂ | SO₂ | Cl | SO₂ | CB |
| AW | CF₃ | H | H | 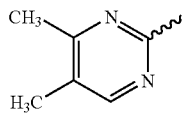 | H | CH₃ | SO₂ | SO₂ | Cl | SO₂ | CB |
| AX | CH₃ | H | H | C₃H₇ | H | CH₃ | SO₂ | SO₂ | Cl | SO₂ | CB |
| AY | CF₃ | H | H | 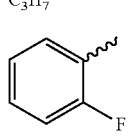 | CH₃ | CH₃ | SO₂ | SO₂ | Cl | $\overset{O}{\underset{C}{\parallel}}$ | CB |
| AZ | CF₃ | H | H | 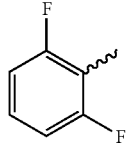 | CH₃ | CH₃ | SO₂ | SO₂ | Cl | SO₂ | CB |
| BA | CH₃ | H | H | 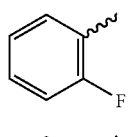 | H | CH₃ | SO₂ | SO₂ | OCF₃ | SO₂ | CB |
| BB | CH₃ | H | H | 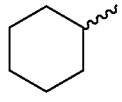 | H | CH₃ | SO₂ | SO₂ | OCF₃ | SO₂ | CB |
| BC | CH₃ | H | H | 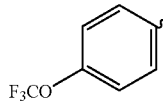 | H | CH₃ | SO₂ | SO₂ | OCF₃ | SO₂ | CB |

TABLE I-continued

| | R¹ | R² | R³ | R⁴ | R⁵ | R⁶ | L¹ | L² | X | Y | Z |
|---|---|---|---|---|---|---|---|---|---|---|---|
| BD | CF₃ | H | H | 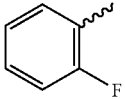 2-fluorophenyl | H | CH₃ | SO₂ | SO₂ | OCF₃ | SO₂ | CB |
| BG | CH₃ | H | H | 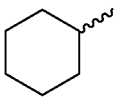 cyclohexyl | H | CH₃ | SO₂ | SO₂ | OCH₃ | SO₂ | CB |
| BH | CF₃ | H | H | 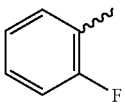 2-fluorophenyl | H | CH₃ | SO₂ | SO₂ | OCH₃ | C=O | CB |
| BJ | CF₃ | H | H | 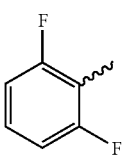 2,6-difluorophenyl | H | CH₃ | SO₂ | SO₂ | OCH₃ | SO₂ | CB |
| BN | CF₃ | H | H | C₃H₇ | H | CH₃ | SO₂ | SO₂ | OCH₃ | C=O | CB |
| BO | CF₃ | H | H | 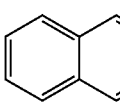 naphthyl | H | CH₃ | SO₂ | SO₂ | OCH₃ | C=O | CB |
| BP | NHC₃H₇ | H | H | 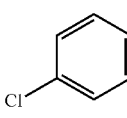 4-chlorophenyl | H | CH₃ | SO₂ | SO₂ | OCH₃ | C=O | CB |
| BR | CF₃ | H | H | 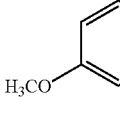 4-methoxyphenyl | CH₃ | CH₃ | SO₂ | SO₂ | OCH₃ | C=O | CB |
| BS | CH₃ | H | H | 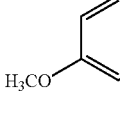 4-methoxyphenyl | CH₃ | CH₃ | SO₂ | SO₂ | OCH₃ | SO₂ | CB |
| BT | CH₃ | CH₃ | H | 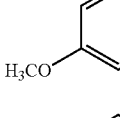 4-methoxyphenyl | CH₃ | CH₃ | SO₂ | SO₂ | OCH₃ | SO₂ | CB |
| BU | CH₃ | H | H | 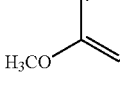 4-methoxyphenyl | H | H | SO₂ | SO₂ | OCH₃ | SO₂ | CB |
| BV | CH₃ | CH₃ | H | 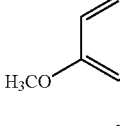 4-methoxyphenyl | H | H | SO₂ | SO₂ | OCH₃ | SO₂ | CB |
| BW | CF₃ | H | H | 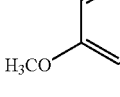 4-methoxyphenyl | H | CH₃ | SO₂ | SO₂ | OCH₃ | C=O | CB |

TABLE I-continued

| | R¹ | R² | R³ | R⁴ | R⁵ | R⁶ | L¹ | L² | X | Y | Z |
|---|---|---|---|---|---|---|---|---|---|---|---|
| BX | CH₃ | H | H | 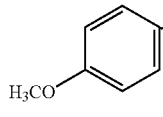 | H | CH₃ | SO₂ | SO₂ | OCH₃ | SO₂ | CB |
| BY | CH₃ | CH₃ | H | 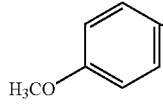 | H | CH₃ | SO₂ | SO₂ | OCH₃ | SO₂ | CB |
| BZ | CF₃ | H | H | 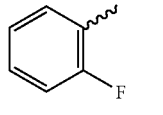 | H | CH₃ | SO₂ | SO₂ | CH₃ | SO₂ | CB |
| CA | CF₃ | H | H | 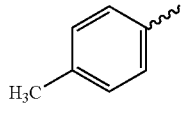 | H | CH₃ | SO₂ | SO₂ | CH₃ | SO₂ | CB |
| CB | CH₃ | H | H | 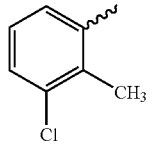 | H | CH₃ | SO₂ | SO₂ | CH₃ | SO₂ | CB |
| CC | CF₃ | H | H | C₃H₇ | H | CH₃ | SO₂ | SO₂ | Cl | C=O | CB |
| CD | CH₃ | H | H | 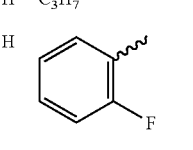 | H | CH₃ | SO₂ | SO₂ | Cl | SO₂ | CB |
| CE | CH₃ | H | H | 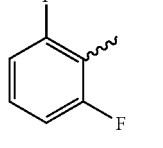 | H | CH₃ | SO₂ | SO₂ | Cl | SO₂ | CB |
| CF | —CH(CH₃)₂ | H | H | 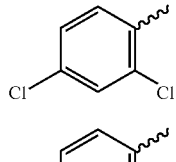 | H | CH₃ | SO₂ | SO₂ | OCH₃ | SO₂ | CB |
| CG | NH₂ | H | H | 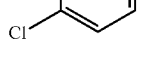 | H | CH₃ | SO₂ | SO₂ | OCH₃ | SO₂ | CB |
| CH | C₄H₉ | H | H | 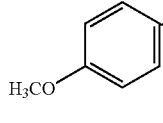 | H | CH₃ | SO₂ | SO₂ | OCH₃ | SO₂ | CB |
| CI | —CHCF₃ | H | H | 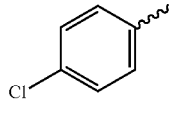 | H | CH₃ | SO₂ | SO₂ | OCH₃ | SO₂ | CB |
| CJ | 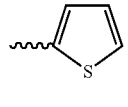 | H | H | 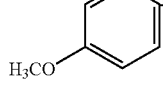 | H | CH₃ | SO₂ | SO₂ | OCH₃ | SO₂ | CB |

TABLE I-continued

| | R¹ | R² | R³ | R⁴ | R⁵ | R⁶ | L¹ | L² | X | Y | Z |
|---|---|---|---|---|---|---|---|---|---|---|---|
| CK | 3-Cl,4-F-phenyl | H | H | 4-OCH₃-phenyl | H | CH₃ | SO₂ | SO₂ | OCH₃ | SO₂ | CB |
| CL | 1-naphthyl | H | H | 4-OCH₃-phenyl | H | CH₃ | SO₂ | SO₂ | OCH₃ | SO₂ | CB |
| CM | benzyl (CH₂-phenyl) | H | H | 4-OCH₃-phenyl | H | CH₃ | SO₂ | SO₂ | OCH₃ | SO₂ | CB |
| CN | CH₃ | H | H | 4-OCH₃-phenyl | H | CH₃ | SO₂ | SO₂ | OCH₃ | C=O | CB |
| CO | cyclopropyl | H | H | 4-OCH₃-phenyl | H | CH₃ | SO₂ | SO₂ | OCH₃ | C=O | CB |
| CP | C₃H₇ | H | H | 4-Cl-phenyl | H | CH₃ | SO₂ | SO₂ | OCH₃ | C=O | CB |
| CQ | C(CH₃)₃ | H | H | 4-OCH₃-phenyl | H | CH₃ | SO₂ | SO₂ | OCH₃ | C=O | CB |
| CR | 2-thienyl | H | H | 4-OCH₃-phenyl | H | CH₃ | SO₂ | SO₂ | OCH₃ | C=O | CB |
| CS | CH₃ | H | H | 2,5-diF-phenyl | H | CH₃ | SO₂ | SO₂ | Cl | C=O | CB |
| CT | NH—(CH₂)₂-CH₃ | H | H | 4-Cl-phenyl | H | CH₃ | SO₂ | SO₂ | OCH₃ | C=O | CB |
| CU | NH-phenyl | H | H | 4-OCH₃-phenyl | H | CH₃ | SO₂ | SO₂ | OCH₃ | C=O | CB |

TABLE I-continued

| | R¹ | R² | R³ | R⁴ | R⁵ | R⁶ | L¹ | L² | X | Y | Z |
|---|---|---|---|---|---|---|---|---|---|---|---|
| CV | CF₃ | H | H | tert-butoxy | H | CH₃ | SO₂ | C=O | OH | C=O | CB |
| CW | CH₃ | H | H | 4-chlorophenyl | H | CH₃ | SO₂ | SO₂ | OH | SO₂ | CB |
| CX | CH₃ | H | H | 2-fluorophenyl | H | CH₃ | SO₂ | SO₂ | OH | SO₂ | CB |
| CZ | CF₃ | H | H | 4-chlorophenyl | H | CH₃ | SO₂ | SO₂ | OCF₂H | C=O | CB |
| DA | CH₃ | H | H | 4-chlorophenyl | H | CH₃ | SO₂ | SO₂ | OCF₂H | SO₂ | CB |
| DC | CF₃ | H | H | tert-butoxy | H | CH₃ | SO₂ | C=O | OCH₃ | SO₂ | CB |
| DD | CF₃ | H | H | tert-butoxy | H | CH₃ | SO₂ | C=O | OCH₃ | C=O | CB |
| DE | cyclopropyl | H | H | tert-butoxy | H | CH₃ | SO₂ | C=O | OCH₃ | C=O | CB |
| DF | CH₃ | H | H | tert-butoxy | H | CH₃ | SO₂ | C=O | Cl | SO₂ | CB |
| DG | CF₃ | H | H | tert-butoxy | H | CH₃ | SO₂ | C=O | Cl | SO₂ | CB |
| DH | CH₃ | H | H | 4-chlorophenyl | H | CH₃ | SO₂ | CH₂ | Cl | SO₂ | CB |
| DI | CH₃ | H | H | 4-chlorophenyl | H | CH₃ | SO₂ | C=O | Cl | SO₂ | CB |
| DJ | CH₃ | H | H | 2-fluorophenyl | H | CH₃ | SO₂ | CH₂ | Cl | SO₂ | CB |

TABLE I-continued

| | R¹ | R² | R³ | R⁴ | R⁵ | R⁶ | L¹ | L² | X | Y | Z |
|---|---|---|---|---|---|---|---|---|---|---|---|
| DK | CH₃ | H | H | 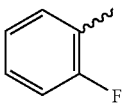 | H | CH₃ | SO₂ | C=O | Cl | SO₂ | CB |
| DL | CH₃ | H | H | 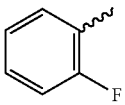 | H | CH₃ | SO₂ | C=CH₂ | Cl | SO₂ | CB |
| DM | CF₃ | H | H | 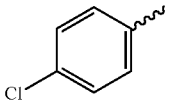 | H | CH₃ | SO₂ | 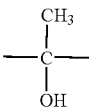 | Cl | C=O | CB |
| DN | CF₃ | H | H | 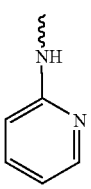 | H | CH₃ | SO₂ | C=O | Cl | C=O | CB |
| DP | CF₃ | CH₃ | H | 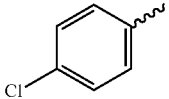 | H | CH₃ | SO₂ | C=CH₂ | Cl | C=O | CB |
| DQ | CH₃ | H | H | 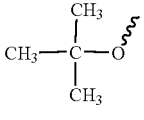 | CH₃ | CH₃ | SO₂ | C=O | Cl | SO₂ | CB |
| DR | CH₃ | H | H | 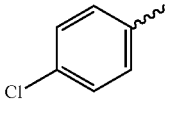 | H | CH₃ | SO₂ | NH | Cl | SO₂ | CB |
| DS | CF₃ | H | H | 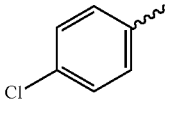 | H | CH₃ | SO₂ | O | Cl | C=O | CB |
| DU | CH₃ | H | H | 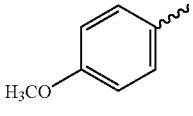 | H | CH₃ | CH₂ | SO₂ | OCH₃ | SO₂ | CB |
| DV | CH₃ | H | H | 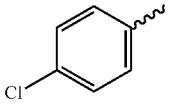 | H | CH₃ | CH₂ | SO₂ | Cl | SO₂ | CB |
| DW | CF₃ | H | H | 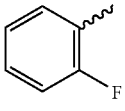 | H | CH₃ | CH₂ | SO₂ | CF₃ | SO₂ | CB |
| DX | CH₃ | H | H | 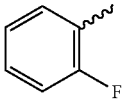 | H | CH₃ | CH₂ | SO₂ | CF₃ | SO₂ | CB |

TABLE I-continued

| | R¹ | R² | R³ | R⁴ | R⁵ | R⁶ | L¹ | L² | X | Y | Z |
|---|---|---|---|---|---|---|---|---|---|---|---|
| DY | CF₃ | H | H | 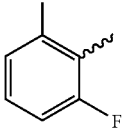 | H | CH₃ | CH₂ | SO₂ | CF₃ | SO₂ | CB |
| DZ | CH₃ | H | H | 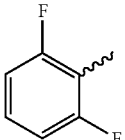 | H | CH₃ | CH₂ | SO₂ | CF₃ | SO₂ | CB |
| EA | CF₃ | H | H | 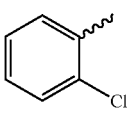 | H | CH₃ | CH₂ | SO₂ | CF₃ | SO₂ | CB |
| EC | CH₃ | H | H | 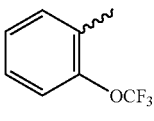 | H | CH₃ | CH₂ | SO₂ | CF₃ | SO₂ | CB |
| ED | CF₃ | H | H | 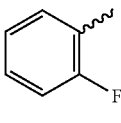 | H | CH₃ | CH₂ | SO₂ | OCF₃ | C=O | CB |
| EE | CH₃ | H | H | 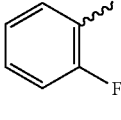 | H | CH₃ | CH₂ | SO₂ | OCF₃ | SO₂ | CB |
| EG | CH₃ | H | H | 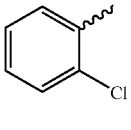 | H | CH₃ | CH₂ | SO₂ | OCF₃ | SO₂ | CB |
| EH | CF₃ | H | H | 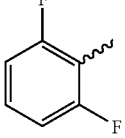 | H | CH₃ | CH₂ | SO₂ | OCF₃ | SO₂ | CB |
| EI | CF₃ | H | H | 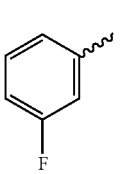 | H | CH₃ | CH₂ | SO₂ | OCF₃ | SO₂ | CB |
| EJ | CH₃ | H | H | 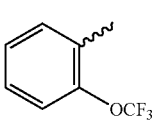 | H | CH₃ | CH₂ | SO₂ | OCF₃ | SO₂ | CB |
| EK | CF₃ | H | H | 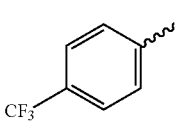 | H | CH₃ | CH₂ | SO₂ | OCF₃ | SO₂ | CB |

TABLE I-continued

| | R¹ | R² | R³ | R⁴ | R⁵ | R⁶ | L¹ | L² | X | Y | Z |
|---|---|---|---|---|---|---|---|---|---|---|---|
| EL | CH₃ | H | H | 4-methoxyphenyl | H | H | CH₂ | SO₂ | OCH₃ | SO₂ | CB |
| EN | CF₃ | H | H | 2-fluorophenyl | CH₃ | CH₃ | CH₂ | SO₂ | OCF₃ | C=O | CB |
| EP | CH₃ | H | H | 2-(N,N-diethylamino)phenyl | H | CH₃ | CH₂ | SO₂ | OCF₃ | SO₂ | CB |
| EU | CH₃ | H | H | 2-fluorophenyl | H | CH₃ | C=O | SO₂ | OCF₃ | SO₂ | CB |
| EV | CF₃ | H | H | 4-methoxyphenyl | H | CH₃ | C=H | SO₂ | OCH₃ | SO₂ | CB |
| EW | CF₃ | H | H | 2-fluorophenyl | H | CH₃ | C=H | O | H | C=O | CB |
| EX | CF₃ | H | H | benzyl (CH₂-phenyl) | H | CH₃ | C=H | O | H | C=O | CB |
| EY | CF₃ | H | H | 2-fluorophenyl | H | CH₃ | C=H | O | Cl | C=O | CB |
| EZ | CH₃ | H | H | 2-fluorophenyl | H | CH₃ | C=H | SO₂ | OCF₃ | C=O | CB |
| FA | CF₃ | H | H | 4-methoxyphenyl | H | CH₃ | C=H | NHSO₂ | H | C=O | CB |
| FB | CF₃ | H | H | 4-methoxyphenyl | H | CH₃ | C=H | NHCO | H | C=O | CB |
| FC | CF₃ | H | H | 2-fluorophenyl | H | CH₃ | C=CH₂ | SO₂ | OCF₃ | C=O | CB |

TABLE I-continued

| | R¹ | R² | R³ | R⁴ | R⁵ | R⁶ | L¹ | L² | X | Y | Z |
|---|---|---|---|---|---|---|---|---|---|---|---|
| FD | CH₃ | H | H | 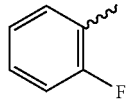 | H | CH₃ | C=CH₂ | SO₂ | OCF₃ | SO₂ | CB |
| FE | CF₃ | H | H | 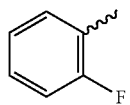 | H | CH₃ | C=O | SO₂ | OCF₃ | SO₂ | CB |
| FF | CH₃ | H | H | 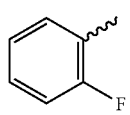 | H | CH₃ | C=NOH | SO₂ | OCF₃ | SO₂ | CB |
| FG | CH₃ | H | H | 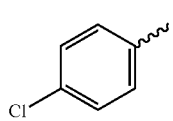 | H | CH₃ | C(CH₃)₂ | SO₂ | Cl | SO₂ | CB |
| FH | CF₃ | H | H | 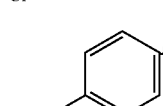 | H | H | C=O | SO₂ | OCH₃ | C=O | CB |
| FI | CH₃ | H | H | 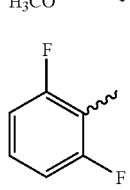 | H | H | O | SO₂ | Cl | SO₂ | CB |
| FJ | *R¹, Y, Z and R² combine to form morpholinyl | * | H | 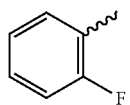 | — | O‖ | S | SO₂ | Cl | * | * |
| FK | H | CH₃ | H | 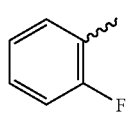 | — | O‖ | S=O | SO₂ | Cl | CB | CB |
| FL | H | CH₃ | H | 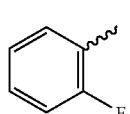 | — | O‖ | SO₂ | SO₂ | Cl | CB | CB |
| FM | *R¹, Y, Z and R² combine to form morpholinyl | * | H | 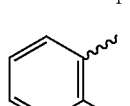 | — | O‖ | SO₂ | SO₂ | Cl | * | * |
| FN | CH₃ | CH₃ | H | 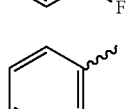 | — | O‖ | S | SO₂ | Cl | CB | CB |
| FO | H | H | H | 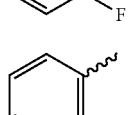 | — | O‖ | S | SO₂ | Cl | CB | CB |
| FP | CH₃ | CH₃ | H | 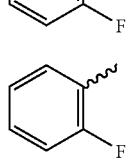 | — | O‖ | SO₂ | SO₂ | Cl | CB | CB |

TABLE I-continued

| | R¹ | R² | R³ | R⁴ | R⁵ | R⁶ | L¹ | L² | X | Y | Z |
|---|---|---|---|---|---|---|---|---|---|---|---|
| FQ | H | H | H | 2-F-phenyl | — | C=O | SO₂ | SO₂ | Cl | CB | CB |
| FR | CH₃ | H | H | 2,3-difluorophenyl | H | CH₃ | SO₂ | SO₂ | H | SO₂ | CB |
| FS | CH₃ | H | H | 2-F-phenyl | H | CH₃ | SO₂ | SO₂ | H | SO₂ | CB |
| FT | CH₃ | H | H | 2,5-difluorophenyl | H | CH₃ | SO₂ | SO₂ | H | SO₂ | CB |
| FU | CF₃ | H | H | 2-methylfuran-3-yl | H | CH₃ | SO₂ | SO₂ | H | C=O | CB |
| FV | CH₃ | H | H | thiophen-2-yl | H | CH₃ | SO₂ | SO₂ | H | SO₂ | CB |
| FW | CH₃ | H | H | 4-OCF₃-phenyl | H | CH₃ | SO₂ | SO₂ | H | SO₂ | CB |
| FX | CF₃ | H | H | CH₃ | H | CH₃ | SO₂ | SO₂ | H | C=O | CB |
| FY | CF₃ | H | H | 2-F-phenyl | H | CH₃ | SO₂ | SO₂ | H | SO₂ | CB |
| FZ | CF₃ | H | H | 2,3-difluorophenyl | H | CH₃ | SO₂ | SO₂ | H | SO₂ | CB |
| GA | CH₃ | H | H | 2-F-phenyl | H | CH₃ | CH₂ | SO₂ | OCF₃ | C=O | CB |

TABLE I-continued

| | R¹ | R² | R³ | R⁴ | R⁵ | R⁶ | L¹ | L² | X | Y | Z |
|---|---|---|---|---|---|---|---|---|---|---|---|
| GD | 4-OCF₃-phenyl | H | H | 2-F-phenyl | H | CH₃ | CH₂ | SO₂ | OCF₃ | SO₂ | CB |
| GF | NHC₂H₆ | H | H | 2-F-phenyl | H | CH₃ | CH₂ | SO₂ | OCF₃ | SO₂ | CB |
| GG | CF₃ | H | H | pyridyl | H | CH₃ | SO₂ | SO₂ | Cl | SO₂ | CB |
| GH | CF₃ | H | H | pyridyl | H | CH₃ | SO₂ | SO₂ | CF₃ | SO₂ | CB |
| GI | CF₃ | H | H | 4-OCH₃-2-F-phenyl | H | CH₃ | SO₂ | SO₂ | Cl | SO₂ | CB |
| GJ | CF₃ | H | H | 2-F-phenyl | H | CH₃ | SO₂ | SO₂ | OCH₃ | SO₂ | CB |
| GK | CF₃ | H | H | C(CH₃)₂(CF₃)O- | H | CH₃ | SO₂ | C=O | OCH₃ | SO₂ | CB |
| GL | CF₃ | H | H | 2-F-phenyl | H | CH₃ | SO₂ | SO₂ | OH | SO₂ | CB |
| GM | CF₃ | H | H | 2-F-phenyl | H | CH₃ | SO₂ | SO₂ | OCH(CH₃)₂ | SO₂ | CB |
| GN | CF₃ | H | H | 2-F-phenyl | H | CH₃ | SO₂ | SO₂ | cyclopropylmethoxy | SO₂ | CB |
| GO | CF₃ | H | H | pyridyl N-oxide | H | CH₃ | SO₂ | SO₂ | OCH₃ | C=O | CB |

CB is a covalent bond

— means that the substituent is not present

In a preferred embodiment, there are disclosed compounds of the formula

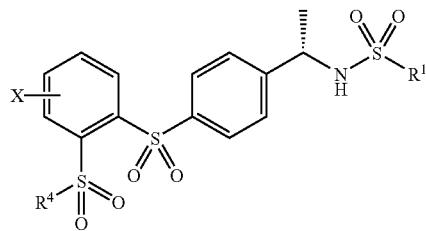

or a prodrug thereof, or a pharmaceutically acceptable salt or solvate of said compound or of said prodrug; wherein X, $R^1$ and $R^4$ are as shown in the table below:

| Example | X | $R^1$ | $R^4$ |
|---|---|---|---|
| A | $OCH_3$ | $CH_3$ | 2-F-phenyl |
| C | $OCF_2H$ | $CH_3$ | 2-F-phenyl |
| G | $CH_3$ | $CH_3$ | 2-F-phenyl |
| L | Cl | $CH_3$ | 2-F-phenyl |
| R | $CF_3$ | $CF_3$ | 2-F-phenyl |
| S | Cl | $CF_3$ | 2-F-phenyl |
| AB | $CF_3$ | $CH_3$ | 2-F-phenyl |
| AT | Cl | $N(CH_3)_2$ | 2-F-phenyl |
| BA | $OCF_3$ | $CH_3$ | 2-F-phenyl |
| BD | $OCF_3$ | $CF_3$ | 2-F-phenyl |
| BZ | $CH_3$ | $CF_3$ | 2-F-phenyl |
| CD | Cl | $CH_3$ | 2-F-phenyl |
| FS | H | $CH_3$ | 2-F-phenyl |
| FY | H | $CF_3$ | 2-F-phenyl |
| GG | Cl | $CF_3$ | 2-pyridyl |
| GH | $CF_3$ | $CF_3$ | 2-pyridyl |
| XXIX | cyclopropyl | $CF_3$ | 2-pyridyl |
| XXX | cyclopropyl | $CF_3$ | 2-F-phenyl |
| XXXI | cyclopropyl | $CF_3$ | 2-pyridyl N-oxide |
| XXXII | CN | $CF_3$ | 2-F-phenyl |
| XXXIII | $NH_2$ | $CF_3$ | 2-F-phenyl |
| XXXIV | cyclopropyl-NH-CH$_3$ | $CF_3$ | 2-F-phenyl |

-continued

| Example | X | R$^1$ | R$^4$ |
|---------|---|-------|-------|
| XXXVI | Cl | CF$_3$ | 2-methylpyridine N-oxide |
| XXXVII | isopropoxy | CF$_3$ | 2-methylpyridine |
| XXXVIII | CN | CF$_3$ | 2-methylpyridine |
| XXXIX | CONH$_2$ | CF$_3$ | 2-fluoro-6-methylphenyl |
| XXXX | OCH$_3$ | CF$_3$ | 2-fluoro-6-methylphenyl |
| XXXXI | OH | CF$_3$ | 2-fluoro-6-methylphenyl |
| XXXXII | isopropoxy | CF$_3$ | 2-fluoro-6-methylphenyl |
| XXXXIII | cyclopropylmethoxy | CF$_3$ | 2-fluoro-6-methylphenyl |
| XXXXIV | H$_3$C-CH$_2$-O-CH$_2$- | CF$_3$ | 2-fluoro-6-methylphenyl |
| XXXXV | H$_3$C-O-CH$_2$CH$_2$-O- | CF$_3$ | 2-fluoro-6-methylphenyl |
| LV | OCH$_3$ | CF$_3$ | 2-methylpyridine |
| LVI | cyclopropyl | CH$_3$ | 2-methylpyridine |

In another preferred embodiment, there are disclosed compounds of the formula or a prodrug thereof, or a pharmaceutically acceptable salt or solvate of said compound or of said prodrug; wherein X, Y—R$^1$ and R$^4$ are as shown in the table below:

| Example | X | Y—R$^1$ | R$^4$ |
|---------|---|---------|-------|
| XXXXVI | cyclopropyl | isopropyl (CH(CH$_3$)$_2$) | 2-methylpyridine |
| XXXXVII | cyclopropyl | cyclopentyl | 2-methylpyridine |
| XXXXVIII | cyclopropyl | cyclohexyl | 2-methylpyridine |
| XXXXIX | cyclopropyl | cyclopropylmethyl | 2-methylpyridine |
| VI | OCH$_3$ | isopropyl | 2-fluoro-6-methylphenyl |
| VII | OCH$_3$ | (3-methylthiophen-2-yl)methyl | 2-fluoro-6-methylphenyl |
| VIII | OCH$_3$ | benzyl | 2-fluoro-6-methylphenyl |

Compound A: $^1$H NMR (300 MHz, CDCl$_3$) 1.54 (d, j=6.9 Hz 3 H), 2.67 (s,3H), 4.72 (q,j=5 Hz 1H), 4.86 (br. d, j=5 Hz, 1H,NH), 7.08–8.42 (m, 11H).

Compound C: $^1$H NMR (400 MHz, CDCl$_3$) 1.51 (d, J=7.2 Hz 3H), 2.67 (s, 3H), 4.702 (q, J=6.8 Hz 1H), 5.05 (br. d, J=6.4 Hz, 1H, NH), 6.71 (t, J=71.6 Hz, CF2H) 7.07–8.47 (m, 11H).

Compound G: $^1$H NMR (300 MHz, CDCl$_3$) 8.43–8.41 (m, 1H), 8.36 (d, 8 Hz, 1H), 8.28–8.22 (m, 1H), 7.96–7.92 (m, 2H), 7.69–7.60 (m, 2H, 7.52–7.47 (m, 2H), 7.43–7.37 (m, 1H), 7.13–7.06 (m, 1H), 4.76–4.70 (m, 2H), 2.68 (s,3H), 2.59 (s, 3H), 1.41 (d, 7 Hz, 3H).

Compound L: $^1$H NMR (300 MHz, CDCl$_3$) 8.61–5.97 (m, 2H), 8.40 (d, 8 Hz, 1H), 8.24–8.21 (m, 1H), 7.96 (d, 8 Hz, 2H), 7.86–7.83 (m, 1H), 7.70–7.63 (m, 1H), 7.52 (d, 8 Hz, 2H), 7.46–7.40 (m, 1H), 7.18–7.12 (m, 1H), 4.80–4.70 (m, 1H), 2.71 (s, 3H), 1.56 (d, 7 Hz, 3H).

Compound R: $^1$H NMR (300 MHz, CDCl$_3$) 8.89–8.87 (m, 1H), 8.58 (d, 8 Hz, 1H), 8.32–8.25 (m, 1H), 8.15–8.11 (m, 1H), 8.03–7.98 (m, 2H), 7.71–7.63 (m, 1H), 7.52–7.48 (m, 2H), 7.47–7.41 (m, 1H), 7.16–7.09 (m, 1H), 5.62 (d, 8 Hz, 1H), 4.90–4.80 (m, 1H), 1.63 (d, 7 Hz, 3H).

Compound S: $^1$H NMR (300 MHz, CDCl$_3$) 8.61–8.59 (m, 1H), 8.39 (d, 8 Hz, 1H), 8.29–8.24 (m, 1H), 7.99 (d, 8 Hz, 2H), 7.86–7.82 (m, 1H), 7.67–7.62 (m, 1H), 7.49 (d, 8 Hz, 1H), 7.46–7.40 (m, 1H), 7.16–7.10 (m, 1H), 4.89–4.84 (m, 1H), 1.65 (d, 6 Hz, 1H).

Compound AB: $^1$H NMR (300 MHz, CDCl$_3$) 8.88–8.86 (m, 1H), 8.62–8.59 (m, 1H), 8.30–8.29 (m, 1H), 8.15–8.11 (m, 1H), 8.00–7.96 (m, 2H), 7.71–7.63 (m, 1H), 7.56–7.52 (m, 2H), 7.47–7.41 (m, 1H), 7.16–7.09 (m, 1H), 4.99–4.84 (m, 1H), 4.80–4.70 (m, 1H), 2.71 (s, 3H), 1.54 (d, 7 Hz, 3H).

Compound AT: $^1$H NMR (300 MHz, CDCl$_3$) 8.51 (br s 1H), 8.39 (d, 8 Hz, 2H), 7.99 (d, 8 Hz, 2H), 7.86–7.83 (m, 1H), 7.61–7.50 (m, 1H), 7.49 (d, 8 Hz), 7.05–6.99 (m, 1H), 4.70–4.50 (m, 2H), 2.83 (s, 3H), 2.57 (s, 3H), 1.50 (d, 7 Hz, 3H).

Compound BA: $^1$H NMR (300 MHz, CDCl$_3$) 1.54 (d, J=6.9 Hz 3H), 2.7 (s, 3H), 4.72 (q, J=5.5 Hz 1H), 5.05 (br. d, J=5 Hz 1H, NH), 7.1–8.55 (m, 11H).

Compound BD: $^1$H NMR (300 MHz, CDCl$_3$) 8.51 (d, 9 Hz, 1H), 8.47–8.45 (m, 1H), 8.01–7.97 (m, 2H), 7.71–7.63 (m, 2H), 7.52–7.41 (m, 3H), 7.17–7.10 (m, 1H), 5.51 (d, 8 Hz, 1H), 4.90–4.80 (m, 1H), 1.64 (d, 7 Hz, 3H).

Compound BZ: $^1$H NMR (300 MHz, CDCl$_3$) 8.43 (br s, 1H), 8.32 (d, 8 Hz, 1H), 8.28–8.22 (m, 1H), 7.94 (d, 8 Hz, 2H), 7.68–7.58 (m, 2H), 7.47–7.37 (m, 3H), 7.12–7.06 (m, 1H), 5.72 (d, 8 Hz, 1H), 4.86–4.70 (m, 1H), 2.59 (s, 3H), 1.60 (d, 7 Hz, 3H).

Compound CD: $^1$H NMR (300 MHz, CDCl$_3$): 8.82–8.78 (m, 1H), 8.23 (d, 7 Hz, 2H), 8.21–8.07 (m, 1H), 7.81–7.77 (m, 2H), 7.63–7.57 (m, 1H), 7.55 (d, 7 Hz, 2H), 7.40–7.32 (m, 1H), 7.20–7.16 (m, 1H), 4.8–4.7 (m, 2H), 2.67 (s, 3 H), 1.55 (d, 7 Hz, 2H).

Compound FS: $^1$H NMR (300 MHz, CDCl$_3$) 8.66–8.62 (m, 1H), 8.51–8.47 (m, 1H), 8.29–8.24 (m, 1H), 7.99–7.95 (m, 2H), 7.93–7.89 (m, 2H), 7.67–7.53 (m, 1H), 7.50–7.44 (m, 2H), 7.42–7.39 (m, 1H), 7.13–7.07 (m, 1H), 4.78–4.73 (m, 1H), 4.61–4.59 (m, 1H), 2.70 (s, 3H), 1.56 (d, 7 Hz, 3H).

Compound FY: $^1$H NMR (300 MHz, CDCl$_3$) 8.66–8.63 (m, 1H), 8.49–8.46 (m, 1H), 8.28–8.25 (m, 1H), 8.01 (d, 8 Hz, 2H), 7.93–7.89 (m, 2H), 7.65–7.58 (m, 1H), 7.56 (d, 8 Hz, 2H), 7.47–7.41 (m, 1H), 7.13–7.07 (m, 1H), 5.18 (d, 6 Hz, 1H), 4.90–4.80 (m, 1H), 1.66 (d, 7 Hz, 3H).

Compound GG: $^1$H NMR (300 MHz, CDCl$_3$): 8.88 (d, 1.2 Hz, 1H), 8.51–8.56 (m, 2H), 8.31 (dd, 8 Hz, 1 Hz, 1H), 8.18 (dd, 8 Hz, 1 Hz, 1H), 8.08–7.96 (m, 3H), 7.62–7.48 (m, 3H), 5.51 (d, 9 Hz, 1H), 4.90–4.70 (m, 1H), 1.62 (d, 7 Hz, 3H).

Compound GH: $^1$H NMR (300 MHz, CDCl$_3$): 8.63 (d, 2 Hz), 8.58–8.55 (m, 1H), 8.34–8.28 (m, 2H), 8.07–7.98 (m, 3H), 8.35 (dd, 8 Hz, 2 Hz, 1H, 7.55–7.46 (m, 3H), 5.34 (d, 8 Hz, 1H), 4.9–4.8 (m, 1 H), 1.64 (d, 6 Hz, 3H).

Compound GQ/XXIX: $^1$H NMR (300 MHz, CDCl$_3$): δ 8.56–8.52 (m, 1H), 8.32–8.21 (m, 3H), 8.02–7.92 (m, 4H), 5.42 (d, 9 Hz, 1H), 8.02–7.92 (m, 4H), 5.42 (d, 1H, 9 Hz), 4.84–4.78 (m, 1H), 2.16–2.06 (m, 1H), 1.60 (d, 7 Hz, 3H), 1.20–1.17 (m, 2H), 0.97–0.89 (m, 1H).

Compound GR/XXX: $^1$H NMR (300 MHz, CDCl$_3$): δ 8.33–8.22 (m, 3H), 8.00–7.94 (m, 2H), 7.66–7.58 (m, 1H), 7.53–7.37 (m, 4H), 7.16–7.05 (m, 1H), 5.160 (d, 9 Hz, 1H), 4.88–4.83 (m, 1H), 2.17–2.06 (m, 1H), 1.65 (d, 7 Hz, 3H), 1.28–1.20 (m, 2H), 0.97–0.90 (m, 2H).

Compound GS/XXXI: $^1$H NMR (300 MHz, CDCl$_3$): δ 8.38–8.29 (m, 2H), 8.17 (d, 8 Hz, 1H), 8.07–8.02 (m, 1H), 7.91–7.85 (m, 2H), 7.5614 7.36 (m, 5H), 6.11 (d, 8 Hz, 1H), 4.84–4.78 (m, 1H), 2.12–2.01 (m, 1H), 1.57 (d, 7 Hz, 3H), 1.21–1.12 (m, 2H), 0.92–0.86 (m, 2H).

Compound GW/XXXVI: $^1$H NMR (300 MHz, CDCl$_3$): δ 10.19 (d, 7.8 Hz, 1H), 8.27–8.42 (m, 4H), 8.13 (dd, 7.8 Hz, 2.1 Hz, 1H), 7.93 (d, 8.4 Hz, 2H), 7.78–7.63 (m, 2H), 7.59 (d, 8.4 Hz, 2H), 4.80 (m, 1H), 1.44 (d, 6.9 Hz, 3H).

Compound HO/XXXXXV: $^1$H NMR (300 MHz, CDCl$_3$): δ8.56 (d, 3.9 Hz, 1H), 8.31–8.22 (m, 2H), 8.124 (d, 2.7 Hz, 1H), 8.05–7.95 (m, 1H), 7.92 (d, 8.4 Hz, 2H), 0.750–7.45 (m, 1H), 7.92 (d, 8.4 Hz, 2H), 7.27–7.23 (m, 2H), 5.8 (d, NH, 1H), 4.85–4.75 (m, 1H), 3.99 (s, 3H), 1.58 (d, 7.2 Hz, 3H).

Compound HP/XXXXXVI: $^1$H NMR (300 MHz, CDCl$_3$): δ 8.56–8.52 (m, 1H), 8.31–8.23 (m, 3H), 8.02–7.90 (M, 4H), 4.87–4.78 (d, 7 Hz, 1H), 4.69 (m, 1 H), 2.66 (s, 3H), 2.16–2.06 (m, 1H), 1.51 (d, 7 Hz, 3H), 1.27–1.17 (m, 2H), 0.96–0.90 (m, 2H).

The compounds of the present invention exhibit anti-inflammatory and/or immunomodulatory activity and are useful in the treatment of various medical conditions including, e.g., rheumatoid arthritis, systemic lupus erythematosus, multiple sclerosis, glaucoma, diabetes, osteoporosis, renal ischemia, cerebral stroke, cerebral ischemia, nephritis, psoriasis, allergy, inflammatory disorders of the lungs and gastrointestinal tract such as Crohn's disease, and respiratory tract disorders such as reversible airway obstruction, asthma, chronic obstructive pulmonary disease (COPD) and bronchitis. This utility is manifested as demonstrated by activity in the following assay.

Potential cannabinoid receptor ligands were screened for the ability to compete with [$^3$H] CP-55,940 for binding to recombinant cannabinoid receptors. Test compounds were serially diluted in Diluent Buffer (50 mM Tris pH 7.1, 1 mM EDTA, 3 mM MgCl$_2$, 0.1% BSA, 10% DMSO, 0.36% methyl cellulose (Sigma M-6385)) from stocks prepared in 100% DMSO. Aliquots (10 ul) were transferred into 96-well microtiter plates. Membrane preparations of recombinant human cannabinoid CB2 receptor (Receptor Biology #RB-HCB2) or recombinant human cannabinoid CB1 receptor (Receptor Biology #RB-HCB1) were diluted to 0.3 mg/ml in Binding Buffer (50 mM Tris pH 7.2, 1 mM EDTA, 3 mM MgCl$_2$, 0.1% BSA). Aliquots (50 ul) were added to each well of the microtiter plate. The binding reactions were initiated by addition of [$^3$H] CP-55,940 (New England Nuclear# NET 1051; specific activity=180 Ci/mmol) to each well of the microtiter plate. Each 100 ul reaction mixture contained 0.48 nM [$^3$H] CP-55,940, 15 ug membrane protein in binding buffer containing 1% DMSO and 0.036% methyl cellulose. Following incubation for 2 hours at room temperature, the reactions were filtered through 0.5% polyethylenimine-coated GF/C filter plates (UniFilter-96, Packard) with a TomTec Mark 3U Harvester (Hamden, Conn.). The filter plate was washed 5 times with binding buffer, rotated 180°, then re-washed 5 times with binding buffer. Bound radioactivity was quantitated following addition of 30 ul of Packard Microscint 20 scintillant in a Packard TopCount NXT microplate scintillation counter. Non-linear regression analysis of the resulting data was performed using Prism 2.0b (GraphPad, San Diego, Calif.).

Cannabinoid receptor ligands according to the present invention have anti-inflammatory activity and/or immunomodulatory activity and are useful in the treatment of various medical conditions including, e.g., cutaneous T cell lymphoma, rheumatoid arthritis, systemic lupus erythematosus, multiple sclerosis, glaucoma, diabetes, osteoporosis, renal ischemia, myocardial infarction, cerebral stroke, cerebral ischemia, nephritis, hepatitis, glomerulonephritis, cryptogenic fibrosing aveolitis, psoriasis, atopic dermatitis, vasculitis, allergy, seasonal allergic rhinitis, Crohn's disease, inflammatory bowel disease, reversible airway obstruction, adult respiratory distress syndrome, asthma, chronic obstructive pulmonary disease (COPD) or bronchitis. It is contemplated that a compound of this invention may be useful in treating more than one of the diseases listed.

Additionally, one or more compounds of the present invention can be co-administered or used in combination with one or more disease-modifying antirheumatic drugs (DMARDS) such as methotrexate, azathioptrine leflunomide, pencillinamine, gold salts, mycophenolate mofetil, cyclophosphamide and other similar drugs. One or more compounds of the invention can also be co-administered with or used in combination with one or more NSAIDS such as piroxicam, naproxen, indomethacin, ibuprofen and the like; one or more COX-2 selective inhibitors such as VIOXX® and CELEBREX® ; one or more COX-1 inhibitors such as FELDENE® ; immunosuppressives such as steroids, cyclosporine, Tacrolimus, rapamycin and the like; biological response modifiers (BRMs) such as ENBREL®, REMICADE®, IL-1 antagonists, anti-CD40, anti-CD28, IL-10, anti-adhesion molecules and the like; and other anti-inflammatory agents such as p38 kinase inhibitors, PDE4 inhibitors, TACE inhibitors, chemokine receptor antagonists, Thalidomide and other small molecule inhibitors of pro-inflammatory cytokine production. Other drugs that the compounds of the invention can be co-administered or used in combination with include ANAPROX®, ARAVA®, ARTHROTEC®, AZULFIDINE®, Aspirin, CATAFLAM®, CELESTONE® SOLUSPAN®, CLINORIL®, CORTONE® Acetate, CUPRIMINE®, DAYPRO®, DECADRON®, DEPEN®, DEPEO-MEDROL®, DISALCID®, DOLOBID®, NAPROSYN®, GENGRAF®, HYDROCORTONE®, IMURAN®, INDOCIN®, LODINE®, MOTRIN ®, MYOCHYRISINE®, NALFON®, NAPRELAN®, INEORAL®, ORUDIS®, ORUVAIL®, PEDIAPRED®, PLAQUENIL®, PRELONE®, RELAFEN®, SOLU-MEDROL®, TOLECTIN®, TRILISATE® and/or VOLATAREN®. These include any formulation of the above named drugs.

For the treatment of multiple sclerosis, one or more compounds of the invention can be co-administered or used in combination with AVONEX®, BETASERON® and/or COPAXONE®.

For combination treatment with more than one active agent, where the active agents are in separate dosage formulations, the active agents can be administered separately or in conjunction. In addition, the administration of one element may be prior to, concurrent to, or subsequent to the administration of the other agents.

The present invention also relates to a pharmaceutical composition comprising one or more compounds of formula I and one or more pharmaceutically acceptable carriers. The compounds of formula I can be administered in any conventional dosage form known to those skilled in the art. Pharmaceutical compositions containing the compounds of formula I can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like. All routes of administration are contemplated including, but not limited to, parenteral, transdermal, subcutaneous, intramuscular, sublingual, inhalation, rectal and topical.

Thus, appropriate unit forms of administration include oral forms such as tablets, capsules, powders, cachets, granules and solutions or suspensions, sublingual and buccal forms of administration, aerosols, implants, subcutaneous, intramuscular, intravenous, intranasal, intraoccular or rectal forms of administration.

When a solid composition is prepared in the form of tablets, e.g., a wetting agent such as sodium lauryl sulfate can be added to micronized or non-micronized compounds of formula I and mixed with a pharmaceutical vehicle such as silica, gelatin starch, lactose, magnesium stearate, talc, gum arabic or the like. The tablets can be coated with sucrose, various polymers, or other appropriate substances. Tablets can be treated so as to have a prolonged or delayed activity and so as to release a predetermined amount of active principle continuously or at predetermined intervals, e.g., by using ionic resins and the like.

A preparation in the form of gelatin capsules may be obtained, e.g., by mixing the active principle with a diluent, such as a glycol or a glycerol ester, and incorporating the resulting mixture into soft or hard gelatin capsules.

A preparation in the form of a syrup or elixir can contain the active principle together, e.g., with a sweetener, methylparaben and propylparaben as antiseptics, flavoring agents and an appropriate color.

Water-dispersible powders or granules can contain the active principle mixed, e.g., with dispersants, wetting agents or suspending agents, such as polyvinylpyrrolidone, as well as with sweeteners and/or other flavoring agents.

Rectal administration may be provided by using suppositories which may be prepared, e.g., with binders melting at the rectal temperature, for example cocoa butter or polyethylene glycols.

Parenteral, intranasal or intraocular administration may be provided by using, e.g., aqueous suspensions, isotonic saline solutions or sterile and injectable solutions containing pharmacologically compatible dispersants and/or solubilizers, for example, propylene glycol or polyethylene glycol.

Thus, to prepare an aqueous solution for intravenous injection, it is possible to use a co-solvent, e.g., an alcohol such as ethanol or a glycol such as polyethylene glycol or propylene glycol, and a hydrophilic surfactant such as Tween® 80. An oily solution injectable intramuscularly can be prepared, e.g., by solubilizing the active principle with a triglyceride or a glycerol ester.

Topical administration can be provided by using, e.g., creams, ointments or gels.

Transdermal administration can be provided by using patches in the form of a multilaminate, or with a reservoir, containing the active principle and an appropriate solvent.

Administration by inhalation can be provided by using, e.g., an aerosol containing sorbitan trioleate or oleic acid, for example, together with trichlorofluoromethane, dichlorofluoromethane, dichlorotetrafluoroethane or any other biologically compatible propellant gas; it is also possible to use a system containing the active principle, by itself or associated with an excipient, in powder form.

The active principle can also be formulated as microcapsules or microspheres, e.g., liposomes, optionally with one or more carriers or additives.

Implants are among the prolonged release forms which can be used in the case of chronic treatments. They can be prepared in the form of an oily suspension or in the form of a suspension of microspheres in an isotonic medium.

The daily dose of a compound of formula I for treatment of a disease or condition cited above is about 0.001 to about 100 mg/kg of body weight per day, preferably about 0.001 to about 10 mg/kg. For an average body weight of 70 kg, the dosage level is therefore from about 0.1 to about 700 mg of drug per day, given in a single dose or 2–4 divided doses. The exact dose, however, is determined by the attending clinician and is dependent on the potency of the compound administered, the age, weight, condition and response of the patient.

EXAMPLE I

Compound 1

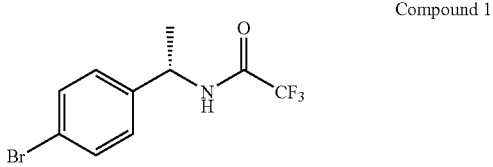

Compound 1. TFAA (67 mL, 0.474 mol) was dissolved in $CH_2Cl_2$ (300 mL) and cooled in an ice water bath. A solution of (S)-α-methylbenzylamine (56.4 g, 0.465 mol) dissolved in $CH_2Cl_2$ (100 mL) was added and the ice bath was removed. The reaction mixture was stirred at rt for 3 h. The reaction mixture was cooled in an ice bath and MsOH (80 mL, 1.23 mol) was added followed by DBDMH (65 g, 0.227 mol). The reaction mixture was left stirring overnight at rt then quenched with 1M aq $NaHSO_3$. The organic layer was washed with water and brine, dried with $MgSO_4$, and concentrated to give 130 g of white solid. The crude product was recrystallized from $Et_2O$ and hexanes giving 46 g (32%) of intermediate Compound 1 as a solid.

Compound 2

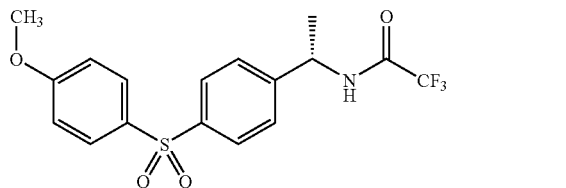

Compound 2. In a flame dried flask under $N_2$ blanket, Compound 1 (12.35 g, 41.2 mmol) was dissolved in dry THF (165 mL) and cooled to −78° C. Methyllithium (1.4 M in $Et_2O$, 30 mL, 42 mmol) was added and the reaction mixture was stirred for 5 min. n-BuLi (1.6 M in hexanes, 26 mL, 42 mmol) was added followed after 10 min by p-methoxybenzenesulfonyl fluoride (8.64 g, 45.4 mmol) which was prepared by standard methods. The cold bath was removed after 10 min and the reaction mixture was allowed to warm to rt over 45 min then quenched with pH 7 sodium phosphate buffer (1 M, 100 mL, 100 mmol). The reaction mixture was extracted with EtOAc and the resulting organic layer was washed with brine and dried with $MgSO_4$. After evaporation of the solvent, the crude product was purified by sgc (20%–50% EtOAc/hexanes gradient) to give 10.39 g (65%) of Compound 2 as a solid.

Compound 3

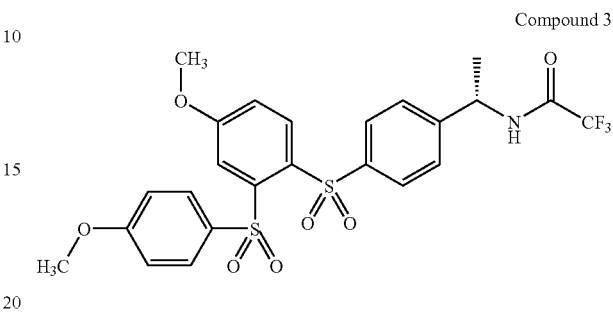

Compound 3. In a flame dried flask under $N_2$ blanket, Compound 2 (11.09 g, 28.6 mmol) was dissolved in anhyd THF (100 mL) and cooled to −78° C. A solution of n-BuLi (2.5 M in hexanes, 24 mL, 60 mmol) was added and the reaction mixture was stirred for 40 min. Bis-4-methoxyphenyl disulfide (8.76 g/31.5 mmol) was added and the reaction mixture was stirred at −78° C. for 40 min then between −15° C. and −30° C. for 5 h then quenched with pH 7.0 sodium phosphate buffer (1.0 M, 120 mL). The reaction mixture was partitioned between EtOAc and water. The aqueous layer was extracted with additional EtOAc. The combined organic layer was washed with aq $Na_2CO_3$ and brine, then dried with $MgSO_4$ and concentrated to dryness. The crude product (13.8 g yellow foam) was dissolved in $CH_2Cl_2$ (120 mL) and cooled to 0° C. MCPBA (18.5 g, ca 107 mmol) was added, followed by additional $CH_2Cl_2$ (40 mL). The ice bath was removed and the reaction mixture was stirred at rt for overnight. Aqueous $NaHCO_3$ (200 mL) and $CH_2Cl_2$ were added and the layers were separated. The organic layer was washed with aq $NaHSO_3$, $NaHCO_3$, $H_2O$, and brine then dried with $MgSO_4$. The crude product was purified by sgc (30% to 50% EtOAc/hexanes gradient) to give 7.21 g (45%) of Compound 3.

Compound 4

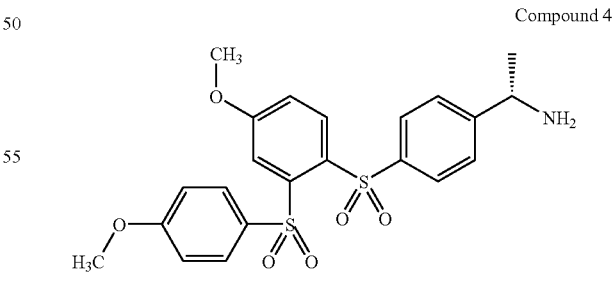

Compound 4. Compound 3 (4.47 g, 8.02 mmol) was dissolved in p-dioxane (16 mL) and cooled to 0° C. LiOH (1.0 M aq, 10 mL, 10 mmol) was added and the ice bath was removed. The reaction mixture was stirred at rt for 6 h then concentrated. $CH_2Cl_2$ (100 mL) and NaOH (1.0 M aq, 10 mL) were added and the layers were separated. The aqueous layer was extracted with additional CH$_2$Cl$_2$ and the combined organic layer was dried with MgSO$_4$ and concentrated. The crude product was purified by sgc (2%–10% MeOH (NH$_3$)/CH$_2$Cl$_2$ gradient mobile phase) to give 3.23 g (87%) of Compound 4.

Compound I

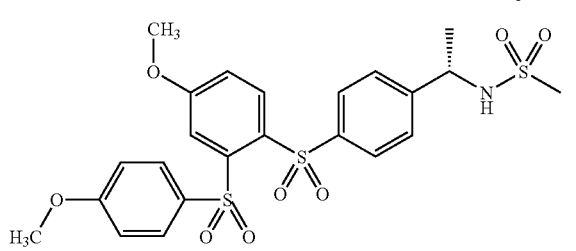

Compound I. Compound 4 (3.08 g, 6.67 mmol) was dissolved in CH$_2$Cl$_2$ (33 mL) and triethylamine (1.40 mL, 10.0 mmol) then cooled to 0° C. MsCl (569 µL, 7.34 mmol) was added and the reaction mixture was stirred at 0° C. for 1 h and 15 min. Citric acid (0.5 M, 40 mL) and additional CH$_2$Cl$_2$ were added and the layers were separated. The organic layer was washed with citric acid, NaHCO$_3$, and brine then dried with MgSO$_4$. The solvent was evaporated and the crude product was purified by sgc (40%–70% EtOAc/hexanes gradient) to give 3.44 g (96%) of Compound I as a solid.

Compound II

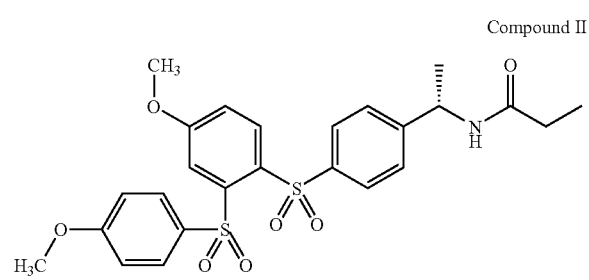

Compound II. Compound 4 (27.5 mg, 0.0595 mmol) was dissolved in methylene chloride (226 µL) and DIPEA (12 µL). A solution of propionyl chloride dissolved in 1,2-dichloroethane (1 M, 75 µL, 0.075 mmol) was added and the reaction mixture was shaken at room temperature overnight. Tris(2-aminoethyl)amine polystyrene (4.1 mmol N/g, ca 60 mg) was added to the reaction mixture. The reaction mixture was shaken for an additional hour at rt. The crude product was concentrated, then dissolved in EtOAc and filtered through a silica-gel SepPak (Waters Corp.). The resulting filtrate was concentrated to give 9 mg (29%) of Compound II.

Compound III

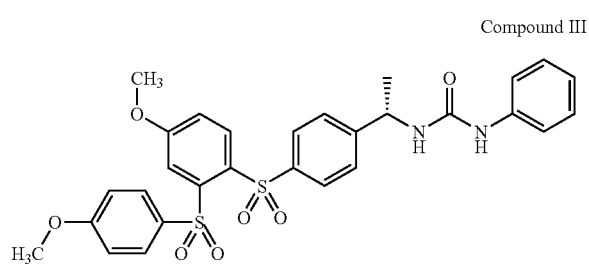

Compound III. Compound 4 (25 mg, 0.054 mmol) was dissolved in CH$_2$Cl$_2$ (270 µL). A solution of phenyl isocyanate dissolved in toluene (1.0 M, 65 mL, 0.065 mmol) was added and the reaction mixture was shaken at rt overnight. Tris (2-aminoethyl) amine polystyrene (4.1 mmol N/g, ca 60 mg) was added to the reaction mixture and the reaction mixture was shaken for an additional 40 min at rt. EtOAc was added and the reaction mixture was filtered through a silica gel SepPak (Waters Corp.). The resulting filtrate was concentrated to give 18 mg (57%) of Compound III.

EXAMPLE II

Compound 5

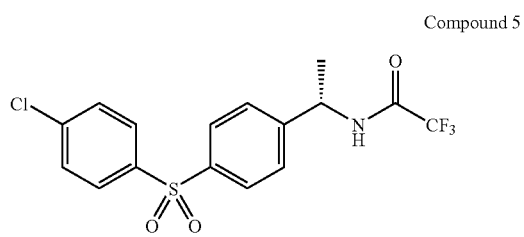

Compound 5. In a 3-necked flame-dried flask under N$_2$ blanket Compound 1 (40.0 g, 134 mmol) was dissolved in anhyd THF (535 mL) and cooled to −75° C. (internal temperature). A solution of methyllithium (1.4 M in diethyl ether, 105 mL, 147 mmol) was added at a rate that kept the internal temperature below −60° C. The reaction was stirred for 15 min and a solution of n-BuLi (2.5 M in hexanes, 62 mL, 155 mmol) was added at a rate that maintained the internal temperature of the reaction below −65° C. The reaction mixture was stirred for 40 min. and a solution of bis(4-chlorophenyl) disulfide (42 g, 146 mmol) dissolved in anhyd THF (90 mL) was added via addition funnel over 1 h. The reaction mixture was stirred for 3 h then quenched with HCl (1 M aqueous, 200 mL, 200 mmol). EtOAc (500 mL) was added and the layers were separated. The aqueous layer was extracted with 500 mL EtOAc, and the combined organic layer was washed with 1 M aq KOH, water, and brine. After drying with MgSO$_4$, the solvent was evaporated to give 54.1 g of a solid. The crude product (52.3 g) was dissolved in CH$_2$Cl$_2$ (750 mL) and cooled to 2° C. (internal temp). MCPBA (60%, 184 g) was added in portions over 1 hr and 20 min keeping the internal temperature below 15° C. The reaction mixture was stirred an additional 2 h. NaOH (1 M aq, 500 mL) and CH$_2$Cl$_2$ were added and the layers were separated. The aqueous layer was extracted with an additional 300 mL of CH$_2$Cl$_2$. The combined organic layer was washed with 1M aqueous NaOH, water, and brine, then dried with MgSO$_4$. After evaporation of the solvent, a solid (65 g) was obtained. The crude product was partially purified by trituration from Et$_2$O/hexanes to give 33.3 g of a solid which was subsequently purified via sgc (20%–25% EtOAc/hexanes) to give 30 g (57%) of Compound 5 as a solid.

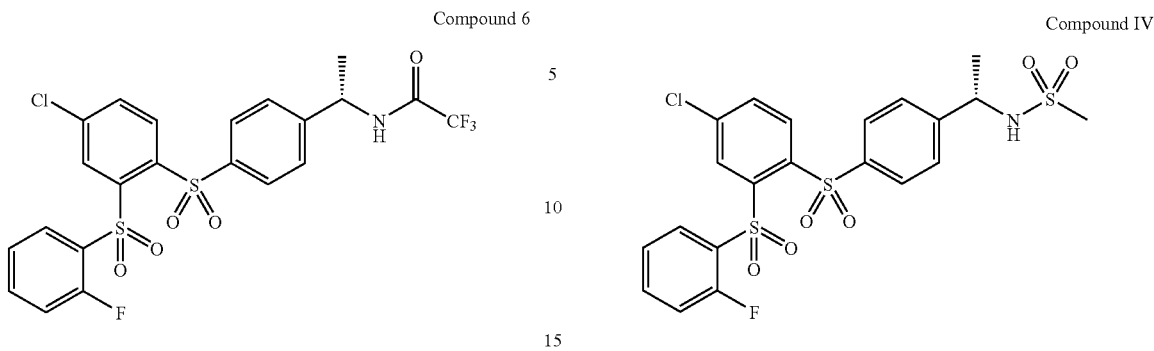

Compound 6.

Compound IV.

Compound 6. In a flame dried 3-necked flask under N₂ blanket Compound 5 (44 g, 112 mmol) was dissolved in anhyd THF (450 mL) and cooled in a dry ice/IPA bath. A solution of n-butyl lithium (2.5 M in hexanes, 92 mL, 230 mmol) was added at a rate that maintained the internal reaction temperature below −60° C., and the reaction mixture was stirred for 1 h. A solution of 2-fluorobenzenesulfonyl fluoride (22.3 g, 125 mmol) dissolved in anhyd THF (20 mL) was added and the reaction mixture was left stirring overnight and allowed to warm to rt. The reaction mixture was cooled to 0° C. and quenched with saturated aq ammonium chloride (300 mL). EtOAc (600 mL) and brine (25 mL) were added and the layers were separated. The organic layer was washed with water and brine, then dried with MgSO₄. The solvents were evaporated giving a foam (62 g). The product was purified by sgc (20%–25% EtOAc/hexanes mobile phase) giving 9.1 g (15%) of Compound 6.

Compound IV. Compound 7 (2.66 g, 5.86 mmol) was dissolved in CH₂Cl₂ (28 mL) and triethylamine (0.98 mL) and cooled to 0° C. MsCl (0.499 mL, 6.45 mmol) was added and the reaction mixture was stirred at 0° C. for 6 h. The reaction mixture was partitioned between water and CH₂Cl₂. The aqueous layer was extracted with additional CH₂Cl₂ and the combined organic layer was dried with MgSO₄. Evaporation of the solvent afforded 3.0 g of a foam which was purified by sgc (40%–50% EtOAc/hexanes gradient) to give 2.77 g (89%) of Compound IV.

Compound IV: ¹H NMR (300 MHz, CDCl₃) 8.61–5.97 (m, 2H), 8.40 (d, 8 Hz, 1H), 8.24–8.21 (m, 1H), 7.96 (d, 8 Hz, 2H), 7.86–7.83 (m, 1H), 7.70–7.63 (m, 1H), 7.52 (d, 8 Hz, 2H), 7.46–7.40 (m, 1H), 7.18–7.12 (m, 1H), 4.80–4.70 (m, 1H), 2.71 (s, 3H), 1.56 (d, 7 Hz, 3H).

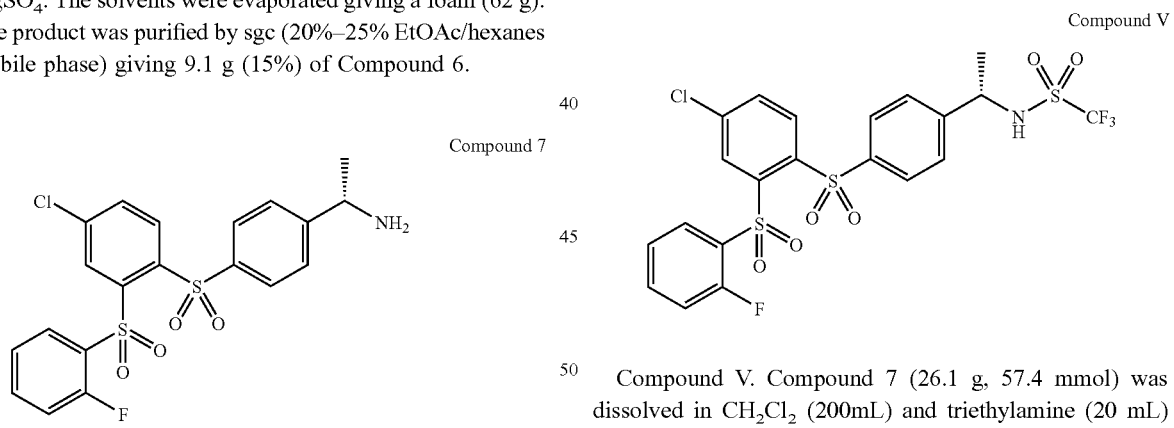

Compound 7.

Compound V.

Compound 7. Compound 6 (6.77 g, 12.3 mmol) was dissolved in dioxane (15 mL) and cooled in an ice bath. Aqueous lithium hydroxide (1 M, 15 mL, 15 mmol) was added and the reaction mixture was left stirring overnight. The reaction mixture was concentrated, then partitioned between CH₂Cl₂ and water. The aqueous layer was extracted with additional CH₂Cl₂ and the combined organic layer was dried with MgSO₄. Evaporation of the solvent afforded 5.66 g of a foam which was purified by sgc (10% MeOH (NH₃)/CH₂Cl₂) to give 4.27 g of Compound 7 (77%).

Compound V. Compound 7 (26.1 g, 57.4 mmol) was dissolved in CH₂Cl₂ (200mL) and triethylamine (20 mL) and cooled to −78° C. Triflic anhydride (10.45 mL, 62.1 mmol) was added and the reaction mixture was stirred for 3 h. The reaction was quenched with water and the layers were separated. The organic layer was washed with water and brine, then dried with MgSO₄. The solvent was evaporated to give 42 g of a foam. The crude product was purified via sgc (33%–50% EtOAc/hexanes gradient) to give 29.7 g (88%) of Compound V.

Compound V: ¹H NMR (300 MHz, CDCl₃) 8.61–8.59 (m, 1H), 8.39 (d, 8 Hz, 1H), 8.29–8.24 (m, 1H), 7.99 (d, 8 Hz, 2H), 7.86–7.82 (m, 1H), 7.67–7.62 (m, 1H), 7.49 (d, 8 Hz, 1H), 7.46–7.40 (m, 1H), 7.16–7.10 (m, 1H), 4.89–4.84 (m, 1H), 1.65 (d, 6 Hz, 1H).

Compound VI

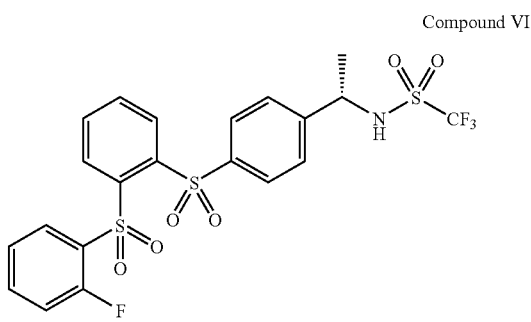

Compound VI. Compound V (300 mg, 0.512 mmol) was dissolved in methanol (60 mL). Sodium bicarbonate (720 mg, 8.57 mmol) and 5% palladium on carbon (480 mg) were added. The reaction mixture was shaken on a Parr apparatus under 52 psi of hydrogen gas overnight. The reaction mixture was filtered and the solvent was evaporated. The resulting material was partitioned between EtOAc and aq NaHCO$_3$. The organic layer was dried with MgSO$_4$ and the solvents were evaporated. The crude product was purified via sgc (33% EtOAc/hexanes) to give 257 mg (91%) of Compound VI.

EXAMPLE III

Compound 8

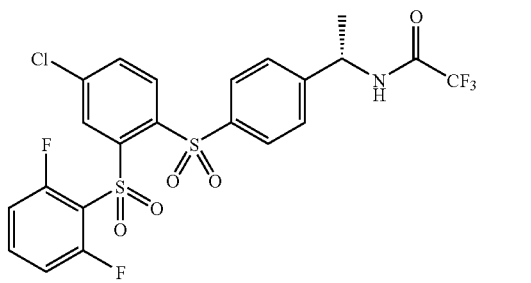

Compound 8. In a flame dried 3-necked flask under N$_2$ blanket Compound 5 (35.7 g, 91 mmol) was dissolved in anhyd THF (360 mL) and cooled in a dry ice/IPA bath. A solution of n-BuLi (2.5 M in hexanes, 76 mL, 190 mmol) was added at a rate that maintained the internal temperature below −60° C. The reaction mixture was stirred for 1 h. A solution of 2,6-difluorobenzenesulfonyl fluoride (19.47 g, 99.28 mmol) dissolved in anhyd THF (60 mL) was added. The reaction mixture was stirred for 2.5 h, then quenched with saturated aq NH$_4$Cl (400 mL). EtOAc (500 mL) was added and the layers were separated. The aq layer was extracted with EtOAc and the combined organic layer was washed with brine and dried with MgSO$_4$. The solvent was evaporated to give 60.7 g of an oil which was purified by sgc (15%–40% EtOAc/hexanes gradient) giving 14.4 g (28%) of Compound 8.

Compound 9

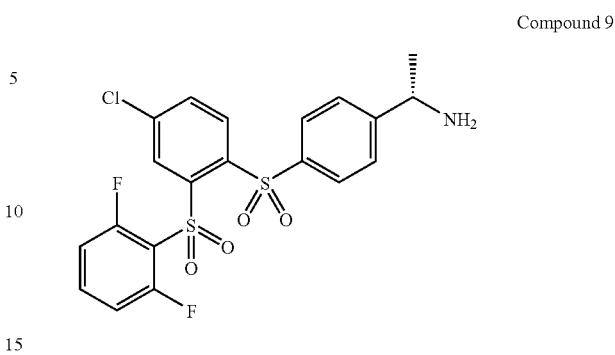

Compound 9. Compound 8 (21.1 g, 37.2 mmol) was dissolved in dioxane (47 mL) and aq lithium hydroxide (1.0 M, 41 mL, 41 mmol) was added. After 5.5 h, additional LiOH (20 mL) was added and the reaction mixture was stirred overnight. The reaction mixture was extracted with CH$_2$Cl$_2$, and partitioned between CH$_2$Cl$_2$ and water. The aq layer was extracted with additional CH$_2$Cl$_2$ and the combined organic layer was dried with MgSO$_4$. The solvents were evaporated to give 17.6 g of a foam and the crude product was purified by sgc (1%–3% MeOH (NH$_3$)/CH$_2$Cl$_2$ gradient) to give 12.2 g (69%) of Compound 9.

Compound VII

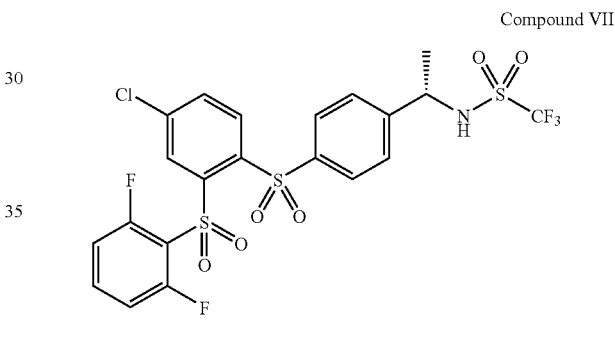

Compound VII. Compound 9 (10.7 g, 22.6 mmol) was dissolved in a mixture of CH$_2$Cl$_2$ (90 mL) and triethylamine (8 mL) and cooled to −78° C. Triflic anhydride (3.80 mL, 22.6 mmol) was added and the reaction mixture was stirred for 2 h. The reaction was quenched with saturated aq NaHCO$_3$ and the layers were separated. The aqueous layer was extracted with CH$_2$Cl$_2$. The combined organic layer was washed with brine and dried with MgSO$_4$. The solvents were evaporated and the crude product was purified by sgc to give 9.88 g (73%) of Compound VII.

EXAMPLE IV

Compound 5. In a flame dried flask under N$_2$ blanket Compound 1 (39.2 g, 132 mmol) was dissolved in anhyd THF (1 L) and cooled in a dry ice/acetone bath. A solution of methyllithium (1.6 M in Et$_2$O, 82.7 mL, 132 mmol) was added followed by a solution of n-BuLi (2.5 M in hexanes, 53 mL, 133 mmol). The reaction mixture was stirred for 25 min and a solution of bis(4-trifluoromethylphenyl) disulfide (46.9 g, 132 mmol) dissolved in THF (200 mL) was added. The reaction mixture was stirred for 2 h then allowed to warm to rt overnight. The reaction was quenched with water and concentrated. The resulting mixture was diluted with EtOAc, washed with water, and dried with Na$_2$SO$_4$. The solvent was evaporated and the crude product was purified via sgc (20% EtOAc/hexanes) to give 49.2 g (95%) of a solid. This material (49.2 g) was dissolved in CH$_2$Cl$_2$ (1.2 L)

and cooled in an ice bath. MCPBA (60%, 90 g) was added in small portions. After 1 h, the ice bath was removed and the reaction mixture was stirred overnight at rt. The reaction mixture was partitioned between $CH_2Cl_2$ and 10% aqueous $NaHCO_3$. The combined organic layer was washed with water and dried with $Na_2SO_4$. The solvent was evaporated and the crude product was purified by sgc (25% EtOAc/hexanes) to give 46.3 g (85%) of Compound 5.

Compound 10

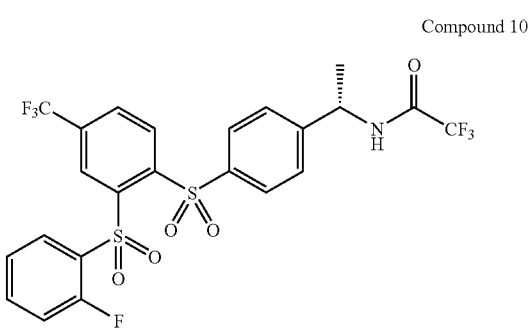

Compound 10. In a flame dried flask under $N_2$ blanket, Compound 5 (21.55 g, 50.7 mmol) was dissolved in anhyd THF (300 mL) and cooled in a dry ice/IPA bath. A solution of methyllithium (1.6 M in $Et_2O$, 32 mL, 51 mmol) was added, followed by n-BuLi (2.5 M in hexanes, 20.3 mL, 50.7 mmol) and the reaction mixture was stirred for 10 min. A solution of bis-(2-fluorophenyl) disulfide (14.2 g, 55.7 mmol) dissolved in THF was added and the reaction mixture was stirred for 2 h at −78° C. The ice bath was removed and the reaction mixture was allowed to warm to rt and left stirring overnight. The reaction mixture was quenched with saturated aqueous $NH_4Cl$ and extracted with EtOAc. The organic layer was dried with $Na_2SO_4$ and the solvents were evaporated. The crude product was purified via sgc (25% EtOAc/hexanes) to give 23.2 g of a solid. This material was dissolved in $CH_2Cl_2$ (400 mL) and cooled in an ice bath. MCPBA (60%, 30.3 g) was added in several portions and the reaction mixture was stirred for 1 h. The ice bath was removed and the reaction mixture was left stirring overnight. The reaction mixture was partitioned between $CH_2Cl_2$ and 5% aq $Na_2CO_3$. The organic layer was washed with water and dried with $Na_2SO_4$. The solvents were evaporated and the crude product was purified via sgc (25%EtOAc/hexanes) to give 10.84 g (44%) of Compound 10.

Compound 11

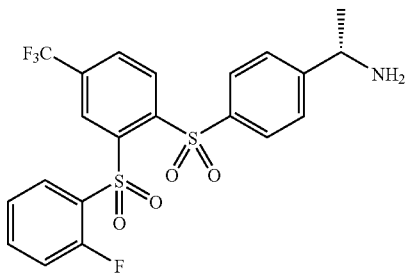

Compound 11. Compound 10 (11.88 g, 20.36 mmol) was dissolved in dioxane (200 mL) and aq lithium hydroxide (1.0 M, 400 mL) was added. The reaction mixture was stirred for 3 h then and partitioned between $CH_2Cl_2$ and water. The organic layer was dried with $Na_2SO_4$ and concentrated to give 9.34 g (99%) of Compound 11.

Compound VIII

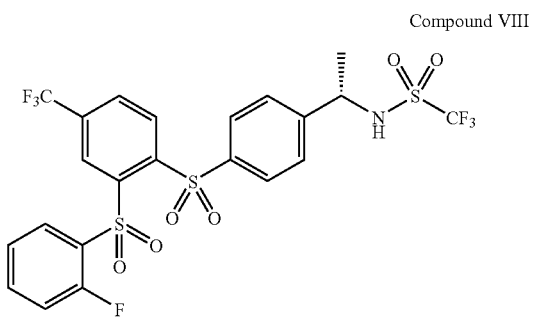

Compound VIII. Compound 11 (0.63 g, 1.29 mmol) was dissolved in a mixture of $CH_2Cl_2$ (60 mL) and triethylamine (0.27 mL) and cooled in an ice bath. Triflic. anhydride (0.55 g, 1.95 mmol) was added and the reaction mixture was stirred for 1 h. The ice bath was removed, and the reaction mixture was stirred an additional 3 h. The reaction was partitioned between water and $CH_2Cl_2$. The organic layer was washed with water and dried with $Na_2SO_4$. The solvent was evaporated and the crude product was purified by sgc (20% EtOAc/hexanes) to give 0.53 g (66%) of Compound VIII.

Compound VIII: $^1$H NMR (300 MHz, $CDCl_3$) 8.89–8.87 (m, 1H), 8.58 (d, 8 Hz, 1H), 8.32–8.25 (m, 1H), 8.15–8.11 (m, 1H), 8.03–7.98 (m, 2H), 7.71–7.63 (m, 1H), 7.52–7.48 (m, 2H), 7.47–7.41 (m, 1H), 7.16–7.09 (m, 1H), 5.62 (d, 8 Hz, 1 H), 4.90–4.80 (m, 1H), 1.63 (d, 7 Hz, 3H).

EXAMPLE V

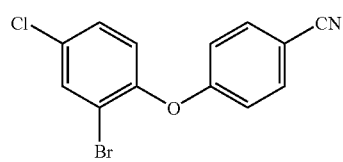

Potassium hydroxide (3.1 g, 55.2 mmol), 2-bromo-4-chlorophenol (9.52 g, 45.9 mmol), and 4-fluorobenzonitrile (5.73 g, 47.3 mmol) were added to DMA (25 mL) and the reaction mixture was stirred between 100° C. and 110° C. for one week. The reaction mixture was stirred at rt an additional two days. The solvents were partially removed on the rotary evaporator and the resulting mixture was partitioned between water and a 3:1 $Et_2O$/hexanes solution. The organic layer was washed with water and brine, then dried with $MgSO_4$. The solvents were evaporated and the crude product was purified by sgc (20%–30% $CH_2Cl_2$/hexanes) to give 11.96 g (81%) of an oil.

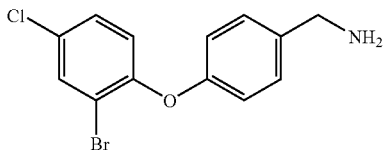

Compound 12

Compound 12. The product of the above step (5.90 g, 19.1 mmol) was placed under N₂ atmosphere and a solution of borane in THF (1.0 M, 21 mL, 21 mmol) was added causing an exotherm. Once the reaction mixture had returned to rt, it was heated to reflux and stirred at reflux overnight. Additional borane in THF (1.0 M, 20 mL, 20 mmol) was added and the reaction mixture was stirred at reflux for an additional 26 h then allowed to cool to rt. Water (55 mL) was added and the reaction mixture was partially concentrated. The resulting mixture was partitioned between EtOAc and aq NaOH (1.0 M). The organic layer was dried with MgSO₄ and concentrated to give 6.2 g of an oil. This material was dissolved in Et₂O and a solution of HCl in Et₂O was added causing Compound 12 (5.2 g, 78%) to precipitate as a solid.

Compound 13

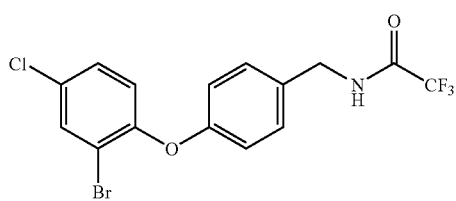

Compound 13. Compound 12 (5.13 g, 16.6 mmol) was suspended in a mixture of CH₂Cl₂ (40 mL) and triethylamine (7.5 mL). The mixture was cooled in an ice-water bath and TFAA (2.35 mL, 16.6 mmol) was added. The reaction mixture was stirred for 1 h and 20 min and the ice bath was removed. The reaction mixture was stirred for an additional 1 h and 20 min at rt. The reaction mixture was diluted with CH₂Cl₂ (100 mL) and washed with aq citric acid (0.5 M), saturated aq NaHCO₃, water, and brine, then dried with MgSO₄. The solvents were evaporated and the crude product (5.22 g) was purified via sgc (10%–20% EtOAc/hexanes gradient) to give Compound 13.

Compound 14

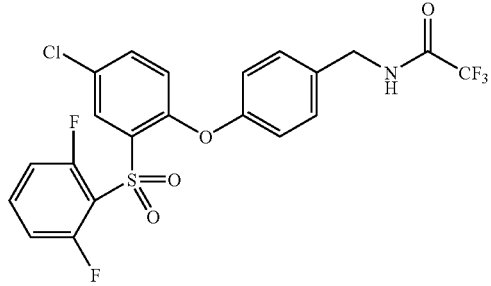

Compound 14. In a flame dried flask under N₂ blanket, Compound 13 (1.00 g, 2.47 mmol) was dissolved in anhyd THF (13 mL) and cooled in a dry ice/IPA bath. Methyllithium (1.4 M in Et₂O, 2.3 mL, 3.22 mmol) was added, followed by n-BuLi (2.5 M in hexanes, 1.3 mL, 3.25 mmol). The reaction mixture was stirred for 1 h at −78° C. A solution of 2,6-difluorobenzenesulfonyl fluoride (1.10 g, 5.60 mmol) dissolved in THF was added and the reaction mixture was stirred for 4 h. The reaction mixture was quenched with pH 7 sodium phosphate buffer (1.0 M) and EtOAc was added. The layers were separated and the aqueous layer was extracted with additional EtOAc. The combined organic layer was washed with brine and dried with MgSO₄. The solvents were evaporated and the crude product was purified via sgc (20%–33% EtOAc/hexanes) gradient to give 76 mg of Compound 14.

Compound 15

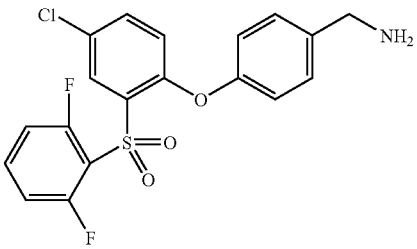

Compound 15. Compound 14 (59 mg, 0.12 mmol) was dissolved in 700 μL of dioxane and LiOH (1.0 M, 300 μL, 0.3 mmol) was added. The reaction mixture was stirred at rt for 24 h then partitioned between CH₂Cl₂ and 1.0 M aq NaOH. The organic layer was dried with MgSO₄ and concentrated. The crude product was purified via PTLC (Merck-silica plates, 3% (MeOH/NH₃)/CH₂Cl₂) to give the desired Compound 15. (21 mg, 45%).

Compound IX

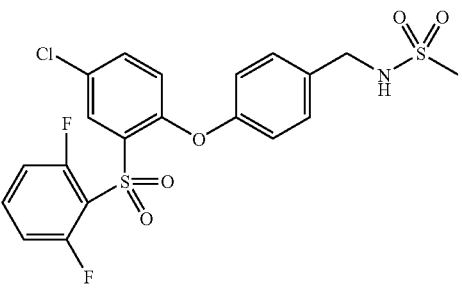

Compound IX. Compound 15 (17 mg, 0.042 mmol) was dissolved in CH₂Cl₂ (166 μL) and DIPEA (20 μL). The flask was cooled in an ice/water bath and MsCl (12 μL, 0.15 mmol) was added. The reaction mixture was stirred at 0° C. for 1 h and 30 min. The resulting mixture was partitioned between water and CH₂Cl₂. The organic layer was washed with water and brine, then dried with MgSO₄. The crude product was purified via PTLC (50% EtOAc/hexanes) to give 10 mg (50%) Compound IX.

EXAMPLE VI

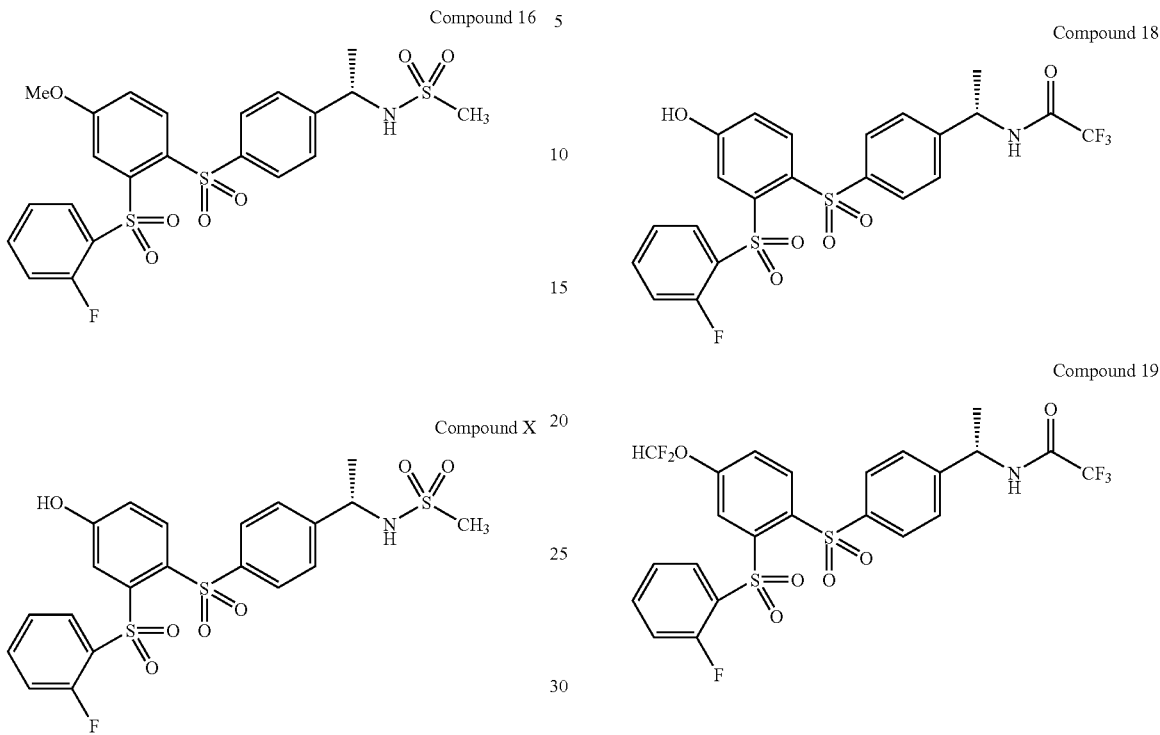

Compound 16 (0.116 g, 0.22 mmoles) was dissolved in CH$_2$Cl$_2$ (4 mL) and cooled to 0° C. BBr$_3$ solution (1.0 M in CH$_2$Cl$_2$, 0.66 mL) was added and the ice bath was removed. The reaction mixture was stirred at rt for 48 h and then quenched with water at −78° C. The reaction mixture was diluted with CH$_2$Cl$_2$ and the resulting organic layer was washed with aqueous NaHCO$_3$, H$_2$O (3×5 mL), and brine. The organics were dried over Na$_2$SO$_4$ and the solvent was removed under vacuum to give 0.09 g of crude product. The product was isolated by PTLC (5% CH$_3$OH/CH$_2$Cl$_2$) to provide Compound X (0.01 g, 8.8%).

Compound 16: $^1$H NMR (300 MHz, CDCl$_3$) 1.54 (d, J=6.9 Hz 3H), 2.67 (s, 3H), 4.72 (q, J=5 Hz 1H), 4.86 (br. d, J=5 Hz, 1H, NH), 7.08–8.42 (m, 11H).

EXAMPLE VII

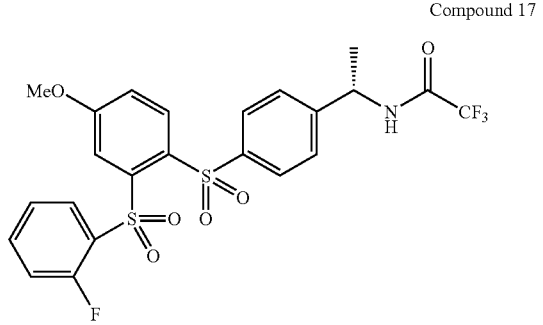

Compound 17 was converted to Compound 18 using the procedure in example VI.

Compound 18 (0.34 g, 0.64 mmoles) was dissolved in DMF (11 mL), cesium carbonate (0.84 g, 2.58 mmol) was added and the reaction mixture was cooled to 15° C. Dry bromodifluoromethane gas was introduced into the solution and bubbled for 15–20 min. Progress of the reaction was monitored by TLC and upon completion the reaction mixture was diluted with EtOAc (20 mL), washed with water (4×10 mL), and brine. The organics were dried over Na$_2$SO$_4$ and concentrated under reduced pressure to give 0.36 g of an oil. The crude product was purified by PTLC (50% EtOAc/hexanes) to provide 0.31 g (83%) of Compound 19.

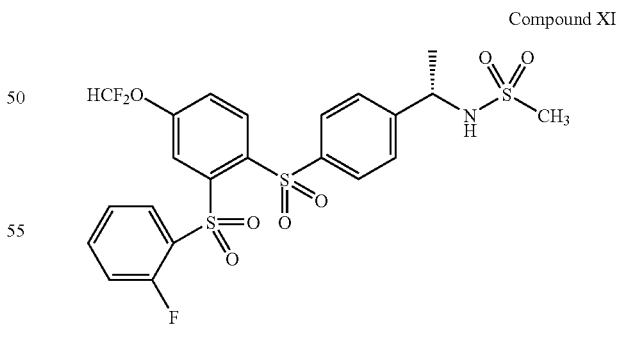

Compound 19 was converted to Compound XI using the procedure in example II.

Compound XI: $^1$H NMR (400 MHz, CDCl$_3$) 1.51 (d, J=7.2 Hz 3H), 2.67 (s, 3H), 4.702 (q, J=6.8 Hz 1H), 5.05 (br. d, J=6.4 Hz, 1H, NH), 6.71 (t, J=71.6 Hz, CF2H) 7.07–8.47 (m, 11H).

EXAMPLE VIII

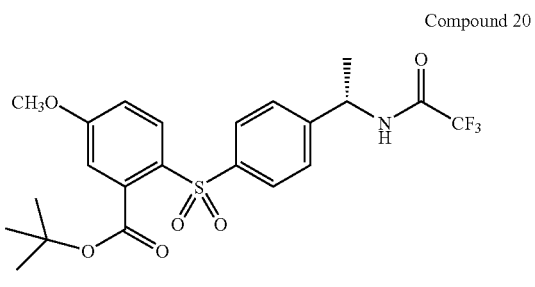

Compound 20

Compound 20. To a solution of Compound 2 (5.00 g, 12.9 mmol) in anhyd THF (75 mL) at −78° C. was added n-BuLi (13 mL, 2.5 M in hexanes, 32 mmol) dropwise over 10 min. The reaction mixture was stirred for 30 min. A solution of di-t-butyl dicarbonate (3.10 g, 14.2 mmol) in anhyd THF (25 mL) was added in one portion via cannula. The reaction was allowed to proceed for 4 h at −78° C. The reaction mixture was then diluted with EtOAc (~250 mL) and washed successively with saturated aq NaHSO₄ (~100 mL), water (~100 mL), and brine (~100 mL). The organic layer was dried over anhyd MgSO₄, filtered, and concentrated under reduced pressure to yield a solid. Further purification of the solid by sgc (25% EtOAc/hexanes) gave 5.32 g (84%) of Compound 20 as a solid.

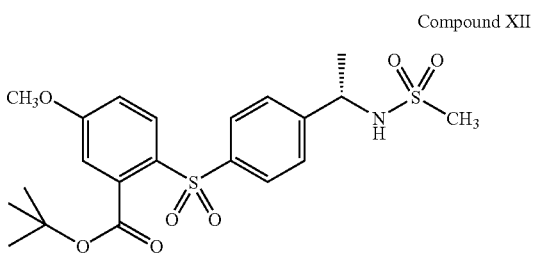

Compound XII

Compound XII. Compound 20 (2.06 g, 4.23 mmol) was dissolved in methanol (40 mL) and a solution of potassium carbonate (2.92 g, 21.1 mmol) in water (10 mL) was added. The reaction was allowed to proceed for 18 h. The solvent was then removed by evaporation under reduced pressure. The resulting white solid was partitioned between water (~100 mL) and EtOAc (~400 mL). The aqueous layer was extracted further with EtOAc (~100 mL). The combined organic layers were washed with brine (~500 mL), then dried over anhyd MgSO₄ and filtered. Evaporation of the solvent gave 1.22 g (74%) of t-butyl 2-[(4-(1(S)-aminoethyl) phenyl]sulfonyl-5-methoxybenzoate, an oil, which was used in the next step without further purification. MsCl (242 µL, 357 mg, 3.12 mmol) was added dropwise to a solution of crude t-butyl 2-[(4-(1(S)-aminoethyl)phenyl]sulfonyl-5-methoxybenzoate (1.22 g, 3.12 mmol) and triethylamine (522 µL, 379 mg, 3.75 mmol) in anhyd CH₂Cl₂ (3.0 mL) at 0° C. The reaction mixture was stirred at 0° C. for 5 min, then allowed to warm to rt, and subsequently stirred for 3 h. The reaction mixture was diluted with CH₂Cl₂ (~50 mL) and washed successively with 1 M HCl (~50 mL), water (3×~50 mL) and brine (~50 mL). The organic solution was dried over anhyd MgSO₄, filtered, and concentrated to yield a solid. Subsequent purification of the crude product by sgc (25% EtOAc/hexanes) gave 1.41 g (96%) of Compound XII as a solid.

EXAMPLE IX

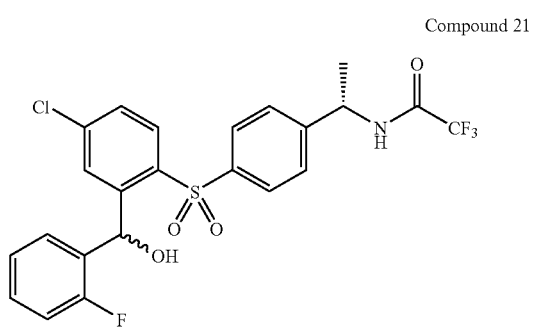

Compound 21

Compound 21. In a flame dried flask under N₂ blanket, Compound 5 (400 mg, 1.0 mmol) was dissolved in dry THF (5 mL) and cooled to −78° C. A solution of n-BuLi (1.0 M in hexanes, 1.9 mL, 1.9 mmol) was added and the reaction mixture was stirred for 30 min. 2-Fluorobenzaldehyde (200 mg, 1.6 mmol) was added and the reaction mixture was stirred at −78° C. for 3 h. The reaction mixture was then quenched with saturated aq NH₄Cl (20 mL). Methylene chloride (30 mL) was added and the layers were separated. The organic layer was washed with brine, then dried over Na₂SO₄, and concentrated to dryness. The crude product was purified via sgc (25% EtOAc/hexanes) to give 330 mg (62%) of Compound 21 as a powder.

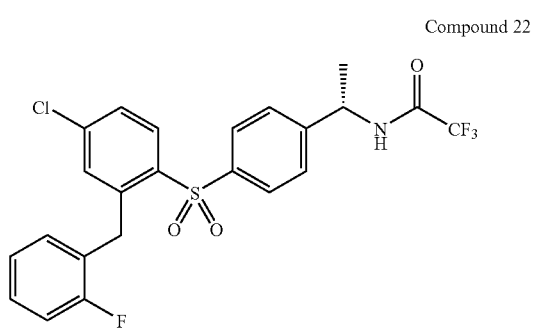

Compound 22

Compound 22. Compound 21 (10 mg) was dissolved in CH₂Cl₂ (10 mL). Triethylsilane (40 µL, 0.25 mmol) was added followed by BF₃.Et₂O (20 µL, 0.16 mmol). The reaction mixture was stirred at rt overnight. After removing the solvent, the crude product was purified via PTLC (25% EtOAc/hexanes) to give 6.0 mg (62%) Compound 22 as an oil.

via sgc (33% EtOAc/hexanes) to give 310 mg (94%) of Compound 23 as a powder.

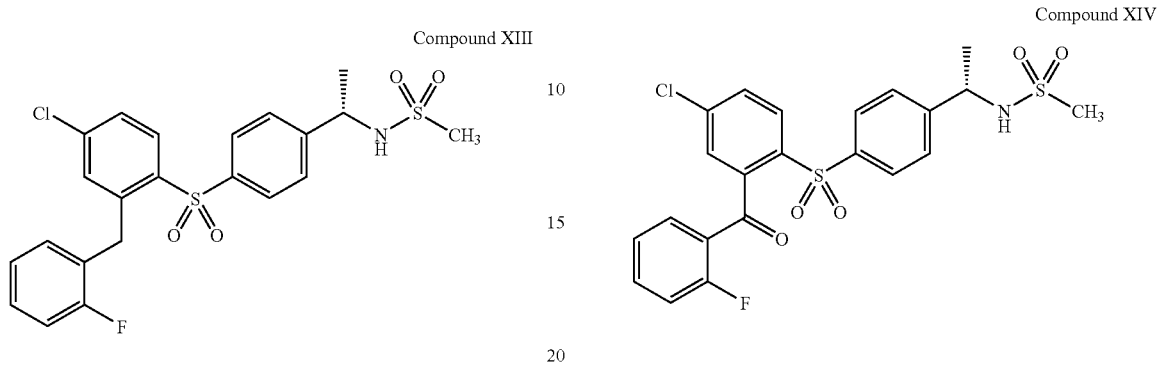

Compound XIII

Compound XIV

Compound XIII. Compound 22 (12 mg) was dissolved in methanol (2 mL) at rt. NaOH (1.0 M, 2 mL, 2.0 mmol) was added and the mixture was stirred at rt for 2 h. The solvent was removed, $CH_2Cl_2$ (15 mL) and brine (15 mL) were added, and the layers were separated. The aqueous layer was extracted with additional $CH_2Cl_2$ (15 mL) and the combined organic layers were dried over $Na_2SO_4$ and concentrated to dryness. The crude product was then dissolved in $CH_2Cl_2$ (10 mL) and cooled to 0° C. MsCl (14 μL, 0.18 mmol) was added followed by addition of pyridine (30 μL, 0.37 mmol). The reaction mixture was slowly warmed to rt and stirred overnight. Brine (15 mL) was added and extracted. The organic layer was dried over $Na_2SO_4$ and concentrated to dryness. The crude product was purified via PTLC (25% EtOAc/hexanes) to give 10 mg (86%) of Compound XIII as an oil.

Compound XIV. Compound 23 (15 mg) was dissolved in methanol (2 mL) at rt. NaOH (1.0 M, 2 mL, 2.0 mmol) was added and the mixture was stirred at rt for 2 h. The solvent was removed and $CH_2Cl_2$ (15 mL) and brine (15 mL) were added and the layers separated. The aq layer was extracted with additional $CH_2Cl_2$ (15 mL) and the combined organic layer was dried over $Na_2SO_4$ and concentrated to dryness. The crude product was then dissolved in $CH_2Cl_2$ (10 mL) and cooled to 0° C. MsCl (15 μL, 0.19 mmol) was added followed by addition of pyridine (30 μL, 0.37 mmol). The reaction mixture was slowly warmed to rt and stirred overnight. Brine (15 mL) was added and extracted. The organic layer was dried over $Na_2SO_4$ and concentrated to dryness. The crude product was purified via PTLC (33% EtOAc/hexanes) to give 9 mg (62%) of Compound XIV as an oil.

EXAMPLE X

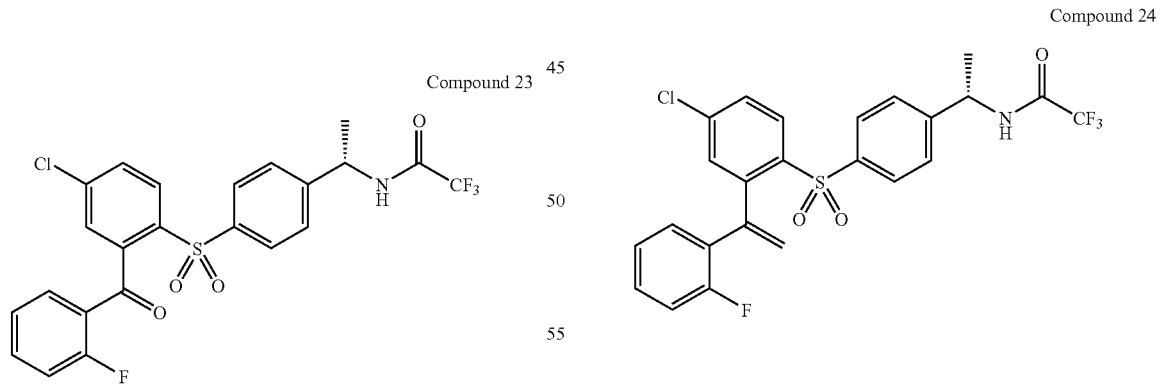

Compound 23

Compound 24

Compound 23. Compound 21 (330 mg, 0.64 mmol) was dissolved in $CH_2Cl_2$ (20 mL) at rt. Celite (450 mg) was added followed by addition of PCC (450 mg, 2.1 mmol). The mixture was stirred at rt overnight. The solid was removed by filtration and the organic layer was washed with aq. $NaHCO_3$ and brine. The organic layer was dried over $Na_2SO_4$ and concentrated to dryness. The crude product was purified Compound 24. Oven dried methyltriphenylphosphonium bromide (430 mg, 1.2 mmol) and LHDMS (1.0 M in hexanes, 1.8 mL, 1.8 mmol) were stirred in dry THF (5 ml) at 0° C. for 20 min., then warmed to rt and stirred for 10 min. A solution of Compound 23 (300 mg, 0.58 mmol) in THF (1 mL) was added dropwise. The mixture was stirred at rt overnight. EtOAc (20 ml) was added and the organic solution was washed with brine. The organic layer was dried over $Na_2SO_4$ and concentrated to dryness. The crude product was purified via PTLC (25% EtOAc/hexanes) to give 260 mg (87%) of Compound 24 as an oil.

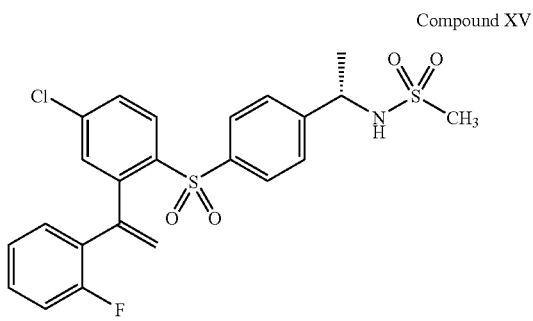

Compound XV

Compound XV. Compound 24 (200 mg, 0.39 mmol) was dissolved in methanol (3 mL) at rt. NaOH (1.0 M, 3 mL, 3.0 mmol) was added and the mixture was stirred at 50° C. for 2 h. The solvent was removed, $CH_2Cl_2$ (20 mL) and brine (20 mL) were added, and the layers were separated. The aqueous layer was extracted with additional $CH_2Cl_2$ (15 mL) and the combined organic layers were dried over $Na_2SO_4$ and concentrated to dryness. The crude product was then dissolved in $CH_2Cl_2$ (15 mL) and cooled to 0° C. MsCl (200 µL, 2.5 mmol) was added followed by addition of pyridine (400 µL, 4.9 mmol). The reaction mixture was slowly warmed to rt and stirred overnight. Brine (15 mL) was added and the organic layer separated, dried over $Na_2SO_4$ and concentrated to dryness. The crude product was purified via PTLC (50% EtOAc/hexanes) to give 160 mg (82%) of Compound XV as an oil.

EXAMPLE XI

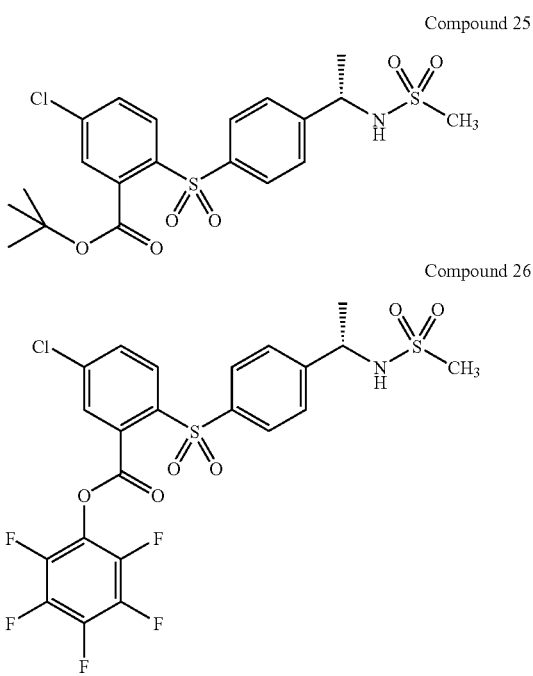

Compound 25

Compound 26

Compound 26. Compound 25 (1.3 g, 2.7 mmol) was stirred at rt with a mixture of $CH_2Cl_2$/TFA (2:1, 30 mL) for 3 h. The reaction mixture was then poured into brine (40 mL). The layers were separated. The aq layer was extracted with $CH_2Cl_2$ (3×30 mL) and the combined organic layers were dried over $Na_2SO_4$ and concentrated to dryness. The crude product was dissolved in $CH_2Cl_2$ (30 mL). EDCl (0.75 g, 3.9 mmol) and pentafluorophenol (0.73 g, 4.0 mmol) were added and the mixture was stirred at rt overnight. The reaction mixture was extracted with diluted aq NaOH and washed with brine. The organic layer was then dried over $Na_2SO_4$ and concentrated to dryness. The crude product was purified via sgc (33% EtOAc/hexanes) to give 1.15 g (72%) of Compound 26 as a foam.

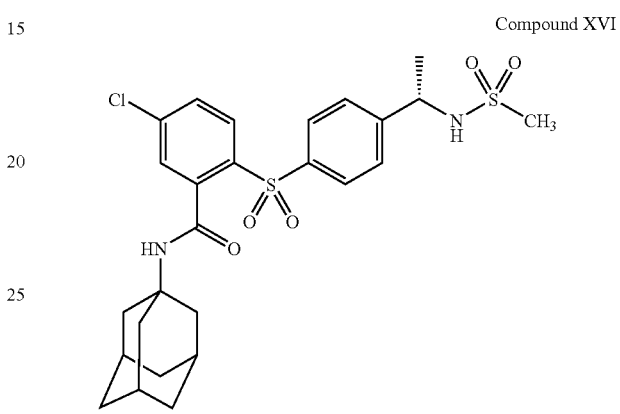

Compound XVI

Compound XVI. Compound 26 (50 mg) was dissolved in $CH_2Cl_2$ (2 mL). 1-Adamantanamine (21 mg, 0.14 mmol) was added followed by addition of DIPEA (0.05 mL, 0.29 mmol). The reaction mixture was shaken overnight. The reaction mixture was then subjected to Amberlyst 15 resin (300 mg, loading 4.1 mmol/g), and was again shaken overnight. The resin was removed by filtration. The filtrate was subjected to MP carbonate resin (Argonaut Technologies) (100 mg, loading 2.64 mmol/g) for 4 h. The resin was removed by filtration and the filtrate concentrated to give 33 mg (70%) of Compound XVI as a powder.

EXAMPLE XII

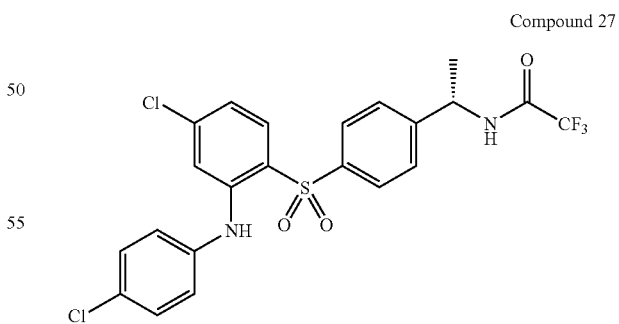

Compound 27

Compound 27. Compound 5 (500 mg, 1.3 mmol) was dissolved in dry THF (6 mL) at rt. NaH (53 mg, 60%, 1.3 mmol) was added, and the reaction mixture was stirred at rt for 1 h. The reaction mixture was then cooled to −78° C., and n-BuLi (1.0 M in hexanes, 1.5 mL, 1.5 mmol) was added dropwise under $N_2$ atmosphere. The reaction was stirred at −78° C. for 40 min. A solution of $I_2$ (390 mg, 1.5 mmol) in THF (2 mL) was added dropwise. The reaction mixture was stirred at −78° C. for 3 h, then quenched with saturated aq NH₄Cl (20 mL). EtOAc (30 mL) was added and the layers were separated. The organic layer was washed with brine, then dried over Na₂SO₄, and concentrated to dryness. The crude product (640 mg) was used without further purification. The crude product (60 mg) was dissolved in toluene (2 mL) and Pd(OAc)₂ (2 mg), P'Bu₃ (1 drop), NaO'Bu (14 mg, 0.15 mmol) and p-Chloroaniline (13 mg, 0.11 mmol) were added. The mixture was kept in a sealed tube and heated to 120° C. for 20 h. After cooling, methylene chloride (30 mL) and brine (20 mL) were added and the layers were separated. The organic layer was washed with brine, then dried over Na₂SO₄, and concentrated to dryness. The crude product was purified with via PTLC (20% EtOAc/hexanes) to give 18 mg (30%) of Compound 27 as a powder.

Compound XVII

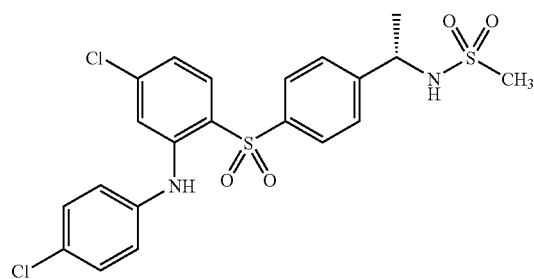

Compound XVII. Compound 27 (12 mg) was dissolved in methanol (2 mL) at rt. NaOH (1.0 M, 2 mL, 2.0 mmol) was added and the mixture was stirred at rt for 3 h. The solvent was removed, CH₂Cl₂ (20 mL) and brine (20 mL) were added, and the layers were separated. The aq layer was extracted with additional CH₂Cl₂ (15 mL) and the combined organic layers were dried over Na₂SO₄ and concentrated to dryness. The crude product was then dissolved in CH₂Cl₂ (15mL) and cooled to 0° C. MsCl (15 μL, 0.19 mmol) and pyridine (30 μL, 0.37 mmol) were added. The reaction mixture was slowly warmed up to rt and stirred overnight. Brine (15 mL) was added and the reaction mixture was extracted with CH₂Cl₂. The organic layer was dried over Na₂SO₄ and concentrated to dryness. The crude product was purified via PTLC (33% EtOAc/hexanes) to give 6.0 mg (52%) of Compound XVII as an oil.

Compound 28

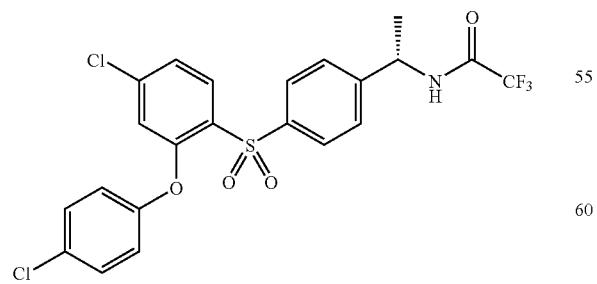

Compound 28. Compound 5 (500 mg, 1.3 mmol) was dissolved in dry THF (6 mL) at rt. NaH (53 mg, 60%, 1.3 mmol) was added, and the mixture was stirred at rt for 1 h. The reaction mixture was cooled to −78° C., and n-BuLi (1.0 M, 1.5 mL, 1.5 mmol) was added dropwise under N₂ atmosphere, and the temperature was maintained at −78° C. for 40 min. A solution of I₂ (390 mg, 1.5 mmol) in THF (2 mL) was added dropwise. The reaction was stirred at −78° C. for 3 h. The reaction mixture was quenched with saturated aq NH₄Cl (20 mL). EtOAc (30 mL) was added and the layers were separated. The organic layer was washed with brine, then dried over Na₂SO₄, and concentrated to dryness. The crude product (640 mg) was used without further purification. The crude product (60 mg) was dissolved in toluene (2 mL) and NaH (5 mg, 60%, 0.12 mmol), CuBr.Me₂S (34 mg, 0.17 mmol) and p-chlorophenol (15 mg, 0.12 mmol) were added. The reaction mixture was kept in a sealed tube and heated to 120° C. overnight. After cooling, CH₂Cl₂ (30 mL) and brine (20 mL) were added and the layers were separated. The organic layer was washed with brine, then dried over Na₂SO₄, and concentrated to dryness. The crude product was purified via PTLC (20% EtOAc/hexanes) to give 19 mg (31%) of Compound 28 as a powder.

Compound XVIII

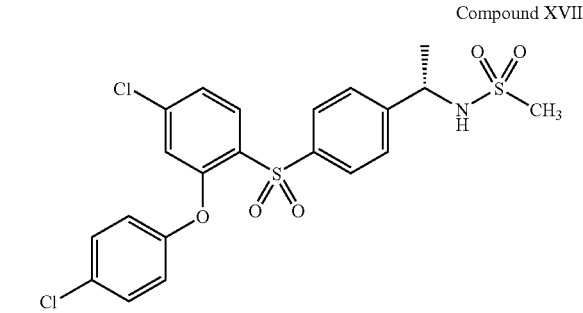

Compound XVIII. Compound 28 (15 mg, 29 μmol) was dissolved in methanol (2 mL) at rt. NaOH (1.0 M, 2 mL, 2.0 mmol) was added and the mixture was stirred at rt for 2 h. The solvent was removed and CH₂Cl₂ (20 mL) and brine (20 mL) was added and the layers were separated. The aq layer was extracted with additional CH₂Cl₂ (15 mL) and the combined organic layer was dried over Na₂SO₄ and concentrated to dryness. The crude product was then dissolved in CH₂Cl₂ (15 mL) and cooled to 0° C. MsCl (20 μL, 0.25 mmol) was added followed by addition of pyridine (20 μL, 0.25 mmol). The reaction mixture was slowly warmed up to rt and stirred overnight. Brine (15 mL) was added and extracted with CH₂Cl₂. The organic layer was dried over Na₂SO₄ and concentrated to dryness. The crude product was purified via PTLC (50% EtOAc/hexanes) to give 7.0 mg (48%) of Compound XVII as an oil.

EXAMPLE XIII

Compound 29

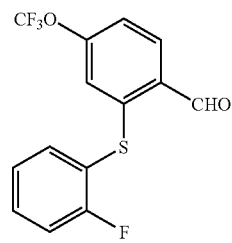

Compound 29. To a solution of N,N,N-Trimethylethylenediamine (1.2 mL, 8.6 mmol) in THF (8 mL) at −20° C. was added n-BuLi (1.6 M, 5.4 mL, 8.6 mmol) dropwise. After 15 min 4-trifluoromethoxybenzaldehyde (1.5 g, 7.8 mmol) in THF (8 mL) was added. The mixture was stirred for 15 minutes and additional n-BuLi (1.6M, 14.6 mL, 23 mmol) was added. The reaction mixture was stirred at −20° C. for 1 h, then placed in the freezer at −20° C. for 20 h. The mixture was cooled to −40° C, and a solution of bis(2-fluorophenyl)disulfide (4.0 g, 15.7 mmoles) in 30 mL THF was added. The reaction mixture was stirred at −35° C. for 3 h. The reaction mixture was poured into 0.5 N HCl and extracted with EtOAc. The organic layer was washed with water and brine, dried over Na₂SO₄, filtered and concentrated to an oil. Purification by sgc (3% EtOAc/hexanes) gave 1.55 g (62%) of Compound 29 as a solid.

Compound 30

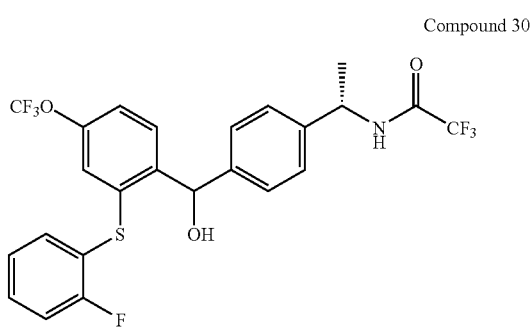

Compound 30. Methyllithium (3.25 mL, 5 mmol, 1.4 M ether) was added to a solution of Compound 1 (1.22 g, 4 mmol) at −70° C. After 10 min n-BuLi (1.6 M in hexanes, 2.83 mL, 5 mmol) was added and stirred for 30 min. A solution of Compound 29 (1.44 g, 4.55 mmoles), dissolved in THF (15 mL) was added. The resulting mixture was stirred at −70° C. for 2.5 h, quenched with water, warmed to 0° C. and then extracted with 2×50 mL EtOAc. The organic layer was washed with water, dried (Na₂SO₄), filtered and concentrated to an oil. Purification by sgc (EtOAc:hexanes) gave Compound 30 (1.4 g, 58%) as a gum.

Compound 31

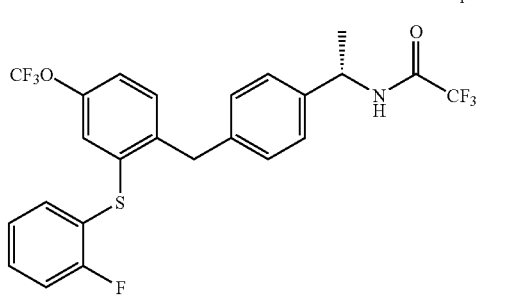

Compound 31. Triethylsilane (3.5 mL, 22.5 mmol) was added to a solution of Compound 30 (0.6 g, 1.125 mmol) in CH₂Cl₂ (30 mL), followed by addition of boron trifluoride etherate (0.32 mL, 1.94 mmol). After stirring at rt for 15 min the reaction mixture was diluted with 50 mL CH₂Cl₂, washed with water, dried over Na₂SO₄, filtered, and concentrated to give a solid. Purification via PTLC (25% EtOAc/hexanes (1:3) gave Compound 31 (0.47 g, 89%) as a solid.

Compound 32

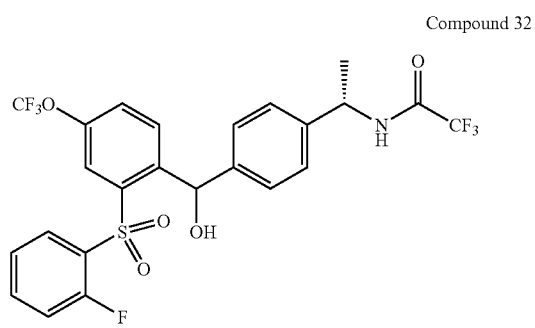

Compound 32. MCPBA (1.56 g (56%), 5.09 mmol) was added to a solution of Compound 31 (0.47 g, 0.9 mmol) in CH₂Cl₂ (30 mL) at rt. After stirring for 16 h the reaction was washed with 5% aq NaHSO₃, aq NaHCO₃, and water. The organics were dried over Na₂SO₄, filtered, and concentrated to give Compound 31 (0.4 g, 82%) as a solid.

Compound 33

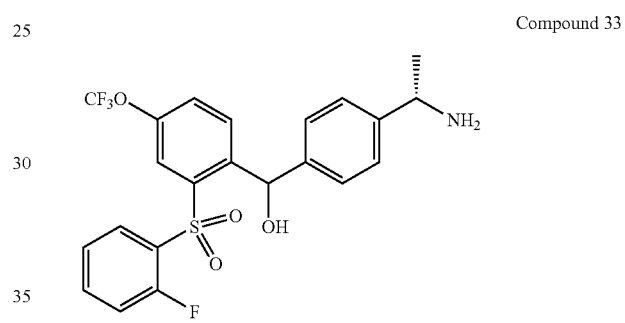

Compound 33. 1 M aq LiOH (9.7 mL, 9.7 mmol) was added to a solution of Compound 32 (1.78 g, 3.2 mmol) in 1,4-dioxane (15 mL). The resulting mixture was stirred overnight. The solvent was removed under reduced pressure and the residue was dissolved in 50 mL CH₂Cl₂ and washed with 10 mL brine. The organics were dried over Na₂SO₄, filtered and concentrated to an oil, which was used in the next step without additional purification.

Compound 34

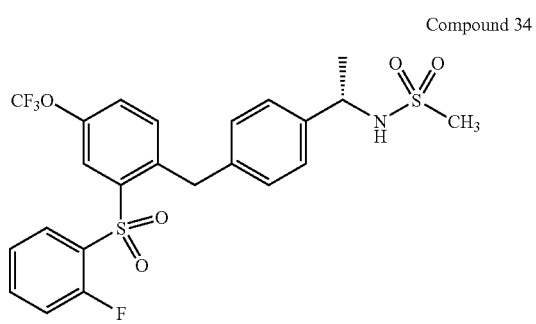

Compound 34. Triethylamine (0.28 mL, 2 mmol) was added to a solution of Compound 33 (0.18 g, 0.4 mmol) in CH₂Cl₂ at rt, followed by addition of MsCl (0.061 mL, 7.9 mmol ) in 0.2 mL CH₂Cl₂. The mixture was stirred overnight, then washed with 2×10 mL water, dried over Na₂SO₄, filtered, and concentrated to give an oil. The oil was purified via PTLC using EtOAc:hexanes (1:1) as the solvent to give Compound 34 (0.137g, 65%) as a solid.

Compound XIX

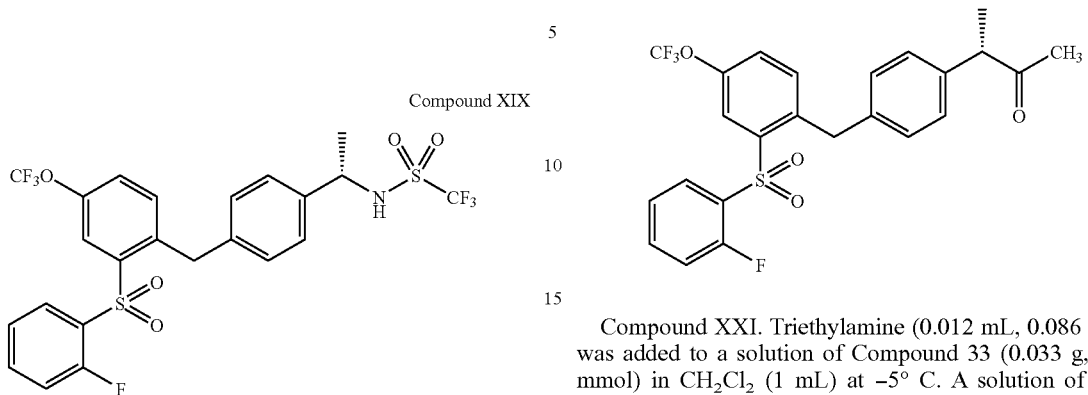

Compound XXI

Compound XIX. Triethylamine (0.296 mL, 2.1 mmol) was added to a solution of Compound 33 (0.4 g, 0.9 mmol) in 8 mL of CH$_2$Cl$_2$, cooled to 0° C., followed by addition of a solution of trifluoromethanesulfonic anhydride (0.54 g, 1.9 mmol) in CH$_2$Cl$_2$ (5 mL). The mixture was stirred at 0° C. for 3 h, washed with water, dried over Na$_2$SO$_4$, filtered, concentrated under reduced pressure to give crude Compound XIX. The crude product was purified via PTLC using 33% EtOAc:hexanes to give Compound XIX as a solid (0.32 g, 62%).

Compound XXI. Triethylamine (0.012 mL, 0.086 mmol) was added to a solution of Compound 33 (0.033 g, 0.073 mmol) in CH$_2$Cl$_2$ (1 mL) at −5° C. A solution of acetyl chloride (0.0057 mL, 0.08 mmol) in 0.5 mL CH$_2$Cl$_2$ was added. The mixture was stirred overnight at rt. The organics were washed with water, and then dried over Na$_2$SO$_4$, filtered, and then concentrated under reduced pressure. The resulting crude was purified by PTLC (EtOAc) to provide Compound XXI as a solid (0.009 g, 25%).

Compound XXII

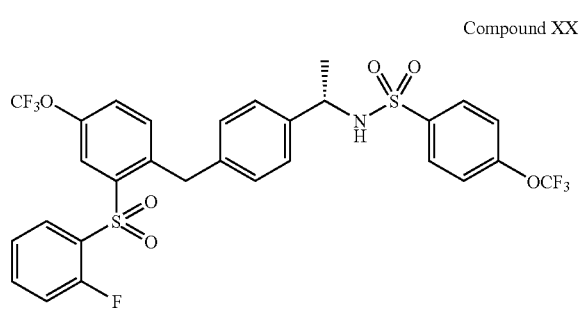

EXAMPLE XIV

Compound XX

Compound XXII. Cyclopentyl isocyanate (0.0135 g, 0.12 mmol) was added as a CH$_2$Cl$_2$ solution (0.5 mL) to a solution of Compound 33 (0.05 g, 0.11 mmol) in CH$_2$Cl$_2$ (1 mL). The reaction mixture was stirred at rt overnight. The solvent was removed under reduced pressure and the crude product was subjected to PTLC (EtOAc/hexanes 1:2) to provide Compound XXII (0.04 g, 65%).

EXAMPLE XV

Compound XX. Triethylamine (0.018 mL, 0.129 mmol) was added to a solution of Compound 33 (0.05 g, 0.11 mmol) in CH$_2$Cl$_2$ (1.5 mL) followed by addition of 4-(trifluoromethoxy)benzenesulfonyl chloride (0.02 mL, 0.118 mmol) in CH$_2$Cl$_2$ at rt. The stirring was continued for 10 h. The reaction mixture was diluted with 50 mL CH$_2$Cl$_2$, washed with water, dried over Na$_2$SO$_4$, filtered and concentrated under reduced pressure. The crude product was purified by PTLC (33% EtOAc:hexanes to give Compound XX as a solid (0.048 g, 65%).

Compound XXIII

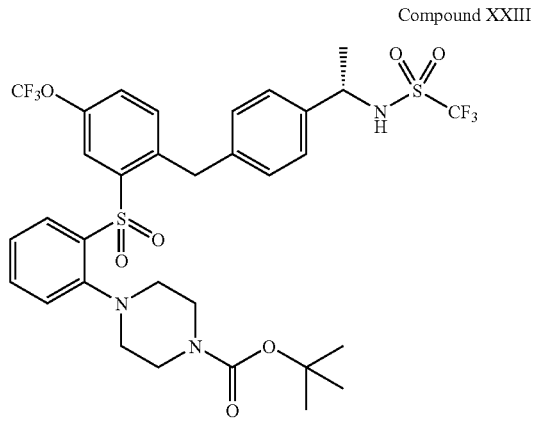

Compound XXIII. N-Boc-piperazine (0.5 g, 2.68 mmol) was added to a solution of Compound XIX (0.2 g, 0.34 mmol) in CH₃CN (10 mL). The reaction was heated at 80° C. for 72 h. Additional N-Boc-piperazine (0.25 g, 1.34 mmol) was added and heated at 80° C. for another 16 h. The solvent was removed under reduced pressure and the crude product was purified via PTLC (50% EtOAc:hexanes) to provide Compound XXIII as a solid, (0.096 g, 37%).

EXAMPLE XVI

Compound 35

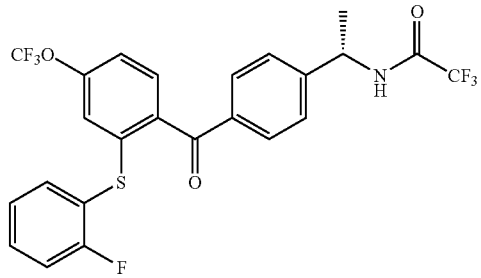

Compound 35. Pyridinium chlorochromate (0.194 g, 0.899 mmol) was added to a mixture of Compound 30 (0.4 g, 0.75 mmol) and Celite (0.4 g) in CH₂Cl₂ (10 mL) at rt. The mixture was stirred for 18 h, filtered through Celite and concentrated. The crude material was purified via PTLC using 33% EtOAc:hexanes to obtain Compound 35 (0.4 g, 100%).

Compound 36

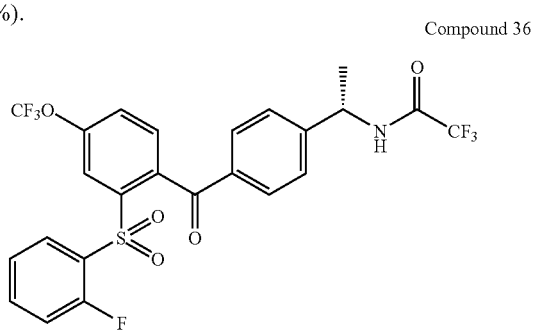

Compound 36. MCPBA (1.29 g (56%), 4.18 mmol) was added to a solution of Compound 35 (0.4 g, 0.75 mmol) in CH₂Cl₂ (20 mL) and stirred at rt for 18 h. The reaction was washed with 5% aq NaHSO₃, 5% NaHCO₃, and water. The organics were dried over Na₂SO₄, filtered and concentrated. The crude product was purified via PTLC using EtOAc:hexanes (1:1) to provide Compound 36 (0.34 g, 80%).

Compound 37

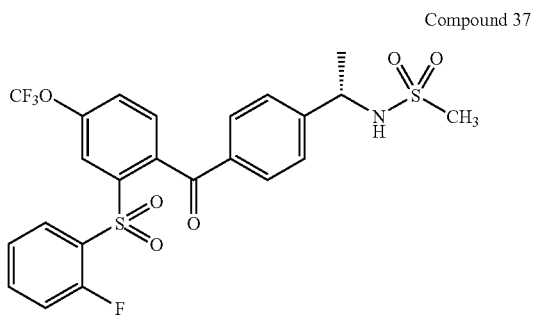

Compound 37. Compound 36 was converted to Compound 37 using a procedure similar to that described in example II.

Compound 38

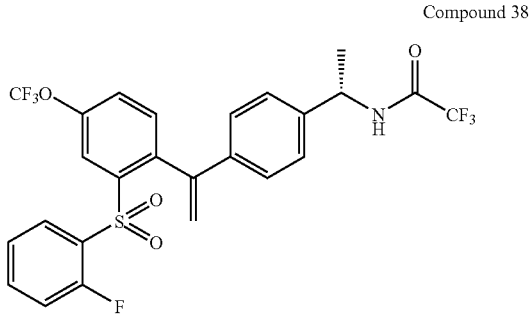

Compound 38. LHMDS (0.9 mL, 1M solution THF, 0.896 mmol) was added to a suspension of methyltriphenylphosphonium bromide (0.215 g, 0.6 mmol) in anhydrous THF (10 mL) at 0° C. The mixture was stirred at 0° C. for 20 min, then for 10 minutes at rt. A solution of Compound 36 (0.17 g, 0.3 mmol) in THF (8 mL) was added and stirring continued for 10 h at rt. The mixture was diluted with EtOAc and washed with water. The organics were dried over anhydrous Na₂SO₄, filtered and concentrated. The crude product was purified via PTLC using EtOAc:hexanes (1:3) to provide Compound 38 as a solid. (0.09 g, 54%).

Compound XXIV

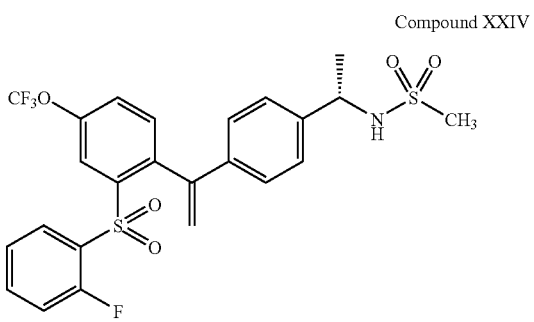

Compound XXIV. Compound 38 was converted to Compound XXIV using a procedure similar to that described in example II.

Compound XXV

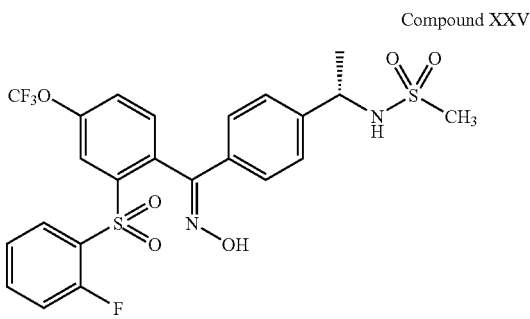

Compound XXV. Hydroxylamine hydrochloride (0.076 g, 1.09 mmol) was added to a solution of Compound 37 (0.03 g, 0.055 mmol) in pyridine (0.5 mL). The mixture was heated at 80° C. for 24 h. The mixture was cooled to rt and the solvent was removed under reduced pressure. The residue was dissolved in 50 mL CH$_2$Cl$_2$ and washed with water and brine. The organics were dried over Na$_2$SO$_4$, filtered and concentrated to provide crude Compound XXV, which was purified via PTLC (EtOAc/hexanes, 1:3) to afford Compound XXV as a solid (0.01 g, 33%).

Compound 40. Compound 39 (1.52 g, 2.70 mmol) was dissolved in dioxane (9 mL) and cooled to 0° C. LiOH (1.0 M aq, 3 mL, 3 mmol) was added and the reaction mixture was left stirring overnight, during which time it warmed to rt. The solvents were evaporated. CH$_2$Cl$_2$ and aq NaOH were added and the layers were separated. The aqueous layer was extracted with additional CH$_2$Cl$_2$ and the combined organic layer was dried with Na$_2$SO$_4$ and concentrated to give 0.85 g (68%) of Compound 40.

EXAMPLE XVII

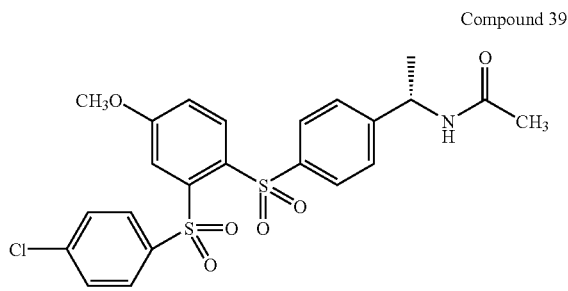

Compound 39

Compound 39. In a flame dried flask under N$_2$ blanket, Compound 2 (4.00 g, 10.32 mmol) was dissolved in anhyd THF (41 mL) and cooled to −78° C. A solution of n-BuLi (2.5 M in hexanes, 8.25 mL, 20.6 mmol) was added and the reaction mixture was stirred for 25 min. Bis-4-chlorophenyl disulfide (3.10 g/10.8 mmol) was added and the reaction mixture was stirred at −78° C. for 3 h then between −78° C. and −10° C. for 3 h. The reaction mixture was quenched with pH 7.0 sodium phosphate buffer (1.0 M, 50 mL). The reaction mixture was partitioned between EtOAc and water. The organic layer was washed with brine, then dried with Na$_2$SO$_4$ and concentrated to dryness. The crude product (5.44 g foam) was dissolved in CH$_2$Cl$_2$ (120 mL) and cooled to 0° C. MCPBA (7.24 g) was added. The ice bath was removed and the reaction mixture was stirred at rt overnight. Aqueous NaHCO$_3$ and CH$_2$Cl$_2$ were added and the layers were separated. The organic layer was washed with aq NaHSO$_3$, NaHCO$_3$, H$_2$O, and brine then dried with MgSO$_4$. The crude product was purified by sgc (35%–40% EtOAc/hexanes gradient) to give 1.86 g (32%) of Compound 39.

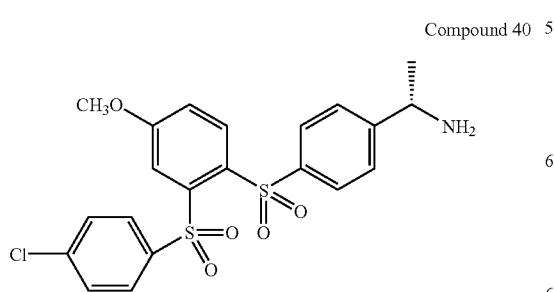

Compound 40

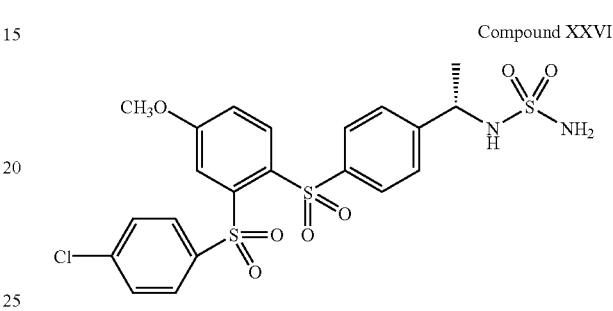

Compound XXVI

Compound XXVI. Compound 40 (143 mg, 0.307 mmol) was dissolved in dioxane and sulfamide (0.128, 1.33 mmol) was added. The reaction mixture was stirred at reflux for 24 h then allowed to cool to rt and concentrated. The reaction mixture was purified via PTLC (5% MeOH/CH$_2$Cl$_2$) giving 54 mg (32%) of Compound XXVI.

EXAMPLE XVIII

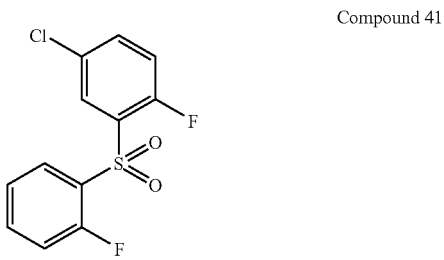

Compound 41

Compound 41. In a flame dried flask under N$_2$ blanket, 1-chloro-4-fluorobenzene (7.36 g, 56.4 mmol) was dissolved in anhyd THF and cooled in a dry ice/acetone bath. n-BuLi (2.5 M in hexanes, 22.5 mL, 56.3 mmol) was added and the reaction was stirred for 50 min. 2-Fluorobenzene sulfonyl fluoride (10.3 g, 57.8 mmol) was added and the reaction mixture was left stirring overnight, during which time it warmed to rt. Saturated aq NH$_4$Cl (100 mL) was added, followed by EtOAc (100 mL) and the layers were separated. The organic layer was washed with water and brine, then dried with MgSO$_4$. The solvents were evaporated and the crude product was purified via sgc (10% EtOAc/hexanes) to afford Compound 41 (2.55 g, 16%) as a solid.

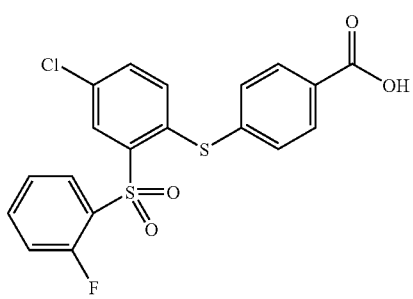

Compound 42

Compound 42. 4-Mercaptobenzoic acid (0.54 g, 3.50 mmol) was dissolved in DMA (10 mL) and cooled in an ice bath. Sodium hydride (60% suspension in oil, 0.30 g, 7.5 mmol) was added and the reaction mixture was stirred for 20 min. The ice bath was removed and the reaction mixture was stirred for 1 h. The flask was cooled to 0° C. again and compound 41 (1.0 g, 3.46 mmol) dissolved in DMA (5 mL) was added. The reaction mixture was stirred at 0° C. for 30 min, then allowed to warm to rt and stirred overnight. The reaction mixture was diluted with $CH_2Cl_2$ and washed with 5% aq HCl, water, and brine. The organic layer was dried with $Na_2SO_4$ and the solvents were evaporated. The crude product was purified via sgc (5% $MeOH/CH_2Cl_2$) to give Coompound 42 as a solid (1.04 g, 71%).

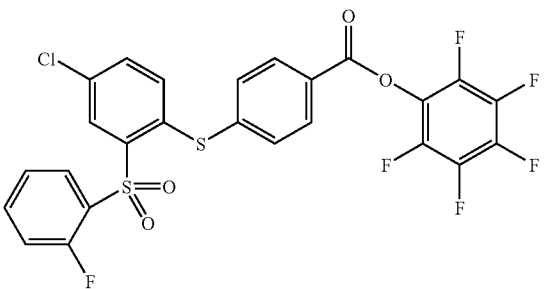

Compound 43

Compound 43. Pentafluorophenol (0.91 g, 4.94 mmol) and Compound 42 (1.04 g, 2.46 mmol) were dissolved in 30 mL of $CH_2Cl_2$ and EDCl was added. The reaction was stirred overnight and diluted with water and $CH_2Cl_2$. The layers were separated and the organic layer was washed with water and dried with $Na_2SO_4$. The crude product was purified via sgc (5% EtOAc/hexanes) to give 0.9 g (62%) of Compound 43 as a solid.

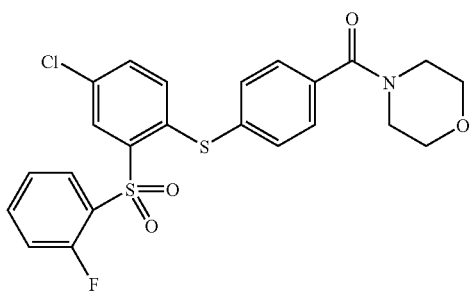

Compound XXVII

Compound XXVII. Compound 43 (0.15 g, 0.25 mmol) was dissolved in $CH_2Cl_2$ (5 mL). Morpholine (44 mg, 0.51 mmol) and DIPEA (49 mg, 0.38 mmol) were added and the reaction mixture was stirred at rt for 2 h. The reaction mixture was diluted with EtOAc and washed with 5% aq $NaHCO_3$, water and brine. The organic layer was dried with $Na_2SO_4$ and the solvents were evaporated. The crude product was purified via sgc (50% EtOAc/hexanes) to give 98 mg (77%) of Compound XXVII.

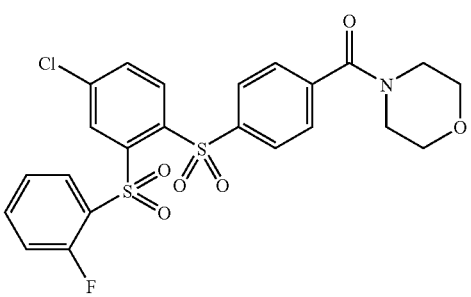

Compound XXVIII

Compound XXVIII. Compound XXXVII (72 mg, 0.146 mmol) was dissolved in $CH_2Cl_2$ (3 mL) and MCPBA (ca 50%, 0.11 g, ca 0.36 mmol) was added. The reaction mixture was stirred overnight then diluted with $CH_2Cl_2$. The reaction mixture was washed with aq $Na_2CO_3$ and water then dried with $Na_2SO_4$. The solvents were evaporated and the crude product was purified via sgc (60% EtOAc/hexanes) to give 61 mg (79%) of Compound XXXVIII as a solid.

EXAMPLE XIX

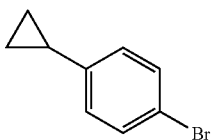

Compound 44

Compound 44. Cyclopropyl benzene (48.5 g, 410 mmol), glacial acetic acid (510 mL), and sodium acetate (38.9 g, 474 mmol) were added to a roundbottomed flask. The flask was cooled in an ice-water bath. A solution of bromine (66.3 g, 414 mmol) dissolved in 105 mL of acetic acid was added dropwise over 90 min. The reaction mixture was stirred at temperatures between 0° C. and 10 ° C. for 5 h. The reaction was then allowed to warm to rt overnight. Hexanes (1300 mL) and water (250 mL) were added. Aqueous $NaHSO_3$ (1M) was added until the reaction mixture changed from yellow to clear. The layers were separated. The organic layer was washed with water, 1M aq $Na_2CO_3$, and brine, then dried with $Na_2SO_4$. The solvent was evaporated and the crude product was purified via sgc using hexanes as the mobile phase to give 17 g of p-cyclopropylbromobenzene (21%) (Compound 44).

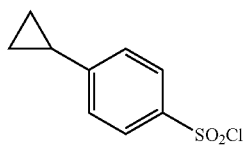

Compound 45

Compound 45. A flask was flame dried under N₂ blanket. Compound 44 (10.0 g, 50.7 mmol) was added, followed by dry THF (100 mL). The resulting solution was cooled to −78° C. A solution of n-butyl lithium in hexanes (2.27 M, 22.35 mL, 50.7 mmol) was added dropwise via syringe. The reaction mixture was stirred for 10 min. SO₂ gas was bubbled into the reaction mixture until the pH of a reaction mixture sample was <1 when mixed with water. The reaction mixture was stirred for 30 min at −78° C. The ice bath was removed and the reaction mixture was allowed to warm to rt. The reaction mixture was stirred for an additional 30 min at rt. The reaction mixture was concentrated to afford a solid. CH₂Cl₂ (500 mL) and N-chlorosuccinamide (10.2 g, 76 mmol) were added and the reaction mixture was stirred for 4 hrs at rt. Water and CH₂Cl₂ were added and the layers were separated. The organic layer was washed with water and brine, then dried with MgSO₄. The solution was filtered and the solvents were evaporated to give 13.3 g of crude p-cyclopropyl-benzenesulfonyl chloride (Compound 45).

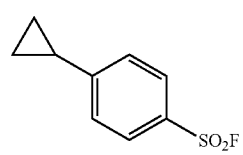

Compound 46

Compound 46. Crude compound 45 (13.3 g) was dissolved in 200 mL of acetone and 60 mL of water. Potassium fluoride (7.12 g, 122 mmol) was added and the reaction mixture was stirred overnight at rt. The reaction mixture was diluted with EtOAc and washed with water. The organic layer was dried with Na₂SO₄, filtered, and concentrated to dryness to give 9.80 g (97%) of crude p-cyclopropyl benzenesulfonyl fluoride (Compound 46).

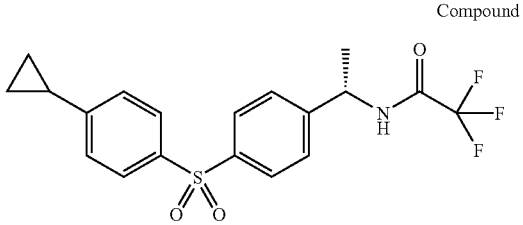

Compound 47

Compound 47. A flask was flame dried under N₂ blanket. Compound 1 (44.29 g, 150 mmol) was added, followed by 500 mL of anhydrous THF. The flask was cooled to −78° C. and a solution of n-butyl lithium in hexanes (1.77 M, 154 mL, 272 mmol) was added over 40 min. The reaction mixture was stirred for 1.5 h at −78° C., then transferred via cannula into a solution of crude p-cyclopropylbenzenesulfonyl fluoride (27.2 g, 135 mmol) dissolved in 200 mL of anhydrous THF over 1.5 h. The reaction mixture was stirred for 1 h. Water was added, followed by EtOAc. The layers were separated and the organic layer was washed with aq NH₄Cl, water, and brine, then dried with Na₂SO₄. The solvents were evaporated, and the crude product was purified by sgc (25%–33% EtOAc/Hexanes gradient mobile phase) to give 24.5 g (45%) of compound 47.

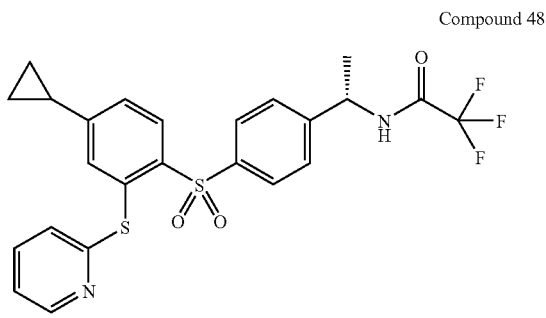

Compound 48

Compound 48. A flask was flame dried under N₂ blanket. Compound 47 (16.33 g, 41.1 mmol) was dissolved in 400 mL of anhydrous THF and cooled to −78° C. A solution of n-butyl lithium in hexanes (2.3 M, 35.7 mL, 82.1 mmol) was added dropwise via syringe. The reaction mixture was stirred for 1.5 h at −78° C. A solution of 2,2'-dithiodipyridine (8.89 g, 41.1 mmol) dissolved in 40 mL of THF was added and the reaction mixture was stirred for 2 h. The cold bath was removed, and the reaction mixture was allowed to warm to rt overnight. The reaction mixture was cooled with an ice-water bath and the reaction was quenched with 10 mL of water. The reaction mixture was diluted with EtOAc and washed with saturated aq NH₄Cl, water, and brine. The organic layer was dried with Na₂SO₄ and concentrated. The crude product was purified via sgc using 1:2 EtOAc/Hexanes as the mobile phase giving 15.49 g (74%) of Compound 48.

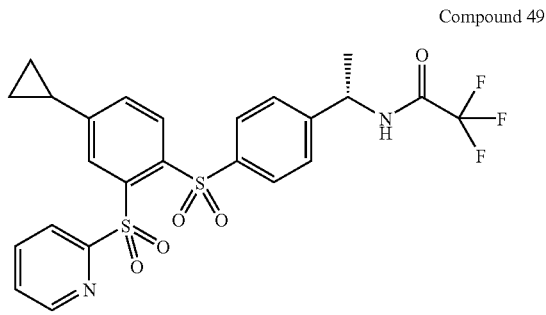

Compound 49

Compound 49. Compound 48 (15.49 g, 30.6 mmol) was dissolved in 1 L of CH₂Cl₂ and the flask was placed in a rt water bath. MCPBA (22.0 g, ca 74 mmol) was added in portions and the reaction mixture was left stirring overnight at rt. The reaction mixture was diluted with CH₂Cl₂ and washed with 10% aq NaHCO₃, water, and brine, then dried with Na₂SO₄. The solvent was evaporated and the crude product was purified via sgc using a 20%–50% EtOAc/Hexanes gradient as the mobile phase. Compound 49 (9.4 g, 57%) was isolated as a solid.

Compound 50

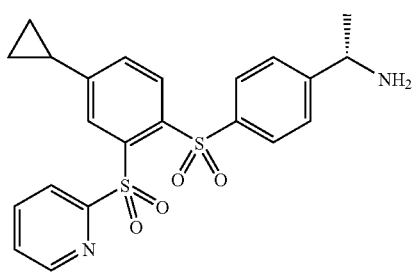

Compound 50. Compound 49 (10.16 g, 18.87 mmol) was dissolved in 300 mL of p-dioxane and 300 mL of 1.0 M aq LiOH was added. The reaction mixture was stirred at rt for 3 h. The reaction mixture was diluted with CH$_2$Cl$_2$. The layers were separated, and the organic layer was washed with water and brine, then dried with Na$_2$SO$_4$. The solvents were evaporated to give 9.0 g of crude Compound 50.

Compound XXIX

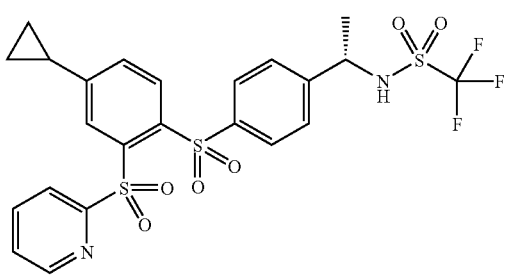

Compound XXIX. Crude compound 50 (7.74 g, 17.5 mmol) was dissolved in CH$_2$Cl$_2$ (250 mL). Diisopropylethylamine (2.71 g, 21 mmol) was added and the flask was cooled to −78° C. A solution of triflic anhydride (5.97 g, 21.1 mmol) dissolved in CH$_2$Cl$_2$ (50 mL) was added dropwise over 1 h. The reaction mixture was stirred for 2 h at −78° C. The cold bath was removed, and the reaction mixture was allowed to warm to rt overnight. The reaction mixture was diluted with CH$_2$Cl$_2$ and washed with water and brine. The organic layer was dried with Na$_2$SO$_4$ and the solvents were evaporated. The crude product was purified via sgc using 1:2 EtOAc/Hexanes as the mobile phase to give 8.61 g (85%) of Compound XXIX.

Compound XXIX: $^1$H NMR (300 MHz, CDCl$_3$): δ 8.56–8.52 (m, 1H), 8.32–8.21 (m, 3H), 8.02–7.92 (m, 4H), 5.42 (d, 9 Hz, 1H), 8.02–7.92 (m, 4H), 5.42 (d, 1H, 9 Hz), 4.84–4.78 (m, 1H), 2.16–2.06 (m, 1H), 1.60 (d, 7 Hz, 3H), 1.20–1.17 (m, 2H), 0.97–0.89 (m, 1H).

Compound XXX

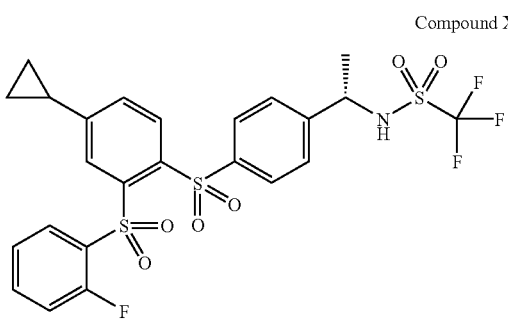

Compound XXX. Compound XXX was prepared from compound 47 using the procedures in example II.

Compound XXX: $^1$H NMR (300 MHz, CDCl$_3$): δ 8.33–8.22 (m, 3H), 8.00–7.94 (m, 2H), 7.66–7.58 (m, 1H), 7.53–7.37 (m, 4H), 7.16–7.05 (m, 1H), 5.160 (d, 9 Hz, 1H), 4.88–4.83 (m, 1H), 2.17–2.06 (m, 1H), 1.65 (d, 7 Hz, 3H), 1.28–1.20 (m, 2H), 0.97–0.90 (m, 2H).

Compound XXXI

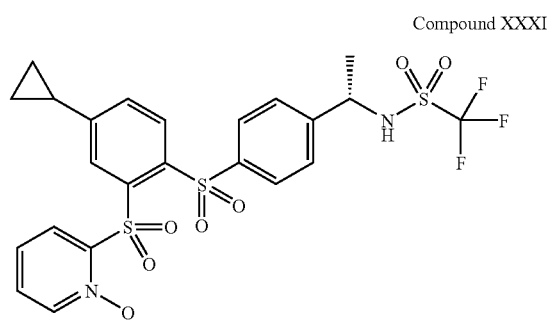

Compound XXXI. The potassium salt of compound XXIX (56 mg, 0.09 mmol) was dissolved in CH$_2$Cl$_2$ (5 mL) and Na$_2$HPO$_4$ (0.13 g, 0.91 mmol), and urea-hydrogen peroxide complex (85 mg, 0.90 mmol) were added. Trifluoroacetic acid was added (47 mg, 0.22 mmol) and the reaction mixture was refluxed for 4 h then left stirring overnight at rt. Additional urea-hydrogen peroxide complex (85 mg, 0.9 mmol) and TFAA (0.56 mmol) were added and the reaction mixture was refluxed for 6 h. The reaction mixture was allowed to cool to rt and diluted with CH$_2$Cl$_2$ and water. The layers were separated and the organic layer was washed with water, dried with Na$_2$SO$_4$, and concentrated. The crude product was purified via PTLC on silica using EtOAc as the mobile phase to give 34 mg (64%) of compound XXXI.

Compound XXXI: $^1$H NMR (300 MHz, CDCl$_3$): δ 8.38–8.29 (m, 2H), 8.17 (d, 8 Hz, 1H), 8.07–8.02 (m, 1H), 7.91–7.85 (m, 2H), 7.56–7.36 (m, 5H), 6.11 (d, 8 Hz, 1H), 4.84–4.78 (m, 1H), 2.12–2.01 (m, 1H), 1.57 (d, 7 Hz, 3H), 1.21–1.12 (m, 2H), 0.92–0.86 (m, 2H).

Compound XXXII

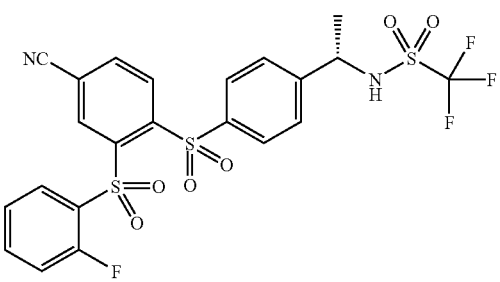

Compound XXXII. Compound V (0.50 g, 0.85 mmol), zinc (II) cyanide (65 mg, 0.55 mmol), zinc dust (11 mg, 0.17 mmol), 1,1'-Bis(diphenylphosphino)ferrocene (21 mg, 0.04 mmol), and tris(dibenzylidineacetone) dipalladium (17 mg, 0.129 mmol) were added to a 25 mL flask. Dimethylacetamide was added and the reaction mixture was placed under N$_2$ blanket and heated to 110 ° C. The reaction mixture was stirred at 110° C. for 4 h, then partitioned between EtOAc and water. The organic layer was washed with 2M ammonium hydroxide, water, and brine, then dried with MgSO$_4$. Evaporation of the solvent afforded 0.49 g of an oil that was purified via sgc using a 20%–25% EtOAc/Hexanes gradient mobile phase to afford compound XXXII (0.20 g).

Compound XXXIII

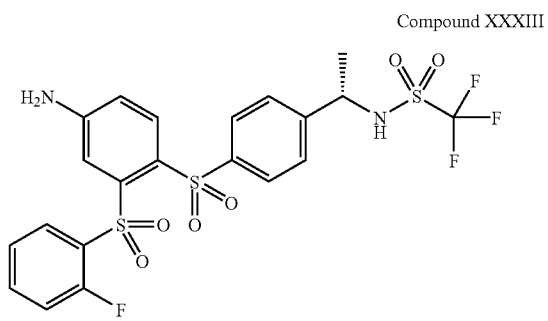

Compound XXXIII. Compound V (0.51 g, 0.87 mmol), tris(dibenzylidineacetone) dipalladium (40 mg, 0.04 mmol), 2-(dicyclohexylphosphino)-biphenyl (36 mg, 0.103 mmol), and sodium tert-butoxide (204 mg, 2.12 mmol) were added to a Schlenck flask under N$_2$ blanket. Toluene (2.5 mL) was added, followed by benzophenone imine (210 mg, 1.15 mmol). The reaction mixture was stirred overnight at 70° C. under N$_2$. The reaction mixture was allowed to cool to rt and 1 M aq HCl was added. The reaction mixture was diluted with EtOAc and the layers were separated. The organic layer was washed with water and brine, then dried with MgSO$_4$. The resulting material was filtered and concentrated to give 0.37 g of an oil. The crude product was purified via sgc using a 25%–50% EtOAc/Hexanes gradient mobile phase, followed by a 5% MeOH/45% EtOAc/50% Hexanes mobile phase to give 0.11 g of an oil as product.

Compound XXXIV

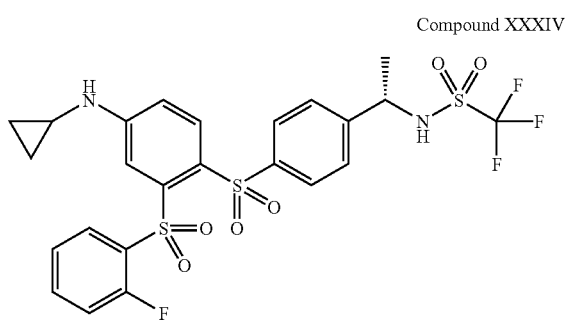

Compound XXXIV. Compound V (264 mg, 0.45 mmol), sodium tert-butoxide (103 mg, 1.07 mmol), tris(dibenzylideneacetone) dipalladium (107 mg, 0.116 mmol), and 2-(di-tert-butyl-phosphino)biphenyl (61 mg, 0.20 mmol) were added to a Schlenck flask under N$_2$. THF (1.5 mL) and cyclopropylamine (0.6 g, 10.5 mmol) were added and the reaction mixture was stirred for 24 h at rt. EtOAc and 1 M aq HCl were added and the layers were separated. The organic layer was washed with 1 M aq HCl, water, and brine, then dried with MgSO$_4$. Filtration and evaporation of the solvents gave an oil which was purified via sgc using 25% EtOAc/Hexanes as the mobile phase. Compound XXIV (109 mg) was obtained as a foam.

Compound XXXV

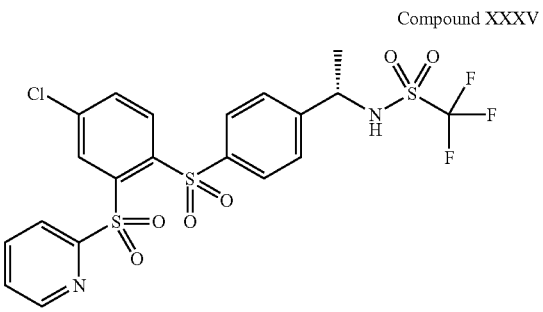

Compound XXXV. Compound XXXV was prepared from compound 5 according to the procedures in Example XIX.

Compound XXXV: $^1$H NMR (300 MHz, CDCl$_3$): δ 8.88 (d, 1.2 Hz, 1H), 8.51–8.56 (m, 2H), 8.31 (dd, 8 Hz, 1 Hz, 1H), 8.18 (dd, 8 Hz, 1 Hz, 1H), 8.08–7.96 (m, 3H), 7.62–7.48 (m, 3H), 5.51 (d, 9 Hz, 1H), 4.90–4.70 (m, 1H), 1.62 (d, 7 Hz, 3H).

Compound XXXVI

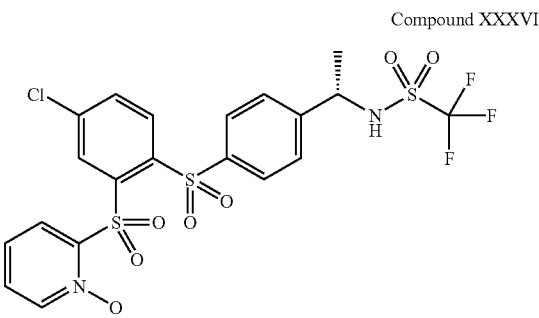

Compound XXXVI. Compound XXXVI was prepared from compound XXXV according to the procedure in Example XIX.

Compound XXXVI: $^1$H NMR (300 MHz, CDCl$_3$): δ 10.19 (d, 7.8 Hz, 1H), 8.27–8.42 (m, 4H), 8.13 (dd, 7.8 Hz, 2.1 Hz, 1H), 7.93 (d, 8.4 Hz, 2H), 7.78–7.63 (m, 2H), 7.59 (d, 8.4 Hz, 2H), 4.80 (m, 1H), 1.44 (d, 6.9 Hz, 3H).

Compound XXXVII

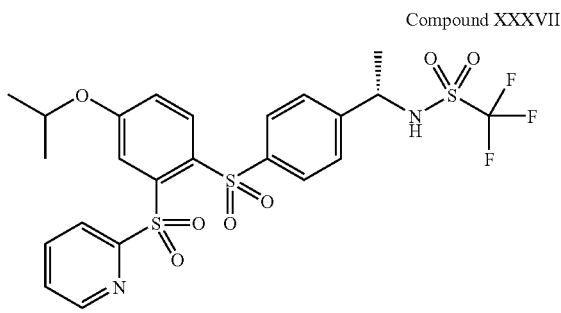

Compound XXXVII. Compound XXXV (0.312 g, 0.548 mmol) was dissolved in 2 propanol (20 mL) and 1.0 M aq NaOH was added (10 mL). The reaction mixture was stirred at temperatures between 80° C. to 84° C. for six days. The reaction mixture was allowed to cool to rt and partially concentrated. EtOAc was added and the layers were separated. The aqueous layer was acidified with 1 M aq H$_2$SO$_4$ and extracted with EtOAc. The combined organic layer was dried with MgSO$_4$ and concentrated to give 0.29 g of an oil. The crude product was purified via sgc using a 25%–33% EtOAc/Hexanes gradient as the mobile phase. The fraction containing Compound XXVII was repurified via sgc using 3% MeOH/CH$_2$Cl$_2$ as the mobile phase to give 0.05 g (15%) of Compound XXXVII as a solid.

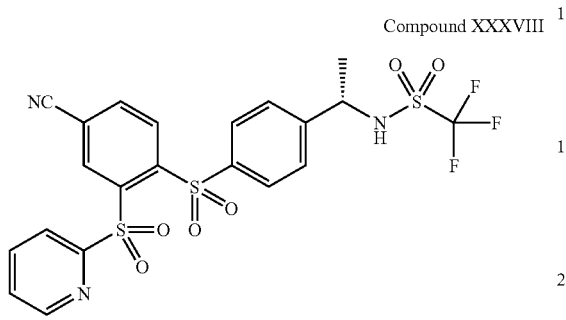

Compound XXXVIII

Compound XXXVIII. Compound XXXVIII was prepared from compound XXXV according to the procedure used to prepare compound XXXII.

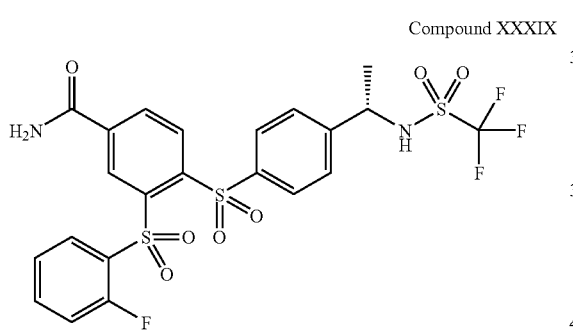

Compound XXXIX

Compound XXXIX. Compound XXXII (0.10 g, 0.17 mmol) was dissolved in acetone (1.5 mL) and water (1 mL). Potassium carbonate (3 mg, 0.022 mmol) and urea-hydrogen peroxide complex (0.16 g, 1.70 mmol) were added and the reaction mixture was stirred overnight at rt. The reaction mixture was diluted with EtOAc and washed with water. The solvents were evaporated and the crude product was purified via PTLC on SiO$_2$ using 50% EtOAc/Hexanes as the mobile phase to afford Compound XXXIX (75 mg, 73%) as a solid.

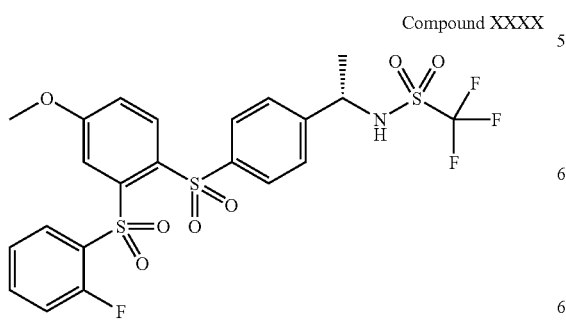

Compound XXXX

Compound XXXX. Compound XXXX was prepared from compound 2 according to the procedures in Example II.

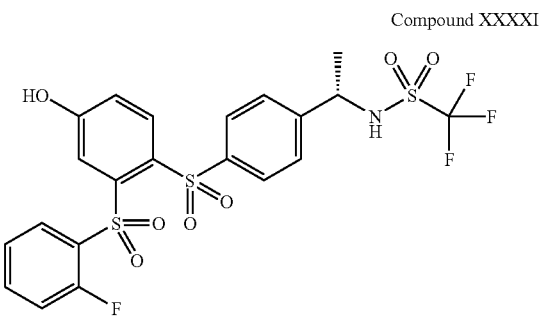

Compound XXXXI

Compound XXXXI. Compound XXXXI was prepared from compound XXXX according to the procedure used to convert compound 16 to compound X.

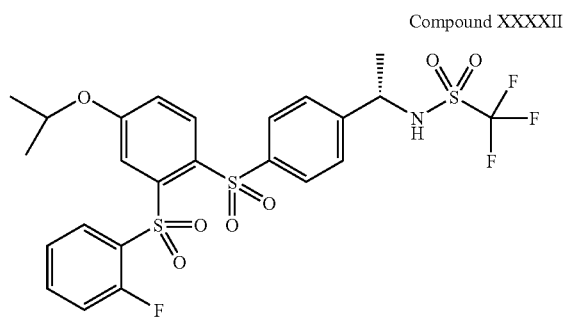

Compound XXXXII

Compound XXXXII. Compound XXXXI (0.15 g, 0.264 mmol) was dissolved in DMA (5 mL). Potassium iodide (0.22 g, 1.30 mmol), cesium carbonate (0.19 g, 0.58 mmol), and 2-bromopropane (49 mg, 0.398 mmol) were added and the reaction mixture was left stirring at rt over the weekend. EtOAc was added and the reaction mixture was washed with satd. aq NH$_4$Cl and water. The organic layer was dried with Na$_2$SO$_4$ and concentrated. The crude product was purified via sgc using 3% Et$_2$O/CH$_2$Cl$_2$ as the mobile phase to give 83 mg (51%) of Compound XXXXII.

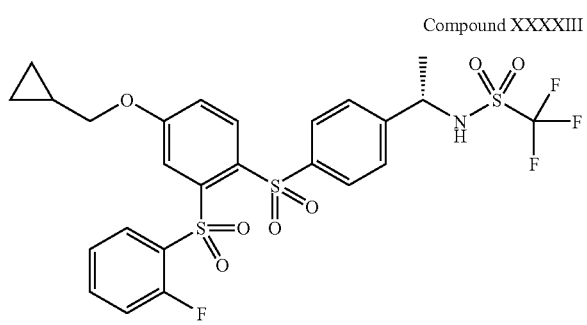

Compound XXXXIII

Compound XXXXIII. Compound XXXXI (0.10 g, 0.176 mmol) was dissolved in DMF (2 mL). Sodium hydride (7 mg, ca 1.2 eq) and bromomethylcyclopropane (26 mg, 0.19 mmol) were added and the reaction was stirred at 50° C. for 4 hr then allowed to cool to rt. EtOAc and water were added, and the layers were separated. The organic layer was washed with water and dried with Na$_2$SO$_4$. The solvent was evaporated and the crude product was purified via sgc using 33% EtOAc/Hexanes as the mobile phase to give 15 mg (14%) of Compound XXXXIII.

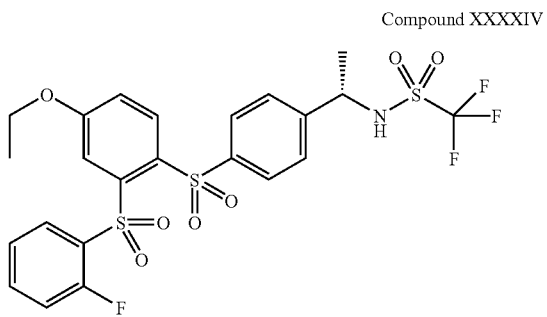

Compound XXXXIV

Compound XXXXIV. Compound XXXXIV was prepared according to the procedure used for Compound XXXXIII using ethyl iodide as the electrophile and stirring the reaction at rt overnight before workup.

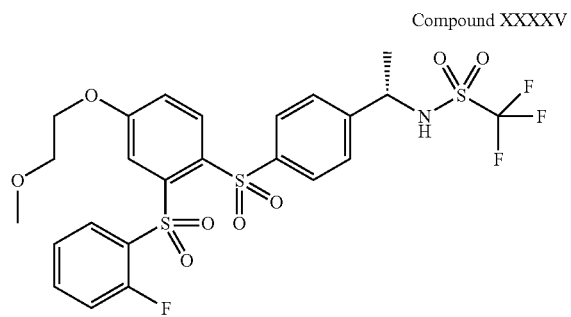

Compound XXXXV

Compound XXXXV. Compound XXXXI (0.40 g, 0.70 mmol) was dissolved in DMF (8 mL) and NaH (62 mg, ca 2.2 eq) was added. The reaction mixture was stirred for 30 min. Sodium iodide (0.52 g, 3.46 mmol) and 2-chloroethyl methyl ether (80 mg, 0.85 mmol) were added. The reaction mixture was stirred for 1 h at rt then 5 h at 110° C. The reaction mixture was allowed to cool to rt. EtOAc and satd aq NH$_4$Cl were added and the layers were separated. The organic layer was washed with water and dried with Na$_2$SO$_4$. Evaporation of the solvent, followed by sgc using 50% EtOAc/Hexanes as the mobile phase, afforded 0.21 g (48%) of Compound XXXXV.

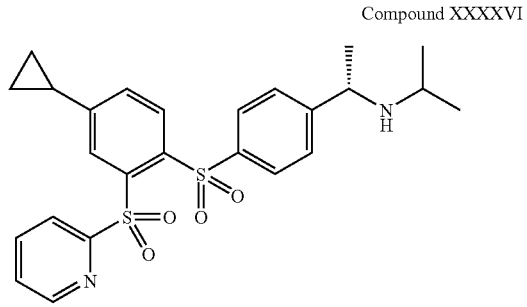

Compound XXXXVI

Compound XXXXVI. Compound 50 (50 mg, 0.11 mmol) was dissolved in CH$_2$Cl$_2$ (3 mL) and acetic acid (7 mg). Acetone (6 mg, 0.13 mmol), and NaBH(OAc)$_3$ (36 mg, 0.169) were added, and the reaction mixture was left stirring at rt overnight. EtOAc was added and the reaction mixture was washed with 10% Na$_2$CO$_3$ and water. The solvents were evaporated and the crude product was purified via PTLC on SiO$_2$ using EtOAc as the mobile phase. The resulting product was dissolved in EtOAc and HCl in Et$_2$O was added causing a white precipitate to form. The solvent was removed and the precipitate was washed with Et$_2$O and dried in vacuo to give 32 mg (49%) of compound XXXXVI as a solid.

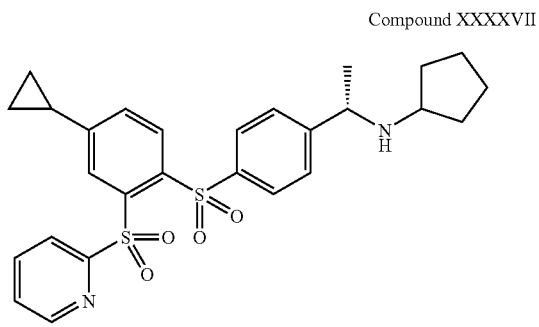

Compound XXXXVII

Compound XXXXVII. Compound XXXXVII was prepared according to the procedure used for compound XXXXVI using cyclopentanone as the carbonyl source.

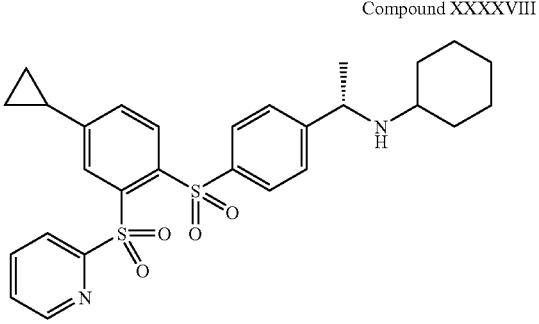

Compound XXXXVIII

Compound XXXXVIII. Compound XXXXVIII was prepared according to the procedure used for compound XXXXVI using cyclohexanone as the carbonyl source.

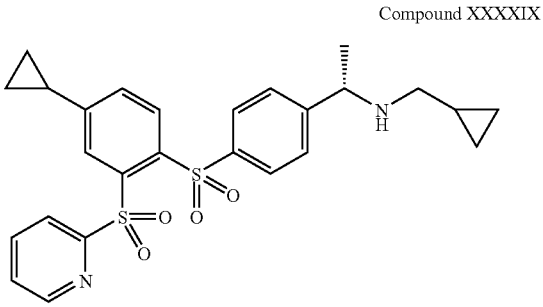

Compound XXXXIX

Compound XXXXIX. Compound XXXXIX was prepared according to the procedure used for compound XXXXVI using cyclopropanecarboxaldehyde as the carbonyl source.

Compound L

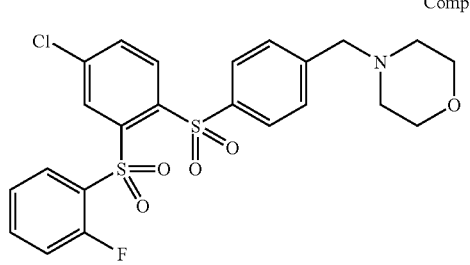

Compound L. Compound XXVIII (0.10 g, 0.197 mmol) was dissolved in a solution of borane in THF (1.0 M, 1.0 mL, 1.0 mmol). The reaction mixture was refluxed for 4 h then allowed to cool to rt. The solution was concentrated. Methanol (5 mL) and 1 M aq HCl (5 mL) were added and the resulting solution was stirred for 5 h at rt. The reaction mixture was concentrated and EtOAc was added. The resulting solution was washed with aq NaOH and water, then dried with $Na_2SO_4$. The solvent was evaporated and the crude product was purified via PTLC using 40% EtOAc/Hexanes as the mobile phase. The product isolated from this step was dissolved in EtOAC, and HCl in $Et_2O$ was added causing a precipitate to form. The solvent was removed and the precipitate was washed with $Et_2O$ and dried in vacuo to give 22 mg (21%) of Compound L as a solid.

Compound 51

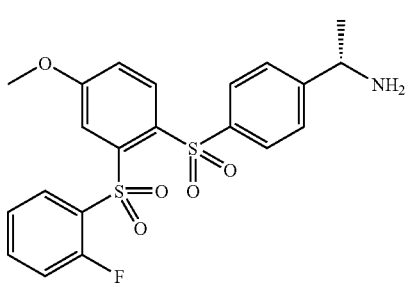

Compound 51 was prepared from Compound 2 according to the procedures in Example 11.

Compound LI

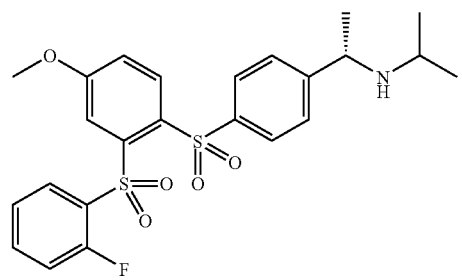

Compound LI. Compound LI was prepared from compound 51 according to the procedure used to prepare compound XXXXVI.

Compound LII

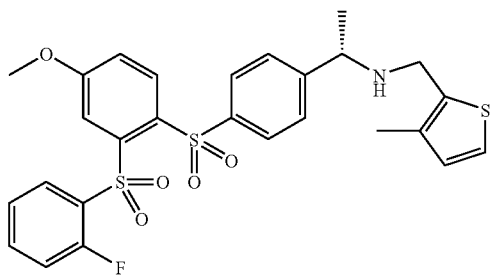

Compound LII. Compound LII was prepared from compound 51 according to the procedure used to prepare compound XXXXVI using 3-methyl-2-thiophenecarboxaldehyde as the carbonyl source.

Compound LIII

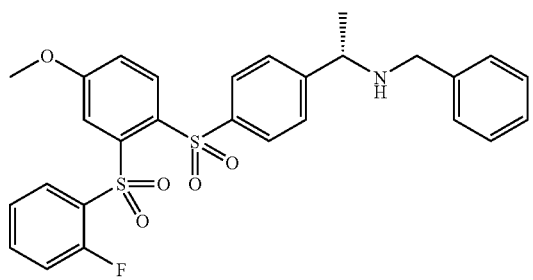

Compound LIII. Compound LIII was prepared from compound 51 according to the procedure used to prepare compound XXXXVI using benzaldehyde as the carbonyl source.

Compound 52

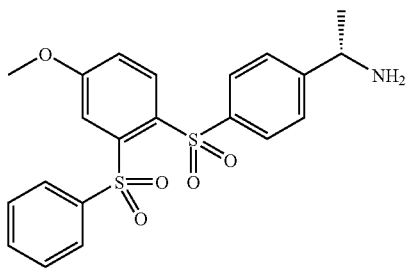

Compound 52. Compound 52 was prepared from compound 2 using the procedures in Example II with benzenesulfonyl fluoride as the initial electrophile.

Compound LIV

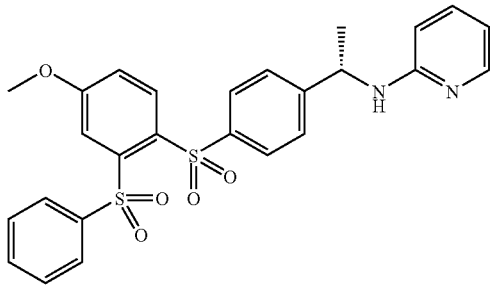

Compound LIV. Compound 52 (0.29 g, 0.67 mmol), cesium carbonate (0.44 g, 1.35 mmol), tris(dibenzylideneacetone) dipalladium (31 mg, 0.034 mmol), dppp (28 mg, 0.068 mmol), and 2-bromopyridine (0.16 g, 1.01 mmol) were dissolved in 11 mL of toluene under N₂ blanket. The reaction mixture was stirred at 80° C. overnight under N₂, then allowed to cool to rt. CH₂Cl₂ was added and the reaction mixture was washed with 2M aq NaHCO₃, water, and brine. The organic layer was dried with Na₂SO₄ and the solvent was evaporated. The crude product was purified via sgc using EtOAc as the mobile phase. The resulting material was dissolved in EtOAc and a solution of HCl/Et₂O was added. The solvents were evaporated to give 145 mg (42%) of Compound LIV as a solid.

Compound LV

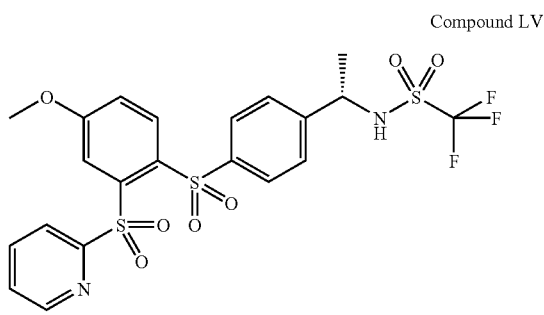

Compound LV. Compound XXXV (0.92 g, 1.67 mmol), was dissolved in methanol (40 mL) and 1.0 M aq NaOH was added (20 mL). The reaction mixture was stirred at 70° C. for 21 h. The reaction mixture was concentrated and extracted with EtOAc. The organic layer was washed with 1 M aq HCl, water, and brine, then dried with MgSO₄. The solvent was evaporated and the crude product was purified via sgc using 25%–33% EtOAc/Hexanes as the mobile phase. Compound LV (0.82 g, 90%) was isolated as an oil.
Compound XXXXV: ¹H NMR (300 MHz, CDCl₃): δ 8.56 (d, 3.9 Hz, 1H), 8.31–8.22 (m, 2H), 8.124 (d, 2.7 Hz, 1H), 8.05–7.95 (m, 1H), 7.92 (d, 8.4 Hz, 2H), 0.750–7.45 (m, 1H), 7.92 (d, 8.4 Hz, 2H), 7.27–7.23 (m, 2H), 5.8 (d, NH, 1H), 4.85–4.75 (m, 1H), 3.99 (s, 3H), 1.58 (d, 7.2 Hz, 3H).

Compound LVI

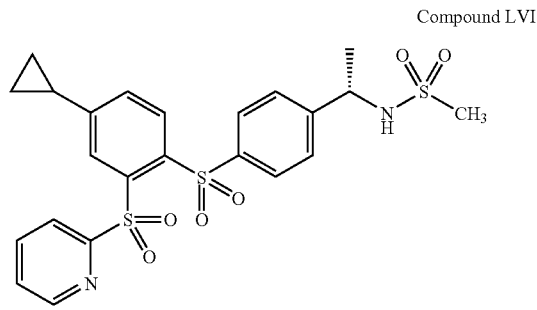

Compound LVI. Compound 50 was converted to compound LVI according to the procedure in Example II.
Compound LVI: ¹H NMR (300 MHz, CDCl₃): δ 8.56–8.52 (m, 1H), 8.31–8.23 (m, 3H), 8.02–7.90 (M, 4H), 4.87–4.78 (d, 7 Hz, 1H), 4.69 (m, 1 H), 2.66 (s, 3H), 2.16–2.06 (m, 1H), 1.51 (d, 7 Hz, 3H), 1.27–1.17 (m, 2H), 0.96–0.90 (m, 2H).

Compound 53

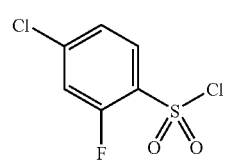

Compound 53. 2-fluoro-4-chloroaniline (22.90 g, 151 mmol) was dissolved in 120 mL of AcOH and 80 mL of concentrated HCl was added with stirring. The reaction mixture was cooled to 0° C. and a solution of NaNO₂ (27.2 g, 0.4 mol) dissolved in 40 mL of H₂O was added over 10 min. The reaction mixture was stirred for 30 min at 0° C. In a separate flask, 500 mg of CuCl was dissolved in 200 mL of AcOH. The flask was cooled to 0° C. and SO₂ gas was bubbled into the solution for 40 minutes. The contents of the "aniline" flask were added to the contents of the second flask over 20 minutes causing a vigorous evolution of gas. After the addition was complete, the ice bath was removed, and the reaction mixture was allowed to warm to rt. The reaction mixture was poured into 500 g of chipped ice and the resulting solids were collected, washed and dried to give 26.1 g (73%) of compound 53.

Compound 54

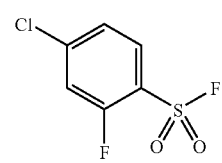

Compound 54. Compound 53 (4.0 g, 17.5 mmol) was dissolved in acetone (80 mL) and a solution of potassium fluoride (2.03 g, 35 mmol) in water (40 mL) was added. The reaction mixture was stirred at rt overnight. It was partially concentrated on the rotovap, then partitioned between CH₂Cl₂ and water. Evaporation of the solvent afforded Compound 54 (2.60 g, 70%) as an oil.

Compound 55

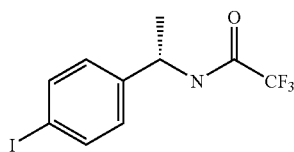

Compound 55. Compound 55 was prepared from a-methyl benzylamine using a procedure similar to that used to prepare compound 1. N-Iodosuccinamide was substituted for DBDMH and the product was recrystallized from isopropanol/water.

Compound 56

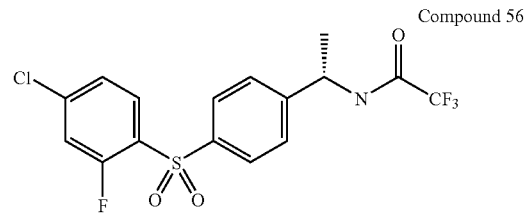

Compound 56. Compound 55 (4.33g, 12.5 mmol) was dissolved in THF (50 mL) and TMEDA (5.6 mL, 37 mmol) was added. The flask was placed under N₂ blanket and cooled to 0° C. A solution of isopropyl magnesium chloride (2.0 M in THF, 15 mL, 30 mmol) was added via syringe over 6 min. The reaction mixture was stirred at 0° C. for 1 h. The resulting solution was transferred via cannula into a flask containing compound 53 (15 mmol) in an ice-water bath over 15 min. The reaction mixture was left stirring at 0° C. for 1.5 h. Aq NH₄Cl was added and the reaction mixture was extracted with EtOAc. The combined organic layer was washed with brine and dried with MgSO₄. The solvents were evaporated and the crude product was purified via sgc using 1:4 EtOAc/Hexanes as the mobile phase. Solid compound 56 (3.5 g, 68%) was obtained.

Compound 57

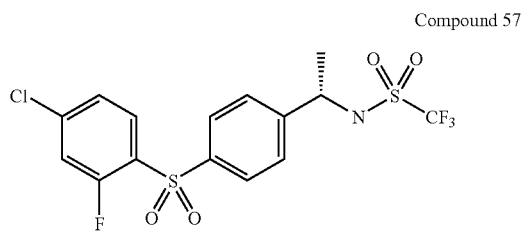

Compound 57. Compound 56 was converted to compound 57 using hydrolysis and sulfonylation procedures similar to those described in Example II.

Compound 58

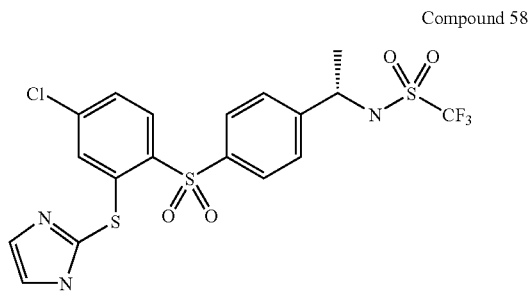

Compound 58. Compound 57 (0.10 g, 0.22 mmol) was dissolved in 1 mL of dioxane and 2-mercaptoimidazole was added (28 mg, 0.28 mmol). Sodium hydride (60% dispersion in mineral oil, 18 mg) was added and the reaction mixture was stirred at 100 ° C. for 8 h. The reaction mixture was quenched with ice and extracted with EtOAc. The organic layer was dried with MgSO₄ and the solvents were evaporated. The crude product was purified via sgc using a 5:95 MeOH/CH₂Cl₂ mobile phase to give 18 mg (15%) of compound 58 as product.

Compound LVII

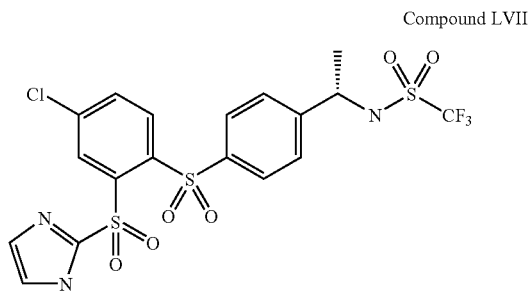

Compound LVII. Compound 57 was oxidized to compound LVII using a procedure similar to that used to oxidize Compound XIX to compound XXI.

It will be understood that various modifications may be made to the embodiments and examples disclosed herein. Therefore, the above description should not be construed as limiting, but merely as exemplifications of preferred embodiments. Those skilled in the art will envision various modifications within the pe and spirit of the claims appended hereto.

We claim:
1. A compound of the formula

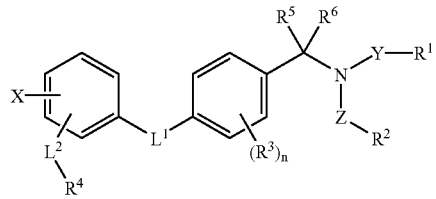

or a pharmaceutically acceptable salt or solvate thereof;
wherein:

$R^1$ is selected from the group consisting of H, alkyl, haloC$_1$-C$_6$alkyl, cycloalkyl, cycloalkylNH—, arylalkyl, heterocycloalkyl, heteroaryl, —N($R^2$)$_2$, —N($R^2$)aryl, unsubstituted aryl and aryl substituted with one to three X, wherein each $R^2$ can be the same or different and is independently selected when there are more than one $R^2$ present;

$R^2$ is selected from the group consisting of H and C$_1$-C$_6$ alkyl;

$R^3$ is 1–3 substituents selected from the group consisting of H, C$_1$-C$_6$ alkyl, Cl, F, CF$_3$, OCF$_2$H, OCF$_3$, OH and C$_1$-C$_6$ alkoxy, wherein $R^3$ can be the same or different and is independently selected when there are more than one $R^3$ present;

$R^4$ is pyridine-N-oxide or pyridyl optionally substituted with one to three X, wherein X can be the same or different and is independently selected when there are more than one X present;

$R^5$ is H or C$_1$-C$_6$ alkyl;

$R^6$ is H or C$_1$-C$_6$ alkyl; or $R^5$ and $R^6$ taken together with the carbon atom to which they are attached form a carbonyl group;

$L^1$ is —SO$_2$—, —SO—, or —S—;

$L^2$ is —SO$_2$—, —SO—, or —S—;

X is selected from the group consisting of H, halogen, CF$_3$, CN, OCF$_2$H, OCF$_2$CF$_3$, OCF$_3$, O$R^2$, C$_1$-C$_6$ alkyl, cycloalkyl, cycloalkoxy, C$_1$-C$_6$ alkoxy, alkoxyC$_1$-C$_6$ alkoxy, O-cycloalkyl, cycloalkylamino, cycloalkylalkoxy, heteroalkyl, —OSO$_2R^2$, —COO$R^2$, —CON($R^2$)$_2$, N($R^2$)$_2$, and N$R^2$aryl, wherein X can be the same or different, and is independently selected when there are more than one X present;

Y is a covalent bond, —CH$_2$—, —SO$_2$—, or —C(O)—;

Z is a covalent bond, —CH$_2$—, —SO$_2$— or —C(O)—; or

Y, $R^1$, Z and $R^2$ can be taken together with the nitrogen atom to which they are attached to form a heterocycloalkyl; with the following provisos:

$L^2$ and $R^4$, when taken together, cannot have two heteroatoms covalently bonded together;

when $R^2$ is H, Z cannot be —S(O)—, —SO$_2$—, or —C(O)—; and when Y is a covalent bond, $R^1$ cannot form a N—N bond with the nitrogen atom.

2. A compound according to claim 1 wherein
$L^1$ is —SO$_2$—, —S— or —S(O)—;
$L^2$ is —SO$_2$—;
$R^1$ is H, —CH$_3$NH$_2$, —CH$_2$CF$_3$, —NHC$_3$H$_7$, —NHC$_2$H$_6$, —NHC$_4$H$_9$, C$_1$–C$_6$alkyl, —CF$_3$, —CH(CH$_2$)$_2$, thiophenyl, morpholinyl, cyclopropyl, benzyl, naphthyl, —C(CH$_3$)$_3$, NHphenyl, 3,5-difluorophenyl, phenyl, N-cyclopentyl or N(CH$_3$)$_2$;
$R^2$ is H or CH$_3$;
$R^3$ is OH;
$R^4$ is pyridyl optionally substituted with one to three X, wherein X can be the same or different and are independently selected when the are more than one X present;
$R^5$ and $R^6$ are independently H or CH$_3$;
Y is a covalent bond, —SO$_2$— or —C(O)—;
Z is a covalent bond; or
$R^1$, Y, $R^2$ and Z taken together with the nitrogen atom form a morpholinyl group.

3. The compound according to claim 2 wherein
X is halogen, OH, or cyclopropyl;
$R^3$ is OH;
$R^5$ and $R^6$ are independently H or CH$_3$;
X is H, halogen, CF$_3$, OCH$_3$, OH, OCF$_3$, OCF$_2$H, CH$_3$ or C$_1$–C$_6$ cycloalkyl;
Y is a covalent bond;
Z is —SO$_2$— or —C(O)—;
$L^1$ is —SO$_2$—;
$L^2$ is —SO$_2$—;
$R^1$ is CH$_3$ or CF$_3$; and
$R^4$ is pyridyl, and said pyridyl group is optionally substituted with one to three substituents selected from the group consisting of C$_1$–C$_6$ alkyl, C$_1$–C$_6$ alkoxy, OH, CF$_3$ and halogen, wherein said substituents can be the same or different and are independently selected when there is more than one substituent.

4. The compound according to claim 1 of the formula

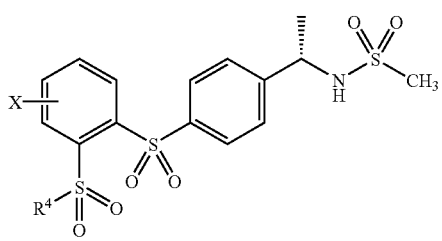

or a pharmaceutically acceptable salt or solvate thereof, wherein X and $R^4$ are as shown in the table below:

| Example | X | $R^4$ |
|---|---|---|
| T | Cl | |
| AO | Cl | |

5. The compound according to claim 1 of the formula

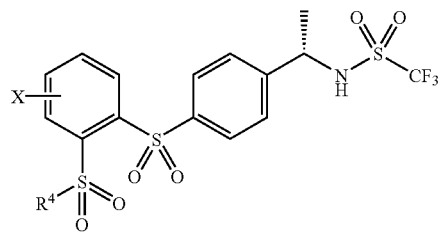

or a pharmaceutically acceptable salt or solvate thereof, wherein X and $R^4$ are as shown in the table below:

| Example | X | $R^4$ |
|---|---|---|
| GG | Cl | |
| GH | CF$_3$ | |

6. The compound according to claim 1 of the formula

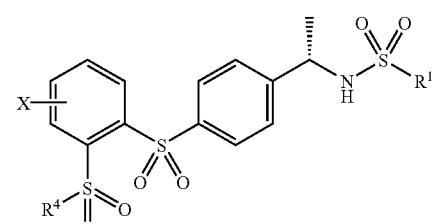

or a pharmaceutically acceptable salt or solvate thereof; wherein X, $R^1$ and $R^4$ are as shown in the table below:

| Example | X | $R^1$ | $R^4$ |
|---|---|---|---|
| GG | Cl | CF$_3$ | |
| GH | CF$_3$ | CF$_3$ | |

-continued

| Example | X | R¹ | R⁴ |
|---|---|---|---|
| XXIX |  | CF₃ | 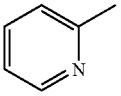 |
| XXXI |  | CF₃ | 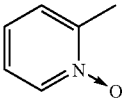 |
| XXXV | Cl | CF₃ | 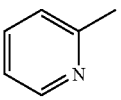 |
| XXXVI | Cl | CF₃ | 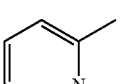 |
| XXXVII | 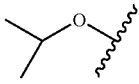 | CF₃ | 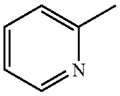 |
| XXXVIII | CN | CF₃ | 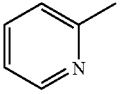 |
| XXXXXV | OCH₃ | CF₃ | 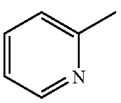 |
| XXXXXVI |  | CH₃ | 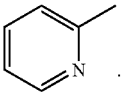 |

7. The compound according to claim 1 of the formula

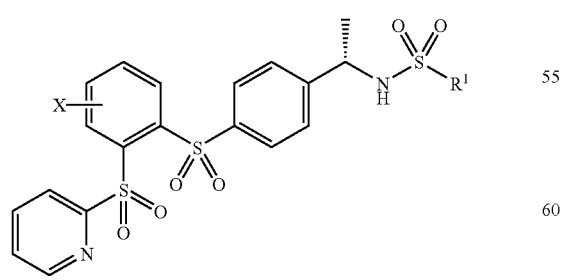

or a pharmaceutically acceptable salt or solvate thereof, wherein X is cyclopropyl and R¹ is CF₃.

8. The compound according to claim 1 of the formula

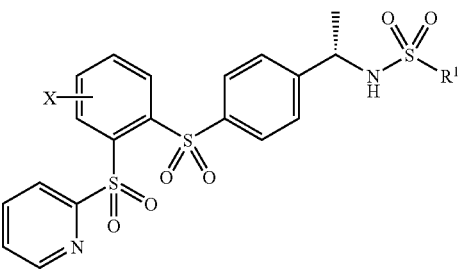

or a pharmaceutically acceptable salt or solvate thereof, wherein X is Cl and R¹ is CF₃.

9. The compound according to claim 1 of the formula

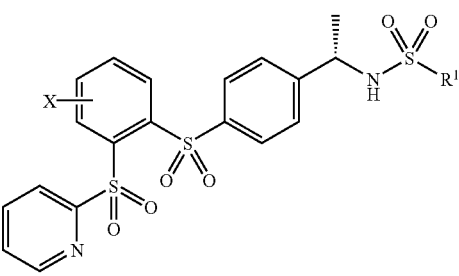

or a pharmaceutically acceptable salt or solvate thereof, wherein X is CF₃ and R¹ is CF₃.

10. The compound according to claim 1 of the formula

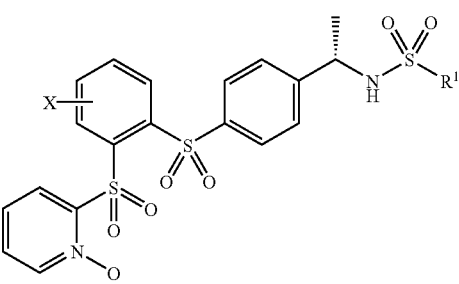

or a pharmaceutically acceptable salt or solvate thereof, wherein X is cyclopropyl and R¹ is CF₃.

11. The compound according to claim 1 of the formula

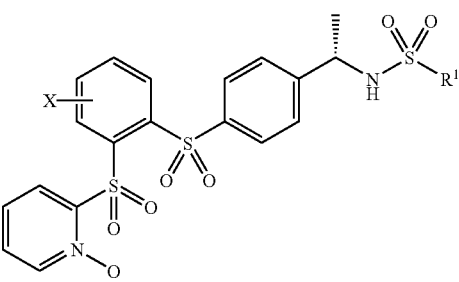

or a pharmaceutically acceptable salt or solvate thereof, wherein X is Cl and R¹ is CF₃.

12. The compound according to claim 1 of the formula or a pharmaceutically acceptable salt or solvate thereof, wherein X is cyclopropyl and R¹ is CH₃.

13. A pharmaceutical composition comprising one or more compounds according to claim 1 and one or more pharmaceutically acceptable carriers.

14. A pharmaceutical composition comprising one or more compounds according to claim 5 and one or more pharmaceutically acceptable carriers.

15. A pharmaceutical composition made by combining one or more compounds of claim 1 and one or more pharmaceutically acceptable carriers.

16. A composition which comprises one or more compounds selected from the group consisting of a COX-2 inhibitor, a COX-1 inhibitor, an immunosuppressive, a steroid, and an anti-TNF-α compound, and one or more compounds of claim 1.

17. A composition which comprises one or more compounds selected from the group consisting of a COX-2 inhibitor, a COX-1 inhibitor, an immunosuppressive, a steroid, and an anti-TNF-α compound, and one or more compounds of claim 5.

18. The composition of claim 16 wherein the COX-2 inhibitor is celecoxib or rofecoxib, the COX-1 inhibitor is piroxicam, the immunosuppressive is methotrexate, leflunomide, sulfasalazine or cyclosporin, the steroid is β-methasone and the anti-TNF-α compound is etanercept or infliximab.

19. The composition of claim 17 wherein the COX-2 inhibitor is celecoxib or rofecoxib, the COX-1 inhibitor is piroxicam, the immunosuppressive is methotrexate, leflunomide, sulfasalazine or cyclosporin, the steroid is β-methasone and the anti-TNF-α compound is etanercept or infliximab.

20. A composition which comprises one or more compounds selected from the group consisting of interferon beta-1a, interferon beta-1b, and glatiramer acetate, and one or more compounds of claim 1.

21. A composition which comprises one or more compounds selected from the group consisting of interferon beta-1a, interferon beta-1b, and glatiramer acetate, and one or more compounds of claim 5.

22. A composition which comprises one or more compounds selected from the group consisting of an immunosuppressive, a steroid, and an anti-TNF-α compound, and one or more compounds of claim 1.

23. A composition which comprises one or more compounds selected from the group consisting of an immunosuppressive, a steroid, and an anti-TNF-α compound, and one or more compounds of claim 5.

24. The composition of claim 22 wherein the immunosuppressive is methotrexate, leflunomide, sulfasalazine or cyclosporin, the steroid is β-methasone and the anti-TNF-α compound is etanercept or infliximab.

25. The composition of claim 23 wherein the immunosuppressive is methotrexate, leflunomide, sulfasalazine or cyclosporin, the steroid is β-methasone and the anti-TNF-α compound is etanercept or infliximab.

26. The compound according to claim 1 of the formula or a pharmaceutically acceptable salt or solvate thereof, wherein X is cyclopropyl and R¹ is CF₃.

27. The compound according to claim 1 of the formula or a pharmaceutically acceptable salt or solvate thereof, wherein X is Cl and R¹ is CF₃.

28. The compound according to claim 1 of the formula or a pharmaceutically acceptable salt or solvate thereof, wherein X is CF₃ and R¹ is CF₃.

29. The compound according to claim 1 of the formula or a pharmaceutically acceptable salt or solvate thereof, wherein X is cyclopropyl and R¹ is CF₃.

30. The compound according to claim 1 of the formula
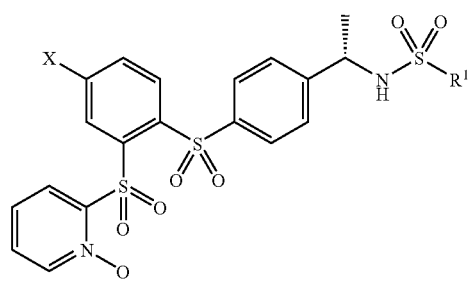
or a pharmaceutically acceptable salt or solvate thereof, wherein X is Cl and $R^1$ is $CF_3$.
31. compound according to claim 1 of the formula
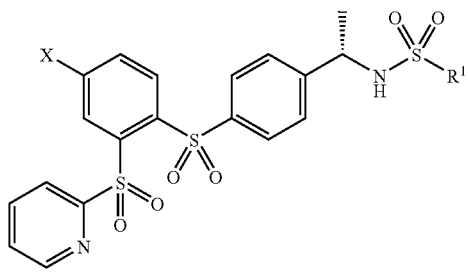
or a pharmaceutically acceptable salt or solvate thereof, wherein X is cyclopropyl and $R^1$ is $CH_3$.
* * * * *